United States Patent
D'Amato et al.

(10) Patent No.: US 11,138,969 B2
(45) Date of Patent: Oct. 5, 2021

(54) LOCALLY DISTRIBUTED KEYWORD DETECTION

(71) Applicant: Sonos, Inc., Santa Barbara, CA (US)

(72) Inventors: Nick D'Amato, Santa Barbara, CA (US); Connor Kristopher Smith, New Hudson, MI (US)

(73) Assignee: Sonos, Inc., Santa Barbara, CA (US)

( * ) Notice: Subject to any disclaimer, the term of this patent is extended or adjusted under 35 U.S.C. 154(b) by 90 days.

(21) Appl. No.: 16/528,265

(22) Filed: Jul. 31, 2019

(65) Prior Publication Data

US 2021/0035561 A1    Feb. 4, 2021

(51) Int. Cl.
| | |
|---|---|
| *G10L 15/08* | (2006.01) |
| *G10L 15/22* | (2006.01) |
| *G10L 15/30* | (2013.01) |
| *G06F 3/16* | (2006.01) |

(52) U.S. Cl.
CPC .............. *G10L 15/08* (2013.01); *G06F 3/167* (2013.01); *G10L 15/22* (2013.01); *G10L 15/30* (2013.01); *G10L 2015/088* (2013.01); *G10L 2015/223* (2013.01)

(58) Field of Classification Search
USPC ...................................................... 704/1–504
See application file for complete search history.

(56) References Cited

U.S. PATENT DOCUMENTS

| | | |
|---|---|---|
| 4,741,038 A | 4/1988 | Elko et al. |
| 4,941,187 A | 7/1990 | Slater |
| 5,440,644 A | 8/1995 | Farinelli et al. |
| 5,588,065 A | 12/1996 | Tanaka et al. |
| 5,740,260 A | 4/1998 | Odom |

(Continued)

FOREIGN PATENT DOCUMENTS

| | | |
|---|---|---|
| AU | 2017100486 A4 | 6/2017 |
| AU | 2017100581 A4 | 6/2017 |

(Continued)

OTHER PUBLICATIONS

US 9,299,346 B1, 03/2016, Hart et al. (withdrawn)

(Continued)

*Primary Examiner* — Marcus T Riley
(74) *Attorney, Agent, or Firm* — Fortem IP LLP; Matt Lincicum

(57) ABSTRACT

In one aspect, a playback device includes a command-keyword engine having a local natural language unit (NLU). The playback device detects, via the command-keyword engine, a first command keyword in voice input of sound detected by one or more microphones of the playback device. The playback device determines whether the sound input data includes a keyword from a first predetermined library of keywords via a local natural language unit (NLU). The playback device transmits the input sound data to a second playback device over a local area network, the second playback device employing a second local NLU with a second predetermined library of keywords. The playback device receives a response from the second playback device and performs an action based on an intent determined by at least one of the first NLU or the second NLU according to the keywords in the voice input.

17 Claims, 18 Drawing Sheets

(56) References Cited

U.S. PATENT DOCUMENTS

| | | |
|---|---|---|
| 5,761,320 A | 6/1998 | Farinelli et al. |
| 5,923,902 A | 7/1999 | Inagaki |
| 5,949,414 A | 9/1999 | Namikata et al. |
| 6,032,202 A | 2/2000 | Lea et al. |
| 6,088,459 A | 7/2000 | Hobelsberger |
| 6,256,554 B1 | 7/2001 | Dilorenzo |
| 6,301,603 B1 | 10/2001 | Maher et al. |
| 6,311,157 B1 | 10/2001 | Strong |
| 6,404,811 B1 | 6/2002 | Cvetko et al. |
| 6,408,078 B1 | 6/2002 | Hobelsberger |
| 6,469,633 B1 | 10/2002 | Wachter et al. |
| 6,522,886 B1 | 2/2003 | Youngs et al. |
| 6,594,347 B1 | 7/2003 | Calder et al. |
| 6,594,630 B1 | 7/2003 | Zlokarnik et al. |
| 6,611,537 B1 | 8/2003 | Edens et al. |
| 6,611,604 B1 | 8/2003 | Irby et al. |
| 6,631,410 B1 | 10/2003 | Kowalski et al. |
| 6,757,517 B2 | 6/2004 | Chang et al. |
| 6,778,869 B2 | 8/2004 | Champion |
| 7,130,608 B2 | 10/2006 | Hollstrom et al. |
| 7,130,616 B2 | 10/2006 | Janik |
| 7,143,939 B2 | 12/2006 | Henzerling |
| 7,236,773 B2 | 6/2007 | Thomas |
| 7,295,548 B2 | 11/2007 | Blank et al. |
| 7,391,791 B2 | 6/2008 | Balassanian et al. |
| 7,483,538 B2 | 1/2009 | McCarty et al. |
| 7,571,014 B1 | 8/2009 | Lambourne et al. |
| 7,630,501 B2 | 12/2009 | Blank et al. |
| 7,643,894 B2 | 1/2010 | Braithwaite et al. |
| 7,657,910 B1 | 2/2010 | McAulay et al. |
| 7,661,107 B1 | 2/2010 | Van Dyke et al. |
| 7,702,508 B2 | 4/2010 | Bennett |
| 7,792,311 B1 | 9/2010 | Holmgren et al. |
| 7,853,341 B2 | 12/2010 | McCarty et al. |
| 7,961,892 B2 | 6/2011 | Fedigan |
| 7,987,294 B2 | 7/2011 | Bryce et al. |
| 8,014,423 B2 | 9/2011 | Thaler et al. |
| 8,032,383 B1 | 10/2011 | Bhardwaj et al. |
| 8,041,565 B1 | 10/2011 | Bhardwaj et al. |
| 8,045,952 B2 | 10/2011 | Qureshey et al. |
| 8,073,125 B2 | 12/2011 | Zhang et al. |
| 8,073,681 B2 | 12/2011 | Baldwin et al. |
| 8,103,009 B2 | 1/2012 | McCarty et al. |
| 8,136,040 B2 | 3/2012 | Fleming |
| 8,234,395 B2 | 7/2012 | Millington |
| 8,239,206 B1 | 8/2012 | Lebeau et al. |
| 8,255,224 B2 | 8/2012 | Singleton et al. |
| 8,284,982 B2 | 10/2012 | Bailey |
| 8,290,603 B1 | 10/2012 | Lambourne |
| 8,340,975 B1 | 12/2012 | Rosenberger et al. |
| 8,364,481 B2 | 1/2013 | Strope et al. |
| 8,385,557 B2 | 2/2013 | Tashev et al. |
| 8,386,261 B2 | 2/2013 | Mellott et al. |
| 8,423,893 B2 | 4/2013 | Ramsay et al. |
| 8,428,758 B2 | 4/2013 | Naik et al. |
| 8,453,058 B1 | 5/2013 | Coccaro et al. |
| 8,473,618 B2 | 6/2013 | Spear et al. |
| 8,483,853 B1 | 7/2013 | Lambourne |
| 8,484,025 B1 | 7/2013 | Moreno Mengibar et al. |
| 8,738,925 B1 | 5/2014 | Park et al. |
| 8,831,761 B2 | 9/2014 | Kemp et al. |
| 8,831,957 B2 | 9/2014 | Taubman et al. |
| 8,848,879 B1 | 9/2014 | Coughlan et al. |
| 8,861,756 B2 | 10/2014 | Zhu et al. |
| 8,874,448 B1 | 10/2014 | Kauffmann et al. |
| 8,938,394 B1 | 1/2015 | Faaborg et al. |
| 8,942,252 B2 | 1/2015 | Balassanian et al. |
| 8,983,383 B1 | 3/2015 | Haskin |
| 8,983,844 B1 | 3/2015 | Thomas et al. |
| 9,015,049 B2 | 4/2015 | Baldwin et al. |
| 9,042,556 B2 | 5/2015 | Kallai et al. |
| 9,060,224 B1 | 6/2015 | List |
| 9,094,539 B1 | 7/2015 | Noble |
| 9,215,545 B2 | 12/2015 | Dublin et al. |
| 9,251,793 B2 | 2/2016 | Lebeau et al. |
| 9,253,572 B2 | 2/2016 | Beddingfield, Sr. et al. |
| 9,262,612 B2 | 2/2016 | Cheyer |
| 9,275,637 B1 | 3/2016 | Salvador et al. |
| 9,288,597 B2 | 3/2016 | Carlsson et al. |
| 9,300,266 B2 | 3/2016 | Grokop |
| 9,304,736 B1 | 4/2016 | Whiteley et al. |
| 9,307,321 B1 | 4/2016 | Unruh |
| 9,318,107 B1 | 4/2016 | Sharifi |
| 9,319,816 B1 | 4/2016 | Narayanan |
| 9,324,322 B1 | 4/2016 | Torok et al. |
| 9,335,819 B1 | 5/2016 | Jaeger et al. |
| 9,361,878 B2 | 6/2016 | Boukadakis |
| 9,368,105 B1 | 6/2016 | Freed et al. |
| 9,374,634 B2 | 6/2016 | Macours |
| 9,386,154 B2 | 7/2016 | Baciu et al. |
| 9,401,058 B2 | 7/2016 | De La Fuente et al. |
| 9,412,392 B2 | 8/2016 | Lindahl et al. |
| 9,426,567 B2 | 8/2016 | Lee et al. |
| 9,431,021 B1 | 8/2016 | Scalise et al. |
| 9,443,527 B1 | 9/2016 | Watanabe et al. |
| 9,472,201 B1 | 10/2016 | Sleator |
| 9,472,203 B1 | 10/2016 | Ayrapetian et al. |
| 9,484,030 B1 * | 11/2016 | Meaney ................ H04R 3/005 |
| 9,489,948 B1 | 11/2016 | Chu et al. |
| 9,494,683 B1 | 11/2016 | Sadek |
| 9,509,269 B1 | 11/2016 | Rosenberg |
| 9,510,101 B1 | 11/2016 | Polleros |
| 9,514,476 B2 | 12/2016 | Kay et al. |
| 9,514,752 B2 | 12/2016 | Sharifi |
| 9,516,081 B2 | 12/2016 | Tebbs et al. |
| 9,536,541 B2 | 1/2017 | Chen et al. |
| 9,548,053 B1 | 1/2017 | Basye et al. |
| 9,548,066 B2 | 1/2017 | Jain et al. |
| 9,552,816 B2 | 1/2017 | Vanlund et al. |
| 9,554,210 B1 | 1/2017 | Ayrapetian et al. |
| 9,560,441 B1 | 1/2017 | McDonough, Jr. et al. |
| 9,576,591 B2 | 2/2017 | Kim et al. |
| 9,601,116 B2 | 3/2017 | Casado et al. |
| 9,615,170 B2 | 4/2017 | Kirsch et al. |
| 9,615,171 B1 | 4/2017 | O'Neill et al. |
| 9,626,695 B2 | 4/2017 | Balasubramanian et al. |
| 9,632,748 B2 | 4/2017 | Faaborg et al. |
| 9,633,186 B2 | 4/2017 | Ingrassia, Jr. et al. |
| 9,633,368 B2 | 4/2017 | Greenzeiger et al. |
| 9,633,660 B2 | 4/2017 | Haughay et al. |
| 9,633,671 B2 | 4/2017 | Giacobello et al. |
| 9,633,674 B2 | 4/2017 | Sinha et al. |
| 9,640,179 B1 | 5/2017 | Hart et al. |
| 9,640,183 B2 | 5/2017 | Jung et al. |
| 9,641,919 B1 | 5/2017 | Poole et al. |
| 9,646,614 B2 | 5/2017 | Bellegarda et al. |
| 9,653,060 B1 | 5/2017 | Hilmes et al. |
| 9,653,075 B1 | 5/2017 | Chen et al. |
| 9,659,555 B1 | 5/2017 | Hilmes et al. |
| 9,672,821 B2 | 6/2017 | Krishnaswamy et al. |
| 9,674,587 B2 | 6/2017 | Triplett et al. |
| 9,685,171 B1 | 6/2017 | Yang |
| 9,691,378 B1 | 6/2017 | Meyers et al. |
| 9,691,379 B1 | 6/2017 | Mathias et al. |
| 9,697,826 B2 | 7/2017 | Sainath et al. |
| 9,697,828 B1 | 7/2017 | Prasad et al. |
| 9,698,999 B2 | 7/2017 | Mutagi et al. |
| 9,704,478 B1 | 7/2017 | Vitaladevuni et al. |
| 9,721,566 B2 | 8/2017 | Newendorp et al. |
| 9,721,568 B1 | 8/2017 | Polansky et al. |
| 9,721,570 B1 | 8/2017 | Beal et al. |
| 9,728,188 B1 | 8/2017 | Rosen et al. |
| 9,734,822 B1 | 8/2017 | Sundaram et al. |
| 9,743,204 B1 | 8/2017 | Welch et al. |
| 9,747,011 B2 | 8/2017 | Lewis et al. |
| 9,747,899 B2 | 8/2017 | Pogue et al. |
| 9,747,920 B2 | 8/2017 | Ayrapetian et al. |
| 9,747,926 B2 | 8/2017 | Sharifi et al. |
| 9,754,605 B1 | 9/2017 | Chhetri |
| 9,762,967 B2 | 9/2017 | Clarke et al. |
| 9,811,314 B2 | 11/2017 | Plagge et al. |
| 9,813,810 B1 | 11/2017 | Nongpiur |
| 9,813,812 B2 | 11/2017 | Berthelsen et al. |
| 9,820,036 B1 | 11/2017 | Tritschler et al. |

(56) References Cited

U.S. PATENT DOCUMENTS

| | | |
|---|---|---|
| 9,820,039 B2 | 11/2017 | Lang |
| 9,826,306 B2 | 11/2017 | Lang |
| 9,865,259 B1 | 1/2018 | Typrin et al. |
| 9,865,264 B2 | 1/2018 | Gelfenbeyn et al. |
| 9,881,616 B2 | 1/2018 | Beckley et al. |
| 9,900,723 B1 | 2/2018 | Choisel et al. |
| 9,916,839 B1 | 3/2018 | Scalise et al. |
| 9,947,316 B2 | 4/2018 | Millington et al. |
| 9,947,333 B1 | 4/2018 | David |
| 9,973,849 B1 | 5/2018 | Zhang et al. |
| 10,013,995 B1 | 7/2018 | Lashkari et al. |
| 10,026,401 B1 | 7/2018 | Mutagi et al. |
| 10,048,930 B1 | 8/2018 | Vega et al. |
| 10,051,366 B1 | 8/2018 | Buoni et al. |
| 10,051,600 B1 | 8/2018 | Zhong et al. |
| RE47,049 E | 9/2018 | Zhu et al. |
| 10,074,369 B2 * | 9/2018 | Devaraj ............... H04L 67/306 |
| 10,079,015 B1 * | 9/2018 | Lockhart ............... G10L 15/08 |
| 10,134,399 B2 | 11/2018 | Lang et al. |
| 10,136,204 B1 | 11/2018 | Poole et al. |
| 10,152,969 B2 | 12/2018 | Reilly et al. |
| 10,186,265 B1 * | 1/2019 | Lockhart ............... G10L 15/32 |
| 10,276,161 B2 | 4/2019 | Hughes et al. |
| 10,297,256 B2 | 5/2019 | Reilly et al. |
| 10,339,917 B2 | 7/2019 | Aleksic et al. |
| 10,354,650 B2 | 7/2019 | Gruenstein et al. |
| 10,365,887 B1 * | 7/2019 | Mulherkar ............. G06F 3/167 |
| 10,366,688 B2 | 7/2019 | Gunn et al. |
| 10,381,001 B2 | 8/2019 | Gunn et al. |
| 10,381,002 B2 | 8/2019 | Gunn et al. |
| 10,381,003 B2 | 8/2019 | Wakisaka et al. |
| 10,388,272 B1 * | 8/2019 | Thomson ............. G10L 15/063 |
| 10,445,057 B2 | 10/2019 | Vega et al. |
| 10,510,340 B1 * | 12/2019 | Fu ............................ G10L 15/22 |
| 10,522,146 B1 * | 12/2019 | Tushinskiy ............ G10L 15/22 |
| 10,586,540 B1 * | 3/2020 | Smith ...................... G06F 3/167 |
| 10,672,383 B1 * | 6/2020 | Thomson ............. G10L 15/183 |
| 10,679,625 B1 * | 6/2020 | Lockhart .............. G10L 15/26 |
| 10,762,896 B1 * | 9/2020 | Yavagal ................ G10L 15/183 |
| RE48,371 E | 12/2020 | Zhu et al. |
| 10,878,811 B2 * | 12/2020 | Smith ..................... G10L 15/08 |
| 10,943,598 B2 * | 3/2021 | Singh .................. G10L 21/0216 |
| 2001/0042107 A1 | 11/2001 | Palm |
| 2002/0022453 A1 | 2/2002 | Balog et al. |
| 2002/0026442 A1 | 2/2002 | Lipscomb et al. |
| 2002/0034280 A1 | 3/2002 | Infosino |
| 2002/0072816 A1 | 6/2002 | Shdema et al. |
| 2002/0116196 A1 | 8/2002 | Tran |
| 2002/0124097 A1 | 9/2002 | Isely et al. |
| 2003/0015354 A1 * | 1/2003 | Edwards ................ G01G 23/01 177/132 |
| 2003/0038848 A1 | 2/2003 | Lee et al. |
| 2003/0040908 A1 | 2/2003 | Yang et al. |
| 2003/0070869 A1 | 4/2003 | Hlibowicki |
| 2003/0072462 A1 | 4/2003 | Hlibowicki |
| 2003/0095672 A1 | 5/2003 | Hobelsberger |
| 2003/0157951 A1 | 8/2003 | Hasty |
| 2004/0024478 A1 | 2/2004 | Hans et al. |
| 2004/0093219 A1 | 5/2004 | Shin et al. |
| 2004/0127241 A1 | 7/2004 | Shostak |
| 2004/0128135 A1 | 7/2004 | Anastasakos et al. |
| 2005/0031131 A1 | 2/2005 | Browning et al. |
| 2005/0031132 A1 | 2/2005 | Browning et al. |
| 2005/0031133 A1 | 2/2005 | Browning et al. |
| 2005/0031134 A1 | 2/2005 | Leske |
| 2005/0031137 A1 | 2/2005 | Browning et al. |
| 2005/0031138 A1 | 2/2005 | Browning et al. |
| 2005/0031139 A1 | 2/2005 | Browning et al. |
| 2005/0031140 A1 | 2/2005 | Browning |
| 2005/0047606 A1 | 3/2005 | Lee et al. |
| 2005/0077843 A1 | 4/2005 | Benditt |
| 2005/0164664 A1 | 7/2005 | Difonzo et al. |
| 2005/0195988 A1 | 9/2005 | Tashev et al. |
| 2005/0207584 A1 | 9/2005 | Bright |
| 2005/0268234 A1 | 12/2005 | Rossi et al. |
| 2005/0283330 A1 | 12/2005 | Laraia et al. |
| 2006/0004834 A1 | 1/2006 | Pyhalammi et al. |
| 2006/0023945 A1 | 2/2006 | King et al. |
| 2006/0104451 A1 | 5/2006 | Browning et al. |
| 2006/0147058 A1 | 7/2006 | Wang |
| 2006/0190269 A1 | 8/2006 | Tessel et al. |
| 2006/0190968 A1 | 8/2006 | Jung et al. |
| 2006/0247913 A1 | 11/2006 | Huerta et al. |
| 2006/0262943 A1 | 11/2006 | Oxford |
| 2007/0018844 A1 | 1/2007 | Sutardja |
| 2007/0019815 A1 | 1/2007 | Asada et al. |
| 2007/0033043 A1 | 2/2007 | Hyakumoto |
| 2007/0071255 A1 | 3/2007 | Schobben |
| 2007/0076131 A1 | 4/2007 | Li et al. |
| 2007/0076906 A1 | 4/2007 | Takagi et al. |
| 2007/0140058 A1 | 6/2007 | McIntosh et al. |
| 2007/0140521 A1 | 6/2007 | Mitobe et al. |
| 2007/0142944 A1 | 6/2007 | Goldberg et al. |
| 2007/0147651 A1 | 6/2007 | Mitobe et al. |
| 2008/0037814 A1 | 2/2008 | Shau |
| 2008/0090537 A1 | 4/2008 | Sutardja |
| 2008/0146289 A1 | 6/2008 | Korneluk et al. |
| 2008/0208594 A1 | 8/2008 | Cross et al. |
| 2008/0221897 A1 | 9/2008 | Cerra et al. |
| 2008/0247530 A1 | 10/2008 | Barton et al. |
| 2008/0248797 A1 | 10/2008 | Freeman et al. |
| 2008/0301729 A1 | 12/2008 | Broos et al. |
| 2009/0003620 A1 | 1/2009 | McKillop et al. |
| 2009/0005893 A1 | 1/2009 | Sugii et al. |
| 2009/0010445 A1 | 1/2009 | Matsuo et al. |
| 2009/0018828 A1 | 1/2009 | Nakadai et al. |
| 2009/0052688 A1 | 2/2009 | Ishibashi et al. |
| 2009/0076821 A1 | 3/2009 | Brenner et al. |
| 2009/0153289 A1 | 6/2009 | Hope et al. |
| 2009/0197524 A1 | 8/2009 | Haff et al. |
| 2009/0220107 A1 | 9/2009 | Every et al. |
| 2009/0228919 A1 | 9/2009 | Zott et al. |
| 2009/0238377 A1 | 9/2009 | Ramakrishnan et al. |
| 2009/0248397 A1 | 10/2009 | Garcia et al. |
| 2009/0264072 A1 | 10/2009 | Dai |
| 2009/0323907 A1 | 12/2009 | Gupta et al. |
| 2009/0326949 A1 | 12/2009 | Douthitt et al. |
| 2010/0014690 A1 | 1/2010 | Wolff et al. |
| 2010/0023638 A1 | 1/2010 | Bowman |
| 2010/0035593 A1 | 2/2010 | Franco et al. |
| 2010/0070922 A1 | 3/2010 | Demaio et al. |
| 2010/0075723 A1 | 3/2010 | Min et al. |
| 2010/0092004 A1 | 4/2010 | Kuze |
| 2010/0172516 A1 | 7/2010 | Lastrucci |
| 2010/0178873 A1 | 7/2010 | Lee et al. |
| 2010/0179874 A1 | 7/2010 | Higgins et al. |
| 2010/0185448 A1 | 7/2010 | Meisel |
| 2010/0211199 A1 | 8/2010 | Naik et al. |
| 2011/0033059 A1 | 2/2011 | Bhaskar et al. |
| 2011/0035580 A1 | 2/2011 | Wang et al. |
| 2011/0044461 A1 | 2/2011 | Kuech et al. |
| 2011/0044489 A1 | 2/2011 | Saiki et al. |
| 2011/0066634 A1 | 3/2011 | Phillips et al. |
| 2011/0091055 A1 | 4/2011 | Leblanc |
| 2011/0103615 A1 | 5/2011 | Sun |
| 2011/0145581 A1 | 6/2011 | Malhotra et al. |
| 2011/0170707 A1 | 7/2011 | Yamada et al. |
| 2011/0182436 A1 | 7/2011 | Murgia et al. |
| 2011/0267985 A1 | 11/2011 | Wilkinson et al. |
| 2011/0276333 A1 | 11/2011 | Wang et al. |
| 2011/0280422 A1 | 11/2011 | Neumeyer et al. |
| 2011/0289506 A1 | 11/2011 | Trivi et al. |
| 2011/0299706 A1 | 12/2011 | Sakai |
| 2012/0020486 A1 | 1/2012 | Fried et al. |
| 2012/0022863 A1 | 1/2012 | Cho et al. |
| 2012/0022864 A1 | 1/2012 | Leman et al. |
| 2012/0078635 A1 | 3/2012 | Rothkopf et al. |
| 2012/0123268 A1 | 5/2012 | Tanaka et al. |
| 2012/0128160 A1 | 5/2012 | Kim et al. |
| 2012/0131125 A1 | 5/2012 | Seidel et al. |
| 2012/0148075 A1 | 6/2012 | Goh et al. |
| 2012/0163603 A1 | 6/2012 | Abe et al. |
| 2012/0177215 A1 | 7/2012 | Bose et al. |
| 2012/0297284 A1 | 11/2012 | Matthews, III et al. |

(56) References Cited

U.S. PATENT DOCUMENTS

| | | |
|---|---|---|
| 2012/0308044 A1 | 12/2012 | Vander Mey et al. |
| 2012/0308046 A1 | 12/2012 | Muza |
| 2013/0006453 A1 | 1/2013 | Wang et al. |
| 2013/0024018 A1 | 1/2013 | Chang et al. |
| 2013/0034241 A1 | 2/2013 | Pandey et al. |
| 2013/0039527 A1 | 2/2013 | Jensen et al. |
| 2013/0058492 A1 | 3/2013 | Silzle et al. |
| 2013/0066453 A1 | 3/2013 | Seefeldt |
| 2013/0080146 A1 | 3/2013 | Kato et al. |
| 2013/0124211 A1 | 5/2013 | McDonough |
| 2013/0148821 A1 | 6/2013 | Sorensen |
| 2013/0179173 A1 | 7/2013 | Lee et al. |
| 2013/0183944 A1 | 7/2013 | Mozer et al. |
| 2013/0191122 A1 | 7/2013 | Mason |
| 2013/0198298 A1 | 8/2013 | Li et al. |
| 2013/0216056 A1 | 8/2013 | Thyssen |
| 2013/0315420 A1 | 11/2013 | You |
| 2013/0317635 A1 | 11/2013 | Bates et al. |
| 2013/0322665 A1 | 12/2013 | Bennett et al. |
| 2013/0324031 A1 | 12/2013 | Loureiro |
| 2013/0329896 A1 | 12/2013 | Krishnaswamy et al. |
| 2013/0331970 A1 | 12/2013 | Beckhardt et al. |
| 2013/0332165 A1 | 12/2013 | Beckley et al. |
| 2013/0339028 A1 | 12/2013 | Rosner et al. |
| 2014/0003611 A1 | 1/2014 | Mohammad et al. |
| 2014/0003625 A1 | 1/2014 | Sheen et al. |
| 2014/0003635 A1 | 1/2014 | Mohammad et al. |
| 2014/0006026 A1 | 1/2014 | Lamb et al. |
| 2014/0034929 A1 | 2/2014 | Hamada et al. |
| 2014/0046464 A1 | 2/2014 | Reimann |
| 2014/0064501 A1 | 3/2014 | Olsen et al. |
| 2014/0075306 A1 | 3/2014 | Rega |
| 2014/0094151 A1 | 4/2014 | Klappert et al. |
| 2014/0100854 A1 | 4/2014 | Chen et al. |
| 2014/0122075 A1 | 5/2014 | Bak et al. |
| 2014/0136195 A1 | 5/2014 | Abdossalami et al. |
| 2014/0145168 A1 | 5/2014 | Ohsawa et al. |
| 2014/0146983 A1 | 5/2014 | Kim et al. |
| 2014/0163978 A1 | 6/2014 | Basye et al. |
| 2014/0164400 A1 | 6/2014 | Kruglick |
| 2014/0167931 A1 | 6/2014 | Lee et al. |
| 2014/0168344 A1 | 6/2014 | Shoemake et al. |
| 2014/0172953 A1 | 6/2014 | Blanksteen |
| 2014/0195252 A1 | 7/2014 | Gruber et al. |
| 2014/0219472 A1 | 8/2014 | Huang et al. |
| 2014/0222436 A1 | 8/2014 | Binder et al. |
| 2014/0244013 A1 | 8/2014 | Reilly |
| 2014/0244712 A1 | 8/2014 | Walters et al. |
| 2014/0249817 A1 | 9/2014 | Hart et al. |
| 2014/0252386 A1 | 9/2014 | Ito et al. |
| 2014/0254805 A1 | 9/2014 | Su et al. |
| 2014/0258292 A1 | 9/2014 | Thramann et al. |
| 2014/0259075 A1 | 9/2014 | Chang et al. |
| 2014/0270282 A1 | 9/2014 | Tammi et al. |
| 2014/0274185 A1 | 9/2014 | Luna et al. |
| 2014/0274203 A1 | 9/2014 | Ganong, III et al. |
| 2014/0274218 A1 | 9/2014 | Kadiwala et al. |
| 2014/0277650 A1 | 9/2014 | Zurek et al. |
| 2014/0291642 A1 | 10/2014 | Watabe et al. |
| 2014/0310002 A1 | 10/2014 | Nitz et al. |
| 2014/0310614 A1 | 10/2014 | Jones |
| 2014/0340888 A1 | 11/2014 | Ishisone et al. |
| 2014/0357248 A1 | 12/2014 | Tonshal et al. |
| 2014/0363022 A1 | 12/2014 | Dizon et al. |
| 2014/0363024 A1 | 12/2014 | Apodaca |
| 2014/0365227 A1 | 12/2014 | Cash et al. |
| 2014/0369491 A1 | 12/2014 | Kloberdans et al. |
| 2014/0372109 A1 | 12/2014 | Iyer et al. |
| 2015/0006176 A1 | 1/2015 | Pogue et al. |
| 2015/0006184 A1 | 1/2015 | Marti et al. |
| 2015/0010169 A1 | 1/2015 | Popova et al. |
| 2015/0014680 A1 | 1/2015 | Yamazaki et al. |
| 2015/0016642 A1 | 1/2015 | Walsh et al. |
| 2015/0019201 A1 | 1/2015 | Schoenbach |
| 2015/0036831 A1 | 2/2015 | Klippel |
| 2015/0063580 A1 | 3/2015 | Huang et al. |
| 2015/0086034 A1 | 3/2015 | Lombardi et al. |
| 2015/0091709 A1 | 4/2015 | Reichert et al. |
| 2015/0092947 A1 | 4/2015 | Gossain et al. |
| 2015/0104037 A1 | 4/2015 | Lee et al. |
| 2015/0106085 A1 | 4/2015 | Lindahl |
| 2015/0110294 A1 | 4/2015 | Chen et al. |
| 2015/0112672 A1 | 4/2015 | Giacobello et al. |
| 2015/0128065 A1 | 5/2015 | Torii et al. |
| 2015/0154976 A1 | 6/2015 | Mutagi |
| 2015/0169279 A1 | 6/2015 | Duga |
| 2015/0170645 A1 | 6/2015 | Di Censo et al. |
| 2015/0180432 A1 | 6/2015 | Gao et al. |
| 2015/0181318 A1 | 6/2015 | Gautama et al. |
| 2015/0189438 A1 | 7/2015 | Hampiholi et al. |
| 2015/0200454 A1 | 7/2015 | Heusdens et al. |
| 2015/0221678 A1 | 8/2015 | Yamazaki et al. |
| 2015/0222563 A1 | 8/2015 | Burns et al. |
| 2015/0222987 A1 | 8/2015 | Angel, Jr. et al. |
| 2015/0228274 A1 | 8/2015 | Leppänen et al. |
| 2015/0228803 A1 | 8/2015 | Koezuka et al. |
| 2015/0237406 A1 | 8/2015 | Ochoa et al. |
| 2015/0245152 A1 | 8/2015 | Ding et al. |
| 2015/0249889 A1 | 9/2015 | Iyer et al. |
| 2015/0253292 A1 | 9/2015 | Larkin et al. |
| 2015/0253960 A1 | 9/2015 | Lin et al. |
| 2015/0263174 A1 | 9/2015 | Yamazaki et al. |
| 2015/0271593 A1 | 9/2015 | Sun et al. |
| 2015/0277846 A1 | 10/2015 | Yen et al. |
| 2015/0280676 A1 | 10/2015 | Holman et al. |
| 2015/0296299 A1 | 10/2015 | Klippel et al. |
| 2015/0302856 A1 | 10/2015 | Kim et al. |
| 2015/0319529 A1 | 11/2015 | Klippel |
| 2015/0325267 A1 | 11/2015 | Lee et al. |
| 2015/0338917 A1 | 11/2015 | Steiner et al. |
| 2015/0341406 A1 | 11/2015 | Rockefeller et al. |
| 2015/0346845 A1 | 12/2015 | Di Censo et al. |
| 2015/0348551 A1 | 12/2015 | Gruber et al. |
| 2015/0363061 A1 | 12/2015 | De Nigris, III et al. |
| 2015/0363401 A1 | 12/2015 | Chen et al. |
| 2015/0371657 A1 | 12/2015 | Gao |
| 2015/0371664 A1 | 12/2015 | Bar-Or et al. |
| 2015/0380010 A1 | 12/2015 | Srinivasan et al. |
| 2016/0007116 A1 | 1/2016 | Holman |
| 2016/0021458 A1 | 1/2016 | Johnson et al. |
| 2016/0026428 A1 | 1/2016 | Morganstern et al. |
| 2016/0029142 A1 | 1/2016 | Isaac et al. |
| 2016/0035321 A1 | 2/2016 | Cho et al. |
| 2016/0036962 A1 | 2/2016 | Rand et al. |
| 2016/0042748 A1 | 2/2016 | Jain et al. |
| 2016/0044151 A1 | 2/2016 | Shoemaker et al. |
| 2016/0050488 A1 | 2/2016 | Matheja et al. |
| 2016/0057522 A1 | 2/2016 | Choisel et al. |
| 2016/0077710 A1 | 3/2016 | Lewis et al. |
| 2016/0088036 A1 | 3/2016 | Corbin et al. |
| 2016/0088392 A1 | 3/2016 | Huttunen et al. |
| 2016/0093304 A1 | 3/2016 | Kim et al. |
| 2016/0094917 A1 | 3/2016 | Wilk et al. |
| 2016/0098393 A1 | 4/2016 | Hebert |
| 2016/0098992 A1 | 4/2016 | Renard et al. |
| 2016/0103653 A1 | 4/2016 | Jang |
| 2016/0104480 A1 | 4/2016 | Sharifi |
| 2016/0111110 A1 | 4/2016 | Gautama et al. |
| 2016/0127780 A1 | 5/2016 | Roberts et al. |
| 2016/0133259 A1 | 5/2016 | Rubin et al. |
| 2016/0134982 A1 | 5/2016 | Iyer |
| 2016/0155442 A1 | 6/2016 | Kannan et al. |
| 2016/0155443 A1 | 6/2016 | Khan et al. |
| 2016/0157035 A1 | 6/2016 | Russell et al. |
| 2016/0162469 A1 | 6/2016 | Santos |
| 2016/0173578 A1 | 6/2016 | Sharma et al. |
| 2016/0173983 A1 | 6/2016 | Berthelsen et al. |
| 2016/0180853 A1 | 6/2016 | Vanlund et al. |
| 2016/0189716 A1 | 6/2016 | Lindahl et al. |
| 2016/0196499 A1 | 7/2016 | Khan et al. |
| 2016/0203331 A1 | 7/2016 | Khan et al. |
| 2016/0212538 A1 | 7/2016 | Fullam et al. |
| 2016/0225385 A1 | 8/2016 | Hammarqvist |
| 2016/0232451 A1 | 8/2016 | Scherzer |

(56) References Cited

U.S. PATENT DOCUMENTS

| | | |
|---|---|---|
| 2016/0234204 A1 | 8/2016 | Rishi et al. |
| 2016/0239255 A1 | 8/2016 | Chavez et al. |
| 2016/0260431 A1 | 9/2016 | Newendorp et al. |
| 2016/0302018 A1 | 10/2016 | Russell et al. |
| 2016/0314782 A1 | 10/2016 | Klimanis |
| 2016/0336519 A1 | 11/2016 | Seo et al. |
| 2016/0343866 A1 | 11/2016 | Koezuka et al. |
| 2016/0343949 A1 | 11/2016 | Seo et al. |
| 2016/0343954 A1 | 11/2016 | Seo et al. |
| 2016/0345114 A1 | 11/2016 | Hanna et al. |
| 2016/0352915 A1 | 12/2016 | Gautama |
| 2016/0353218 A1 | 12/2016 | Starobin et al. |
| 2016/0357503 A1 | 12/2016 | Triplett et al. |
| 2016/0366515 A1 | 12/2016 | Mendes et al. |
| 2016/0372688 A1 | 12/2016 | Seo et al. |
| 2016/0373269 A1 | 12/2016 | Okubo et al. |
| 2016/0373909 A1 | 12/2016 | Rasmussen et al. |
| 2016/0379634 A1 | 12/2016 | Yamamoto et al. |
| 2017/0003931 A1 | 1/2017 | Dvortsov et al. |
| 2017/0012207 A1 | 1/2017 | Seo et al. |
| 2017/0012232 A1 | 1/2017 | Kataishi et al. |
| 2017/0019732 A1 | 1/2017 | Mendes et al. |
| 2017/0025615 A1 | 1/2017 | Seo et al. |
| 2017/0025630 A1 | 1/2017 | Seo et al. |
| 2017/0026769 A1 | 1/2017 | Patel |
| 2017/0039025 A1 | 2/2017 | Kielak |
| 2017/0060526 A1 | 3/2017 | Barton et al. |
| 2017/0062734 A1 | 3/2017 | Suzuki et al. |
| 2017/0070478 A1 | 3/2017 | Park et al. |
| 2017/0076720 A1 | 3/2017 | Gopalan et al. |
| 2017/0078824 A1 | 3/2017 | Heo |
| 2017/0083285 A1 | 3/2017 | Meyers et al. |
| 2017/0084292 A1 | 3/2017 | Yoo |
| 2017/0084295 A1 | 3/2017 | Tsiartas et al. |
| 2017/0090864 A1 | 3/2017 | Jorgovanovic |
| 2017/0092278 A1 | 3/2017 | Evermann et al. |
| 2017/0092297 A1 | 3/2017 | Sainath et al. |
| 2017/0092299 A1 | 3/2017 | Matsuo |
| 2017/0092889 A1 | 3/2017 | Seo et al. |
| 2017/0092890 A1 | 3/2017 | Seo et al. |
| 2017/0103754 A1 | 4/2017 | Higbie et al. |
| 2017/0103755 A1 | 4/2017 | Jeon et al. |
| 2017/0110124 A1 | 4/2017 | Boesen et al. |
| 2017/0110144 A1 | 4/2017 | Sharifi et al. |
| 2017/0117497 A1 | 4/2017 | Seo et al. |
| 2017/0123251 A1 | 5/2017 | Nakada et al. |
| 2017/0125037 A1 | 5/2017 | Shin |
| 2017/0125456 A1 | 5/2017 | Kasahara |
| 2017/0134872 A1 | 5/2017 | Silva et al. |
| 2017/0139720 A1 | 5/2017 | Stein |
| 2017/0140748 A1 | 5/2017 | Roberts et al. |
| 2017/0140759 A1 | 5/2017 | Kumar et al. |
| 2017/0177585 A1 | 6/2017 | Rodger et al. |
| 2017/0178662 A1 | 6/2017 | Ayrapetian et al. |
| 2017/0180561 A1 | 6/2017 | Kadiwala et al. |
| 2017/0188150 A1 | 6/2017 | Brunet et al. |
| 2017/0193999 A1 | 7/2017 | Aleksic et al. |
| 2017/0206896 A1 | 7/2017 | Ko et al. |
| 2017/0206900 A1 | 7/2017 | Lee et al. |
| 2017/0214996 A1 | 7/2017 | Yeo |
| 2017/0236512 A1* | 8/2017 | Williams ............... G06F 16/68 381/79 |
| 2017/0236515 A1 | 8/2017 | Pinsky et al. |
| 2017/0242649 A1 | 8/2017 | Jarvis et al. |
| 2017/0242651 A1 | 8/2017 | Lang et al. |
| 2017/0242653 A1 | 8/2017 | Lang et al. |
| 2017/0243587 A1 | 8/2017 | Plagge et al. |
| 2017/0245076 A1 | 8/2017 | Kusano et al. |
| 2017/0257686 A1 | 9/2017 | Gautama et al. |
| 2017/0270919 A1 | 9/2017 | Parthasarathi et al. |
| 2017/0287485 A1 | 10/2017 | Civelli et al. |
| 2017/0332168 A1 | 11/2017 | Moghimi et al. |
| 2017/0353789 A1 | 12/2017 | Kim et al. |
| 2017/0357478 A1 | 12/2017 | Piersol et al. |
| 2017/0366393 A1 | 12/2017 | Shaker et al. |
| 2018/0025733 A1 | 1/2018 | Qian et al. |
| 2018/0033428 A1 | 2/2018 | Kim et al. |
| 2018/0040324 A1 | 2/2018 | Wilberding |
| 2018/0047394 A1 | 2/2018 | Tian et al. |
| 2018/0053504 A1 | 2/2018 | Wang et al. |
| 2018/0054506 A1* | 2/2018 | Hart ..................... H04M 1/271 |
| 2018/0061402 A1* | 3/2018 | Devaraj ............... H04L 67/306 |
| 2018/0062871 A1 | 3/2018 | Jones et al. |
| 2018/0084367 A1 | 3/2018 | Greff et al. |
| 2018/0091898 A1 | 3/2018 | Yoon et al. |
| 2018/0091913 A1 | 3/2018 | Hartung et al. |
| 2018/0096683 A1 | 4/2018 | James et al. |
| 2018/0122378 A1 | 5/2018 | Mixter et al. |
| 2018/0130469 A1 | 5/2018 | Gruenstein et al. |
| 2018/0132298 A1 | 5/2018 | Birnam et al. |
| 2018/0137861 A1 | 5/2018 | Ogawa et al. |
| 2018/0165055 A1 | 6/2018 | Yu et al. |
| 2018/0167981 A1 | 6/2018 | Jonna et al. |
| 2018/0199146 A1 | 7/2018 | Sheen |
| 2018/0210698 A1 | 7/2018 | Park et al. |
| 2018/0228006 A1 | 8/2018 | Baker et al. |
| 2018/0233136 A1* | 8/2018 | Torok ..................... G06F 3/165 |
| 2018/0262793 A1 | 9/2018 | Lau et al. |
| 2018/0277113 A1 | 9/2018 | Hartung et al. |
| 2018/0293484 A1 | 10/2018 | Wang et al. |
| 2018/0335903 A1 | 11/2018 | Coffman et al. |
| 2018/0367944 A1 | 12/2018 | Heo et al. |
| 2019/0013019 A1 | 1/2019 | Lawrence |
| 2019/0033446 A1 | 1/2019 | Bultan et al. |
| 2019/0043492 A1 | 2/2019 | Lang |
| 2019/0074025 A1 | 3/2019 | Lashkari et al. |
| 2019/0081507 A1 | 3/2019 | Ide |
| 2019/0088261 A1 | 3/2019 | Lang et al. |
| 2019/0090056 A1 | 3/2019 | Rexach et al. |
| 2019/0098400 A1 | 3/2019 | Buoni et al. |
| 2019/0104373 A1 | 4/2019 | Wodrich et al. |
| 2019/0108839 A1 | 4/2019 | Reilly et al. |
| 2019/0130906 A1 | 5/2019 | Kobayashi et al. |
| 2019/0172452 A1 | 6/2019 | Smith et al. |
| 2019/0173687 A1 | 6/2019 | MacKay et al. |
| 2019/0220246 A1 | 7/2019 | Orr et al. |
| 2019/0237067 A1 | 8/2019 | Friedman et al. |
| 2019/0295563 A1 | 9/2019 | Kamdar et al. |
| 2019/0304443 A1 | 10/2019 | Bhagwan |
| 2019/0311710 A1 | 10/2019 | Eraslan et al. |
| 2020/0175989 A1* | 6/2020 | Lockhart ................ G10L 15/26 |
| 2020/0395006 A1* | 12/2020 | Smith ................... G10L 15/083 |
| 2020/0395010 A1* | 12/2020 | Smith ................. G10L 15/1822 |
| 2020/0395013 A1* | 12/2020 | Smith ..................... G06F 3/165 |
| 2021/0035561 A1* | 2/2021 | D'Amato ............... G10L 15/22 |
| 2021/0035572 A1* | 2/2021 | D'Amato ........... G10L 15/1822 |

FOREIGN PATENT DOCUMENTS

| | | |
|---|---|---|
| CN | 101661753 A | 3/2010 |
| CN | 102256098 A | 11/2011 |
| CN | 103181192 A | 6/2013 |
| CN | 103546616 A | 1/2014 |
| CN | 104010251 A | 8/2014 |
| CN | 104053088 A | 9/2014 |
| CN | 104092936 A | 10/2014 |
| CN | 105284076 A | 1/2016 |
| CN | 107919123 A | 4/2018 |
| EP | 1349146 A1 | 10/2003 |
| EP | 1389853 A1 | 2/2004 |
| EP | 2683147 A1 | 1/2014 |
| EP | 2351021 B1 | 9/2017 |
| EP | 3285502 A1 | 2/2018 |
| JP | 2001236093 A | 8/2001 |
| JP | 2003223188 A | 8/2003 |
| JP | 2004347943 A | 12/2004 |
| JP | 2004354721 A | 12/2004 |
| JP | 2005284492 A | 10/2005 |
| JP | 2007013400 A | 1/2007 |
| JP | 2007142595 A | 6/2007 |
| JP | 2008079256 A | 4/2008 |
| JP | 2008158868 A | 7/2008 |
| JP | 2010141748 A | 6/2010 |
| JP | 2013037148 A | 2/2013 |

(56) References Cited

FOREIGN PATENT DOCUMENTS

| | | |
|---|---|---|
| JP | 2014071138 A | 4/2014 |
| JP | 2014137590 A | 7/2014 |
| JP | 2015161551 A | 9/2015 |
| KR | 20100111071 A | 10/2010 |
| WO | 200153994 | 7/2001 |
| WO | 2003093950 A2 | 11/2003 |
| WO | 2015037396 A1 | 3/2015 |
| WO | 2015178950 A1 | 11/2015 |
| WO | 2016014142 A1 | 1/2016 |
| WO | 2016022926 A1 | 2/2016 |
| WO | 2016033364 A1 | 3/2016 |
| WO | 2016057268 A1 | 4/2016 |
| WO | 2017039632 A1 | 3/2017 |
| WO | 2018027142 A1 | 2/2018 |
| WO | 2018067404 A1 | 4/2018 |

OTHER PUBLICATIONS

Advisory Action dated Jun. 28, 2018, issued in connection with U.S. Appl. No. 15/438,744, filed Feb. 21, 2017, 3 pages.
Advisory Action dated Dec. 31, 2018, issued in connection with U.S. Appl. No. 15/804,776, filed Nov. 6, 2017, 4 pages.
AudioTron Quick Start Guide, Version 1.0, Mar. 2001, 24 pages.
AudioTron Reference Manual, Version 3.0, May 2002, 70 pages.
AudioTron Setup Guide, Version 3.0, May 2002, 38 pages.
Australian Patent Office, Australian Examination Report Action dated Oct. 3, 2019, issued in connection with Australian Application No. 2018230932, 3 pages.
Australian Patent Office, Examination Report dated Oct. 30, 2018, issued in connection with Australian Application No. 2017222436, 3 pages.
"Automatic Parameter Tying in Neural Networks" ICLR 2018, 14 pages.
Bluetooth. "Specification of the Bluetooth System: The ad hoc Scatternet for affordable and highly functional wireless connectivity," Core, Version 1.0 A, Jul. 26, 1999, 1068 pages.
Bluetooth. "Specification of the Bluetooth System: Wireless connections made easy," Core, Version 1.0 B, Dec. 1, 1999, 1076 pages.
Canadian Patent Office, Canadian Office Action dated Nov. 14, 2018, issued in connection with Canadian Application No. 3015491, 3 pages.
Chinese Patent Office, First Office Action and Translation dated Mar. 20, 2019, issued in connection with Chinese Application No. 201780025028.2, 18 pages.
Chinese Patent Office, First Office Action and Translation dated Mar. 27, 2019, issued in connection with Chinese Application No. 201780025029.7, 9 pages.
Chinese Patent Office, First Office Action and Translation dated Nov. 5, 2019, issued in connection with Chinese Application No. 201780072651.3, 19 pages.
Chinese Patent Office, Second Office Action and Translation dated Jul. 18, 2019, issued in connection with Chinese Application No. 201780025029.7, 14 pages.
Chinese Patent Office, Second Office Action and Translation dated Sep. 23, 2019, issued in connection with Chinese Application No. 201780025028.2, 15 pages.
Chinese Patent Office, Third Office Action and Translation dated Sep. 16, 2019, issued in connection with Chinese Application No. 201780025029.7, 14 pages.
Chinese Patent Office, Translation of Office Action dated Jul. 18, 2019, issued in connection with Chinese Application No. 201780025029.7, 8 pages.
Corrected Notice of Allowability dated Mar. 8, 2017, issued in connection with U.S. Appl. No. 15/229,855, filed Aug. 5, 2016, 6 pages.
Dell, Inc. "Dell Digital Audio Receiver: Reference Guide," Jun. 2000, 70 pages.
Dell, Inc. "Start Here," Jun. 2000, 2 pages.
"Denon 2003-2004 Product Catalog," Denon, 2003-2004, 44 pages.

European Patent Office, European Extended Search Report dated Jan. 3, 2019, issued in connection with European Application No. 177570702, 8 pages.
European Patent Office, European Extended Search Report dated Jan. 3, 2019, issued in connection with European Application No. 17757075.1, 9 pages.
European Patent Office, European Extended Search Report dated Oct. 30, 2017, issued in connection with EP Application No. 17174435.2, 11 pages.
European Patent Office, European Office Action dated Jan. 22, 2019, issued in connection with European Application No. 17174435.2, 9 pages.
European Patent Office, European Office Action dated Aug. 30, 2019, issued in connection with European Application No. 17781608.9, 6 pages.
European Patent Office, Summons to Attend Oral Proceedings mailed on Dec. 20, 2019, issued in connection with European Application No. 17174435.2, 13 pages.
Fadilpasic,"Cortana can now be the default PDA on your Android", IT Pro Portal: Accessed via WayBack Machine; http://web.archive.org/web/20171129124915/https://www.itproportal.com/2015/08/11/cortana-can-now-be- . . . , Aug. 11, 2015, 6 pages.
Final Office Action dated Oct. 6, 2017, issued in connection with U.S. Appl. No. 15/098,760, filed Apr. 14, 2016, 25 pages.
Final Office Action dated Apr. 11, 2019, issued in connection with U.S. Appl. No. 15/131,254, filed Apr. 18, 2016, 17 pages.
Final Office Action dated Aug. 11, 2017, issued in connection with U.S. Appl. No. 15/131,776, filed Apr. 18, 2016, 7 pages.
Final Office Action dated Dec. 11, 2019, issued in connection with U.S. Appl. No. 16/227,308, filed Dec. 20, 2018, 10 pages.
Final Office Action dated Sep. 11, 2019, issued in connection with U.S. Appl. No. 16/178,122, filed Nov. 1, 2018, 13 pages.
Final Office Action dated Apr. 13, 2018, issued in connection with U.S. Appl. No. 15/131,254, filed Apr. 18, 2016, 18 pages.
Final Office Action dated Apr. 13, 2018, issued in connection with U.S. Appl. No. 15/438,744, filed Feb. 21, 2017, 20 pages.
Final Office Action dated Jun. 15, 2017, issued in connection with U.S. Appl. No. 15/098,718, filed Apr. 14, 2016, 15 pages.
Final Office Action dated Oct. 15, 2018, issued in connection with U.S. Appl. No. 15/804,776, filed Nov. 6, 2017, 18 pages.
Final Office Action dated Oct. 16, 2018, issued in connection with U.S. Appl. No. 15/438,725, filed Feb. 21, 2017, 10 pages.
Final Office Action dated Feb. 21, 2018, issued in connection with U.S. Appl. No. 15/297,627, filed Oct. 19, 2016, 12 pages.
Final Office Action dated Apr. 26, 2019, issued in connection with U.S. Appl. No. 15/721,141, filed Sep. 29, 2017, 20 pages.
Final Office Action dated Apr. 30, 2019, issued in connection with U.S. Appl. No. 15/098,760, filed Apr. 14, 2016, 6 pages.
Final Office Action dated Feb. 5, 2019, issued in connection with U.S. Appl. No. 15/438,749, filed Feb. 21, 2017, 17 pages.
Fiorenza Arisio et al. "Deliverable 1.1 User Study, analysis of requirements and definition of the application task," May 31, 2012, http://dirha.fbk.eu/sites/dirha.fbk.eu/files/docs/DIRHA_D1.1., 31 pages.
First Action Interview Office Action dated Aug. 14, 2019, issued in connection with U.S. Appl. No. 16/227,308, filed Dec. 20, 2018, 4 pages.
First Action Interview Office Action dated Jul. 5, 2019, issued in connection with U.S. Appl. No. 16/227,308, filed Dec. 20, 2018, 4 pages.
Freiberger, Karl, "Development and Evaluation of Source Localization Algorithms for Coincident Microphone Arrays," Diploma Thesis, Apr. 1, 2010, 106 pages.
Giacobello et al. "A Sparse Nonuniformly Partitioned Multidelay Filter for Acoustic Echo Cancellation," 2013, IEEE Workshop on Applications of Signal Processing to Audio and Acoustics, Oct. 2013, New Paltz, NY, 4 pages.
Giacobello et al. "Tuning Methodology for Speech Enhancement Algorithms using a Simulated Conversational Database and Perceptual Objective Measures," 2014, 4th Joint Workshop on Hands-free Speech Communication and Microphone Arrays HSCMA, 2014, 5 pages.

(56) References Cited

OTHER PUBLICATIONS

Han et al. "Deep Compression: Compressing Deep Neural Networks with Pruning, Trained Quantization and Huffman Coding." ICLR 2016, Feb. 15, 2016, 14 pages.
Helwani et al "Source-domain adaptive filtering for MIMO systems with application to acoustic echo cancellation", Acoustics Speech and Signal Processing, 2010 IEEE International Conference, Mar. 14, 2010, 4 pages.
Hirano et al. "A Noise-Robust Stochastic Gradient Algorithm with an Adaptive Step-Size Suitable for Mobile Hands-Free Telephones," 1995, International Conference on Acoustics, Speech, and Signal Processing, vol. 2, 4 pages.
International Bureau, International Preliminary Report on Patentability, dated Apr. 11, 2019, issued in connection with International Application No. PCT/US2017/0054063, filed on Sep. 28, 2017, 9 pages.
International Bureau, International Preliminary Report on Patentability, dated Apr. 23, 2019, issued in connection with International Application No. PCT/US2017/057220, filed on Oct. 18, 2017, 7 pages.
International Bureau, International Preliminary Report on Patentability, dated Sep. 7, 2018, issued in connection with International Application No. PCT/US2017/018728, filed on Feb. 21, 2017, 8 pages.
International Bureau, International Preliminary Report on Patentability, dated Sep. 7, 2018, issued in connection with International Application No. PCT/US2017/018739, filed on Feb. 21, 2017, 7 pages.
International Bureau, International Search Report and Written Opinion dated Nov. 18, 2019, issued in connection with International Application No. PCT/US2019052841, filed on Sep. 25, 2019, 12 pages.
International Bureau, International Search Report and Written Opinion dated Dec. 20, 2019, issued in connection with International Application No. PCT/US2019052654, filed on Sep. 24, 2019, 11 pages.
International Bureau, International Search Report and Written Opinion dated Dec. 6, 2019, issued in connection with International Application No. PCT/US2019050852, filed on Sep. 12, 2019, 10 pages.
International Searching Authority, International Search Report and Written Opinion dated Dec. 19, 2018, in connection with International Application No. PCT/US2018/053517, 13 pages.
International Searching Authority, International Search Report and Written Opinion dated Nov. 22, 2017, issued in connection with International Application No. PCT/US2017/054063, filed on Sep. 28, 2017, 11 pages.
International Searching Authority, International Search Report and Written Opinion dated Jan. 23, 2018, issued in connection with International Application No. PCT/US2017/57220, filed on Oct. 18, 2017, 8 pages.
International Searching Authority, International Search Report and Written Opinion dated May 23, 2017, issued in connection with International Application No. PCT/US2017/018739, Filed on Feb. 21, 2017, 10 pages.
International Searching Authority, International Search Report and Written Opinion dated Oct. 23, 2017, issued in connection with International Application No. PCT/US2017/042170, filed on Jul. 14, 2017, 15 pages.
International Searching Authority, International Search Report and Written Opinion dated Oct. 24, 2017, issued in connection with International Application No. PCT/US2017/042227, filed on Jul. 14, 2017, 16 pages.
International Searching Authority, International Search Report and Written Opinion dated May 30, 2017, issued in connection with International Application No. PCT/US2017/018728, Filed on Feb. 21, 2017, 11 pages.
Japanese Patent Office, Non-Final Office Action and Translation dated Nov. 5, 2019, issued in connection with Japanese Patent Application No. 2019-517281, 6 pages.
Japanese Patent Office, Office Action and Translation dated Oct. 8, 2019, issued in connection with Japanese Patent Application No. 2019-521032, 5 pages.
Japanese Patent Office, Office Action Translation dated Nov. 5, 2019, issued in connection with Japanese Patent Application No. 2019-517281, 2 pages.
Japanese Patent Office, Office Action Translation dated Oct. 8, 2019, issued in connection with Japanese Patent Application No. 2019-521032, 8 pages.
Jo et al., "Synchronized One-to-many Media Streaming with Adaptive Playout Control," Proceedings of SPIE, 2002, pp. 71-82, vol. 4861.
Jones, Stephen, "Dell Digital Audio Receiver: Digital upgrade for your analog stereo," Analog Stereo, Jun. 24, 2000 retrieved Jun. 18, 2014, 2 pages.
Jose Alvarez and Mathieu Salzmann "Compression-aware Training of Deep Networks" 31st Conference on Neural Information Processing Systems, Nov. 13, 2017, 12pages.
Korean Patent Office, Korean Office Action and Translation dated Aug. 16, 2019, issued in connection with Korean Application No. 10-2018-7027452, 14 pages.
Korean Patent Office, Korean Office Action and Translation dated Sep. 9, 2019, issued in connection with Korean Application No. 10-2018-7027451, 21 pages.
Korean Patent Office, Korean Office Action dated May 8, 2019, issued in connection with Korean Application No. 10-2018-7027451, 7 pages.
Korean Patent Office, Korean Office Action dated May 8, 2019, issued in connection with Korean Application No. 10-2018-7027452, 5 pages.
Louderback, Jim, "Affordable Audio Receiver Furnishes Homes With MP3," TechTV Vault. Jun. 28, 2000 retrieved Jul. 10, 2014, 2 pages.
Maja Taseska and Emanual A.P. Habets, "MMSE-Based Blind Source Extraction in Diffuse Noise Fields Using a Complex Coherence-Based a Priori Sap Estimator." International Workshop on Acoustic Signal Enhancement 2012, Sep. 4-6, 2012, 4pages.
Morales-Cordovilla et al. "Room Localization for Distant Speech Recognition," Proceedings of Interspeech 2014, Sep. 14, 2014, 4 pages.
Newman, Jared. "Chromecast Audio's multi-room support has arrived," Dec. 11, 2015, https://www.pcworld.com/article/3014204/customer-electronic/chromcase-audio-s-multi-room-support-has . . . , 1 page.
Ngo et al. "Incorporating the Conditional Speech Presence Probability in Multi-Channel Wiener Filter Based Noise Reduction in Hearing Aids." EURASIP Journal on Advances in Signal Processing vol. 2009, Jun. 2, 2009, 11 pages.
Non-Final Office Action dated Jun. 1, 2017, issued in connection with U.S. Appl. No. 15/223,218, filed Jul. 29, 2016, 7 pages.
Non-Final Office Action dated Nov. 2, 2017, issued in connection with U.S. Appl. No. 15/584,782, filed May 2, 2017, 11 pages.
Non-Final Office Action dated Nov. 3, 2017, issued in connection with U.S. Appl. No. 15/438,741, filed Feb. 21, 2017, 11 pages.
Non-Final Office Action dated Nov. 4, 2019, issued in connection with U.S. Appl. No. 16/022,662, filed Jun. 28, 2018, 16 pages.
Non-Final Office Action dated Sep. 5, 2019, issued in connection with U.S. Appl. No. 16/416,752, filed May 20, 2019, 14 pages.
Non-Final Office Action dated Feb. 7, 2017, issued in connection with U.S. Appl. No. 15/131,244, filed Apr. 18, 2016, 12 pages.
Non-Final Office Action dated Feb. 8, 2017, issued in connection with U.S. Appl. No. 15/098,892, filed Apr. 14, 2016, 17 pages.
Non-Final Office Action dated Mar. 9, 2017, issued in connection with U.S. Appl. No. 15/098,760, filed Apr. 14, 2016, 13 pages.
Non-Final Office Action dated Oct. 9, 2019, issued in connection with U.S. Appl. No. 15/936,177, filed Mar. 26, 2018, 16 pages.
Non-Final Office Action dated Jan. 10, 2018, issued in connection with U.S. Appl. No. 15/098,718, filed Apr. 14, 2016, 15 pages.
Non-Final Office Action dated Jan. 10, 2018, issued in connection with U.S. Appl. No. 15/229,868, filed Aug. 5, 2016, 13 pages.
Non-Final Office Action dated Jan. 10, 2018, issued in connection with U.S. Appl. No. 15/438,725, filed Feb. 21, 2017, 15 pages.

(56) References Cited

OTHER PUBLICATIONS

Non-Final Office Action dated Sep. 10, 2018, issued in connection with U.S. Appl. No. 15/670,361, filed Aug. 7, 2017, 17 pages.
Non-Final Office Action dated Oct. 11, 2019, issued in connection with U.S. Appl. No. 16/177,185, filed Oct. 31, 2018, 14 pages.
Non-Final Office Action dated Dec. 12, 2016, issued in connection with U.S. Appl. No. 15/098,718, filed Apr. 14, 2016, 11 pages.
Non-Final Office Action dated Feb. 12, 2019, issued in connection with U.S. Appl. No. 15/670,361, filed Aug. 7, 2017, 13 pages.
Non-Final Office Action dated Jan. 13, 2017, issued in connection with U.S. Appl. No. 15/098,805, filed Apr. 14, 2016, 11 pages.
Non-Final Office Action dated Nov. 13, 2018, issued in connection with U.S. Appl. No. 15/717,621, filed Sep. 27, 2017, 23 pages.
Non-Final Office Action dated Nov. 13, 2018, issued in connection with U.S. Appl. No. 16/160,107, filed Oct. 15, 2018, 8 pages.
Non-Final Office Action dated Nov. 13, 2019, issued in connection with U.S. Appl. No. 15/984,073, filed May 18, 2018, 18 pages.
Non-Final Office Action dated Sep. 14, 2017, issued in connection with U.S. Appl. No. 15/178,180, filed Jun. 9, 2016, 16 pages.
Non-Final Office Action dated Sep. 14, 2018, issued in connection with U.S. Appl. No. 15/959,907, filed Apr. 23, 2018, 15 pages.
Non-Final Office Action dated Jan. 15, 2019, issued in connection with U.S. Appl. No. 16/173,797, filed Oct. 29, 2018, 6 pages.
Non-Final Office Action dated Nov. 15, 2019, issued in connection with U.S. Appl. No. 16/153,530, filed Oct. 5, 2018, 17 pages.
Non-Final Office Action dated Mar. 16, 2018, issued in connection with U.S. Appl. No. 15/681,937, filed Aug. 21, 2017, 5 pages.
Non-Final Office Action dated Oct. 16, 2018, issued in connection with U.S. Appl. No. 15/131,254, filed Apr. 18, 2016, 16 pages.
Non-Final Office Action dated Apr. 18, 2018, issued in connection with U.S. Appl. No. 15/811,468, filed Nov. 13, 2017, 14 pages.
Non-Final Office Action dated Jan. 18, 2019, issued in connection with U.S. Appl. No. 15/721,141, filed Sep. 29, 2017, 18 pages.
Non-Final Office Action dated Oct. 18, 2019, issued in connection with U.S. Appl. No. 15/098,760, filed Apr. 14, 2016, 27 pages.
Non-Final Office Action dated Sep. 18, 2019, issued in connection with U.S. Appl. No. 16/179,779, filed Nov. 2, 2018, 14 pages.
Non-Final Office Action dated Apr. 19, 2017, issued in connection with U.S. Appl. No. 15/131,776, filed Apr. 18, 2016, 12 pages.
Non-Final Office Action dated Dec. 19, 2019, issued in connection with U.S. Appl. No. 16/147,710, filed Sep. 29, 2018, 10 pages.
Non-Final Office Action dated Feb. 20, 2018, issued in connection with U.S. Appl. No. 15/211,748, filed Jul. 15, 2016, 31 pages.
Non-Final Office Action dated Jun. 20, 2019, issued in connection with U.S. Appl. No. 15/946,585, filed Apr. 5, 2018, 10 pages.
Non-Final Office Action dated Aug. 21, 2019, issued in connection with U.S. Appl. No. 16/192,126, filed Nov. 15, 2018, 8 pages.
Non-Final Office Action dated Feb. 21, 2019, issued in connection with U.S. Appl. No. 16/214,666, filed Dec. 10, 2018, 12 pages.
Non-Final Office Action dated Oct. 21, 2019, issued in connection with U.S. Appl. No. 15/973,413, filed May 7, 2018, 10 pages.
Non-Final Office Action dated May 22, 2018, issued in connection with U.S. Appl. No. 15/946,599, filed Apr. 5, 2018, 19 pages.
Non-Final Office Action dated May 23, 2019, issued in connection with U.S. Appl. No. 16/154,071, filed Oct. 8, 2018, 36 pages.
Non-Final Office Action dated Aug. 24, 2017, issued in connection with U.S. Appl. No. 15/297,627, filed Oct. 19, 2016, 13 pages.
Non-Final Office Action dated Jul. 24, 2019, issued in connection with U.S. Appl. No. 16/439,009, filed Jun. 12, 2019, 26 pages.
Non-Final Office Action dated Jul. 25, 2017, issued in connection with U.S. Appl. No. 15/273,679, filed Jul. 22, 2016, 11 pages.
Non-Final Office Action dated Dec. 26, 2018, issued in connection with U.S. Appl. No. 16/154,469, filed Oct. 8, 2018, 7 pages.
Non-Final Office Action dated Jan. 26, 2017, issued in connection with U.S. Appl. No. 15/098,867, filed Apr. 14, 2016, 16 pages.
Non-Final Office Action dated Oct. 26, 2017, issued in connection with U.S. Appl. No. 15/438,744, filed Feb. 21, 2017, 12 pages.
Non-Final Office Action dated Jun. 27, 2018, issued in connection with U.S. Appl. No. 15/438,749, filed Feb. 21, 2017, 16 pages.
Non-Final Office Action dated Jun. 27, 2019, issued in connection with U.S. Appl. No. 16/437,437, filed Jun. 11, 2019, 8 pages.
Non-Final Office Action dated Jun. 27, 2019, issued in connection with U.S. Appl. No. 16/437,476, filed Jun. 11, 2019, 8 pages.
Non-Final Office Action dated Oct. 28, 2019, issued in connection with U.S. Appl. No. 16/145,275, filed Sep. 28, 2018, 11 pages.
Non-Final Office Action dated Mar. 29, 2019, issued in connection with U.S. Appl. No. 16/102,650, filed Aug. 13, 2018, 11 pages.
Non-Final Office Action dated Jul. 3, 2019, issued in connection with U.S. Appl. No. 15/948,541, filed Apr. 9, 2018, 7 pages.
Non-Final Office Action dated May 3, 2019, issued in connection with U.S. Appl. No. 16/178,122, filed Nov. 1, 2018, 14 pages.
Non-Final Office Action dated Oct. 3, 2018, issued in connection with U.S. Appl. No. 16/102,153, filed Aug. 13, 2018, 20 pages.
Non-Final Office Action dated Apr. 30, 2019, issued in connection with U.S. Appl. No. 15/718,521, filed Sep. 28, 2017, 39 pages.
Non-Final Office Action dated Jun. 30, 2017, issued in connection with U.S. Appl. No. 15/277,810, filed Sep. 27, 2016, 13 pages.
Non-Final Office Action dated Apr. 4, 2019, issued in connection with U.S. Appl. No. 15/718,911, filed Sep. 28, 2017, 21 pages.
Non-Final Office Action dated Jan. 4, 2019, issued in connection with U.S. Appl. No. 15/948,541, filed Apr. 9, 2018, 6 pages.
Non-Final Office Action dated Feb. 6, 2018, issued in connection with U.S. Appl. No. 15/211,689, filed Jul. 15, 2016, 32 pages.
Non-Final Office Action dated Feb. 6, 2018, issued in connection with U.S. Appl. No. 15/237,133, filed Aug. 15, 2016, 6 pages.
Non-Final Office Action dated Sep. 6, 2017, issued in connection with U.S. Appl. No. 15/131,254, filed Apr. 18, 2016, 13 pages.
Non-Final Office Action dated Sep. 6, 2018, issued in connection with U.S. Appl. No. 15/098,760, filed Apr. 14, 2016, 29 pages.
Non-Final Office Action dated Apr. 9, 2018, issued in connection with U.S. Appl. No. 15/804,776, filed Nov. 6, 2017, 18 pages.
Non-Final Office Action dated May 9, 2018, issued in connection with U.S. Appl. No. 15/818,051, filed Nov. 20, 2017, 22 pages.
Notice of Allowance dated Dec. 2, 2019, issued in connection with U.S. Appl. No. 15/718,521, filed Sep. 28, 2017, 15 pages.
Notice of Allowance dated Dec. 4, 2017, issued in connection with U.S. Appl. No. 15/277,810, filed Sep. 27, 2016, 5 pages.
Notice of Allowance dated Jul. 5, 2018, issued in connection with U.S. Appl. No. 15/237,133, filed Aug. 15, 2016, 5 pages.
Notice of Allowance dated Jul. 9, 2018, issued in connection with U.S. Appl. No. 15/438,741, filed Feb. 21, 2017, 5 pages.
Notice of Allowance dated Apr. 1, 2019, issued in connection with U.S. Appl. No. 15/935,966, filed Mar. 26, 2018, 5 pages.
Notice of Allowance dated Aug. 1, 2018, issued in connection with U.S. Appl. No. 15/297,627, filed Oct. 19, 2016, 9 pages.
Notice of Allowance dated Apr. 11, 2018, issued in connection with U.S. Appl. No. 15/719,454, filed Sep. 28, 2017, 15 pages.
Notice of Allowance dated Oct. 11, 2019, issued in connection with U.S. Appl. No. 16/437,476, filed Jun. 11, 2019, 9 pages.
Notice of Allowance dated Sep. 11, 2019, issued in connection with U.S. Appl. No. 16/154,071, filed Oct. 8, 2018, 5 pages.
Notice of Allowance dated Dec. 12, 2018, issued in connection with U.S. Appl. No. 15/811,468, filed Nov. 13, 2017, 9 pages.
Notice of Allowance dated Jul. 12, 2017, issued in connection with U.S. Appl. No. 15/098,805, filed Apr. 14, 2016, 8 pages.
Notice of Allowance dated Jun. 12, 2019, issued in connection with U.S. Appl. No. 15/670,361, filed Aug. 7, 2017, 7 pages.
Notice of Allowance dated Sep. 12, 2018, issued in connection with U.S. Appl. No. 15/438,744, filed Feb. 21, 2017, 15 pages.
Notice of Allowance dated Dec. 13, 2017, issued in connection with U.S. Appl. No. 15/784,952, filed Oct. 16, 2017, 9 pages.
Notice of Allowance dated Feb. 13, 2019, issued in connection with U.S. Appl. No. 15/959,907, filed Apr. 23, 2018, 10 pages.
Notice of Allowance dated Aug. 14, 2017, issued in connection with U.S. Appl. No. 15/098,867, filed Apr. 14, 2016, 10 pages.
Notice of Allowance dated Feb. 14, 2017, issued in connection with U.S. Appl. No. 15/229,855, filed Aug. 5, 2016, 11 pages.
Notice of Allowance dated Jun. 14, 2017, issued in connection with U.S. Appl. No. 15/282,554, filed Sep. 30, 2016, 11 pages.
Notice of Allowance dated Nov. 14, 2018, issued in connection with U.S. Appl. No. 15/297,627, filed Oct. 19, 2016, 5 pages.

(56) References Cited

OTHER PUBLICATIONS

Notice of Allowance dated Dec. 15, 2017, issued in connection with U.S. Appl. No. 15/223,218, filed Jul. 29, 2016, 7 pages.
Notice of Allowance dated Mar. 15, 2019, issued in connection with U.S. Appl. No. 15/804,776, filed Nov. 6, 2017, 9 pages.
Notice of Allowance dated Oct. 15, 2019, issued in connection with U.S. Appl. No. 16/437,437, filed Jun. 11, 2019, 9 pages.
Notice of Allowance dated Aug. 16, 2017, issued in connection with U.S. Appl. No. 15/098,892, filed Apr. 14, 2016, 9 pages.
Notice of Allowance dated Aug. 17, 2017, issued in connection with U.S. Appl. No. 15/131,244, filed Apr. 18, 2016, 9 pages.
Notice of Allowance dated Jul. 17, 2019, issued in connection with U.S. Appl. No. 15/718,911, filed Sep. 28, 2017, 5 pages.
Notice of Allowance dated Sep. 17, 2018, issued in connection with U.S. Appl. No. 15/211,689, filed Jul. 15, 2016, 6 pages.
Notice of Allowance dated Apr. 18, 2019, issued in connection with U.S. Appl. No. 16/173,797, filed Oct. 29, 2018, 9 pages.
Notice of Allowance dated Dec. 18, 2019, issued in connection with U.S. Appl. No. 16/434,426, filed Jun. 7, 2019, 13 pages.
Notice of Allowance dated Jul. 18, 2019, issued in connection with U.S. Appl. No. 15/438,749, filed Feb. 21, 2017, 9 pages.
Notice of Allowance dated Jul. 18, 2019, issued in connection with U.S. Appl. No. 15/721,141, filed Sep. 29, 2017, 8 pages.
Notice of Allowance dated Dec. 19, 2018, issued in connection with U.S. Appl. No. 15/818,051, filed Nov. 20, 2017, 9 pages.
Notice of Allowance dated Jul. 19, 2018, issued in connection with U.S. Appl. No. 15/681,937, filed Aug. 21, 2017, 7 pages.
Notice of Allowance dated Aug. 2, 2019, issued in connection with U.S. Appl. No. 16/102,650, filed Aug. 13, 2018, 5 pages.
Notice of Allowance dated Mar. 20, 2018, issued in connection with U.S. Appl. No. 15/784,952, filed Oct. 16, 2017, 7 pages.
Notice of Allowance dated Sep. 20, 2018, issued in connection with U.S. Appl. No. 15/946,599, filed Apr. 5, 2018, 7 pages.
Notice of Allowance dated Oct. 21, 2019, issued in connection with U.S. Appl. No. 15/946,585, filed Apr. 5, 2018, 5 pages.
Notice of Allowance dated Aug. 22, 2017, issued in connection with U.S. Appl. No. 15/273,679, filed Sep. 22, 2016, 5 pages.
Notice of Allowance dated Jan. 22, 2018, issued in connection with U.S. Appl. No. 15/178,180, filed Jun. 9, 2016, 9 pages.
Notice of Allowance dated Apr. 24, 2019, issued in connection with U.S. Appl. No. 16/154,469 filed Oct. 8, 2018, 5 pages.
Notice of Allowance dated Mar. 27, 2019, issued in connection with U.S. Appl. No. 16/214,666, filed Dec. 10, 2018, 6 pages.
Notice of Allowance dated Mar. 28, 2018, issued in connection with U.S. Appl. No. 15/699,982, filed Sep. 8, 2017, 17 pages.
Notice of Allowance dated Dec. 29, 2017, issued in connection with U.S. Appl. No. 15/131,776, filed Apr. 18, 2016, 13 pages.
Notice of Allowance dated Apr. 3, 2019, issued in connection with U.S. Appl. No. 16/160,107, filed Oct. 15, 2018, 7 pages.
Notice of Allowance dated Jul. 30, 2018, issued in connection with U.S. Appl. No. 15/098,718, filed Apr. 14, 2016, 5 pages.
Notice of Allowance dated Jul. 30, 2019, issued in connection with U.S. Appl. No. 15/131,254, filed Apr. 18, 2016, 9 pages.
Notice of Allowance dated Nov. 30, 2018, issued in connection with U.S. Appl. No. 15/438,725, filed Feb. 21, 2017, 5 pages.
Notice of Allowance dated Oct. 30, 2019, issued in connection with U.S. Appl. No. 16/131,392, filed Sep. 14, 2018, 9 pages.
Notice of Allowance dated May 31, 2019, issued in connection with U.S. Appl. No. 15/717,621, filed Sep. 27, 2017, 9 pages.
Notice of Allowance dated Oct. 5, 2018, issued in connection with U.S. Appl. No. 15/211,748, filed Jul. 15, 2018, 10 pages.
Notice of Allowance dated Feb. 6, 2019, issued in connection with U.S. Appl. No. 16/102,153, filed Aug. 13, 2018, 9 pages.
Notice of Allowance dated Jun. 7, 2019, issued in connection with U.S. Appl. No. 16/102,153, filed Aug. 13, 2018, 9 pages.
Notice of Allowance dated Aug. 9, 2018, issued in connection with U.S. Appl. No. 15/229,868, filed Aug. 5, 2016, 11 pages.
Notice of Allowance dated Mar. 9, 2018, issued in connection with U.S. Appl. No. 15/584,782, filed May 2, 2017, 8 pages.

Optimizing Siri on HomePod in Far-Field Settings. Audio Software Engineering and Siri Speech Team, Machine Learning Journal vol. 1, Issue 12. https://machinelearning.apple.com/2018/12/03/optimizing-siri-on-homepod-in-far-field-settings.html. Dec. 2018, 18 pages.
Palm, Inc., "Handbook for the Palm VII Handheld," May 2000, 311 pages.
Preinterview First Office Action dated Aug. 5, 2019, issued in connection with U.S. Appl. No. 16/434,426, filed Jun. 7, 2019, 4 pages.
Preinterview First Office Action dated Sep. 30, 2019, issued in connection with U.S. Appl. No. 15/989,715, filed May 25, 2018, 4 pages.
Presentations at WinHEC 2000, May 2000, 138 pages.
Restriction Requirement dated Aug. 14, 2019, issued in connection with U.S. Appl. No. 16/214,711, filed Dec. 10, 2018, 5 pages.
Restriction Requirement dated Aug. 9, 2018, issued in connection with U.S. Appl. No. 15/717,621, filed Sep. 27, 2017, 8 pages.
Souden et al. "An Integrated Solution for Online Multichannel Noise Tracking and Reduction." IEEE Transactions on Audio, Speech, and Language Processing, vol. 19. No. 7, Sep. 7, 2011, 11 pages.
Souden et al. "Gaussian Model-Based Multichannel Speech Presence Probability" IEEE Transactions on Audio, Speech, and Language Processing, vol. 18, No. 5, Jul. 5, 2010, 6pages.
Souden et al. "On Optimal Frequency-Domain Multichannel Linear Filtering for Noise Reduction." IEEE Transactions on Audio, Speech, and Language Processing, vol. 18, No. 2, Feb. 2010, 17pages.
Steven J. Nowlan and Geoffrey E. Hinton "Simplifying Neural Networks by Soft Weight-Sharing" Neural Computation 4, 1992, 21 pages.
Tsiami et al. "Experiments in acoustic source localization using sparse arrays in adverse indoors environments", 2014 22nd European Signal Processing Conference, Sep. 1, 2014, 5 pages.
Tweet: "How to start using Google app voice commands to make your life easier Share This Story shop @Bullet", Jan. 21, 2016, https://bgr.com/2016/01/21/best-ok-google-voice-commands/, 3 page.
Ullrich et al. "Soft Weight-Sharing for Neural Network Compression." ICLR 2017, 16 pages.
U.S. Appl. No. 60/490,768, filed Jul. 28, 2003, entitled "Method for synchronizing audio playback between multiple networked devices," 13 pages.
U.S. Appl. No. 60/825,407, filed Sep. 12, 2006, entitled "Controlling and manipulating groupings in a multi-zone music or media system," 82 pages.
UPnP; "Universal Plug and Play Device Architecture," Jun. 8, 2000; version 1.0; Microsoft Corporation; pp. 1-54.
Vacher at al. "Recognition of voice commands by multisource ASR and noise cancellation in a smart home environment" Signal Processing Conference 2012 Proceedings of the 20th European, IEEE, Aug. 27, 2012, 5 pages.
Vacher et al. "Speech Recognition in a Smart Home: Some Experiments for Telemonitoring," 2009 Proceedings of the 5th Conference on Speech Technology and Human-Computer Dialogoue, Constant, 2009, 10 pages.
"S Voice or Google Now?"; https://web.archive.org/web/20160807040123/lowdown.carphonewarehouse.com/news/s-voice-or-google-now/ . . . , Apr. 28, 2015; 4 pages.
Wung et al. "Robust Acoustic Echo Cancellation in the Short-Time Fourier Transform Domain Using Adaptive Crossband Filters" IEEE International Conference on Acoustic, Speech and Signal Processing ICASSP, 2014, p. 1300-1304.
Xiao et al. "A Learning-Based Approach to Direction of Arrival Estimation in Noisy and Reverberant Environments," 2015 IEEE International Conference on Acoustics, Speech and Signal Processing, Apr. 19, 2015, 5 pages.
Yamaha DME 64 Owner's Manual; copyright 2004, 80 pages.
Yamaha DME Designer 3.5 setup manual guide; copyright 2004, 16 pages.
Yamaha DME Designer 3.5 User Manual; Copyright 2004, 507 pages.

* cited by examiner

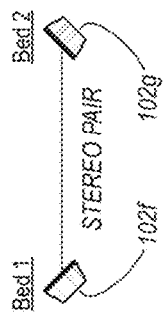
Fig. 3B
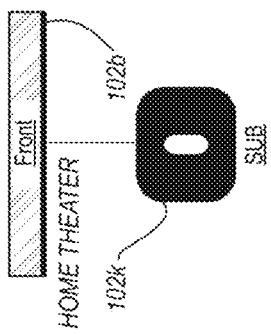
Fig. 3C
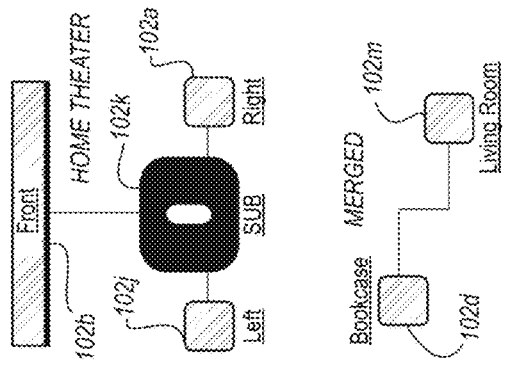
Fig. 3D
Fig. 3E
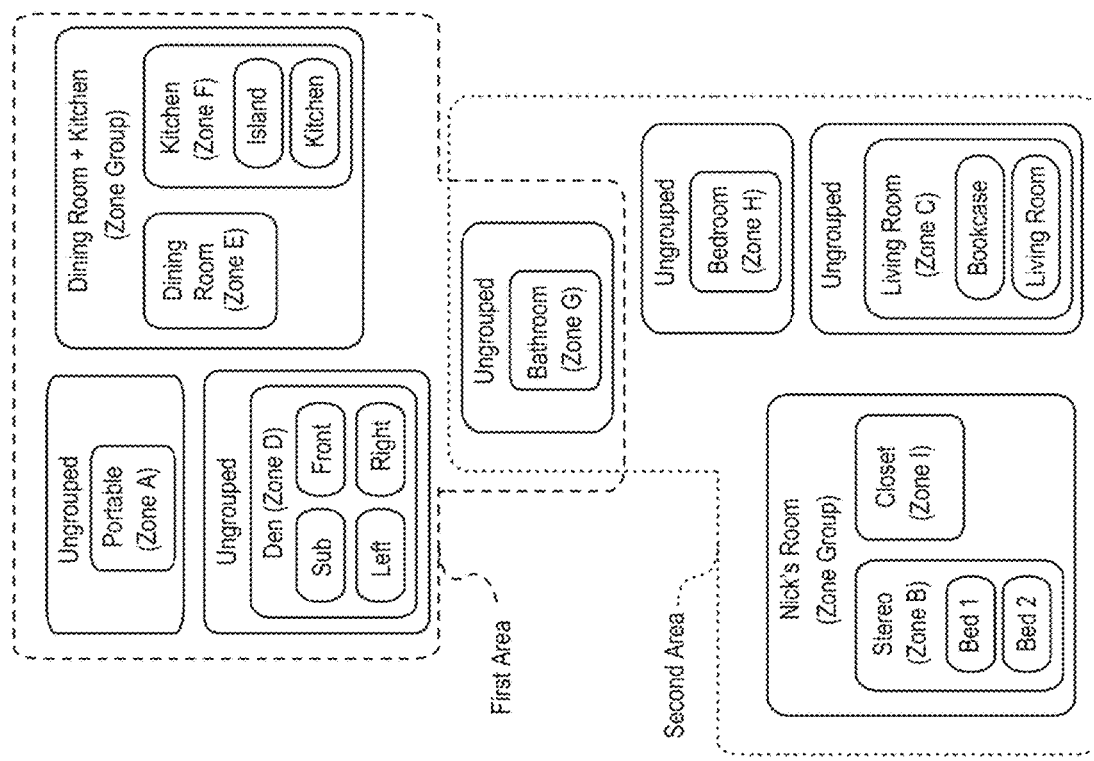
Fig. 3A

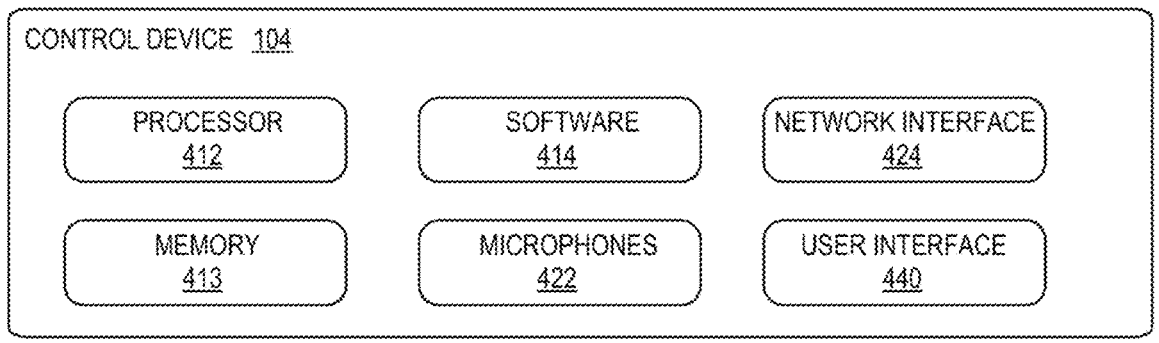
Fig. 4
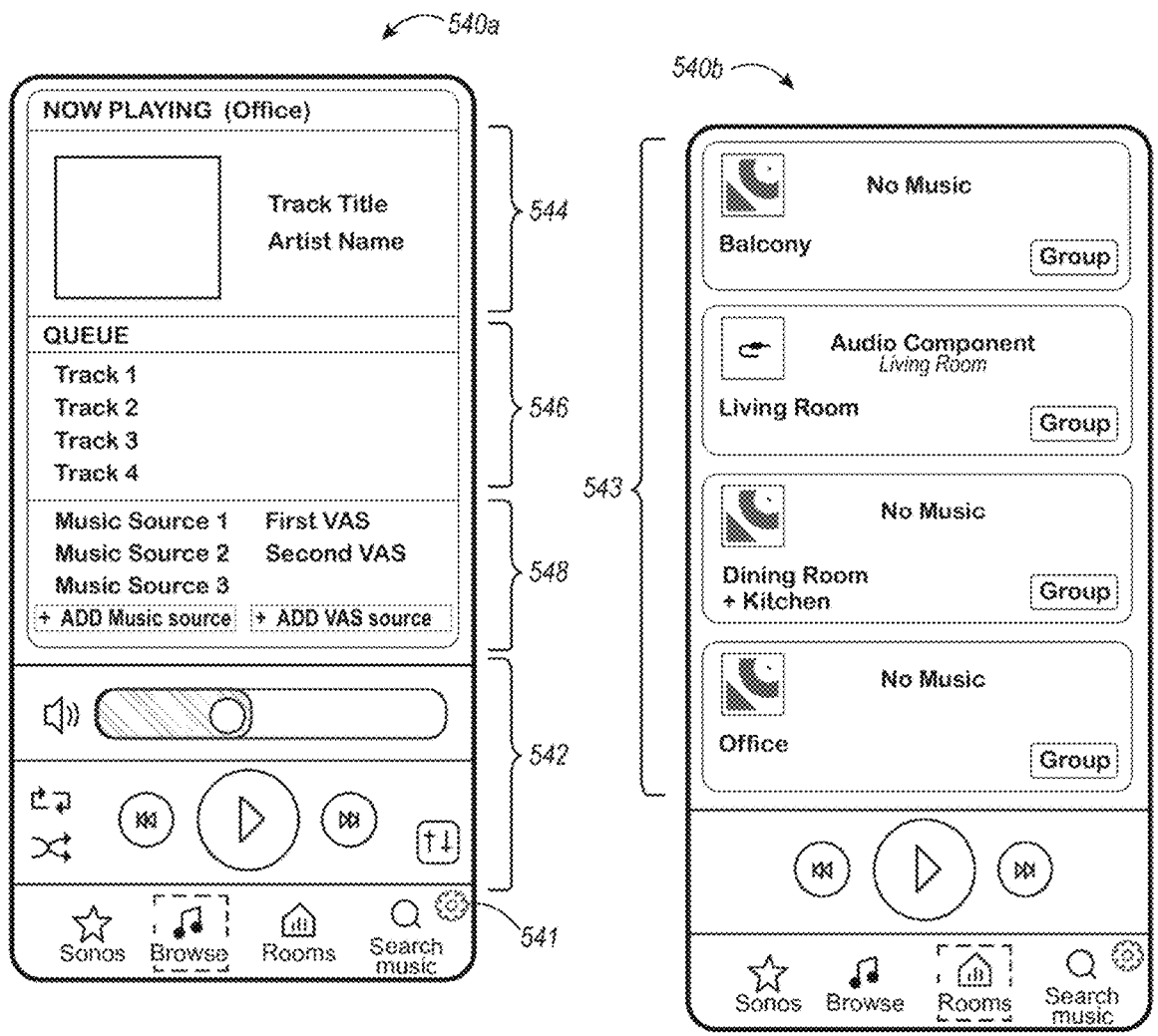
Fig. 5A
Fig. 5B

| Command Keyword | Cognates | First Condition | Second Condition | Third Condition |
|---|---|---|---|---|
| "play" | "turn on" "resume" | playback queue includes media items | | |
| "pause" | "stop" "quiet" "mute" "off" | audio content being played back | | |
| "next" | "skip" "forward" | audio content being played back | playback queue is active | playback queue includes media item subsequent to the media item being played back |
| "previous" | "back" "last" | audio content being played back | playback queue is active | playback queue includes media item prior to the media item being played back |
| "repeat" | "restart" | audio content being played back | | |
| "shuffle" | "randomize" | playback queue is active | playback queue includes multiple media items | |

Fig. 9A

| Command Keyword | Cognates | First Condition | Second Condition | Third Condition |
|---|---|---|---|---|
| "group" (device1) (device2) ... (deviceN) | "join" "combine" | devices are present in the media playback system | devices not grouped | |
| "pair" (device1) (device2) ... (deviceN) | "bond" | devices are present in the media playback system | devices not paired | |
| "calibrate" | "trueplay" "tune" | audio content is not being played back | | |
| "turn on" (device) | "activate" | device is turned off | | |
| "volume" | "louder" "quieter" "turn it up/down" | audio content being played back | volume not at minimum/maximum | |
| "mute" | "silence" "quiet" | audio content being played back | volume is not muted | |

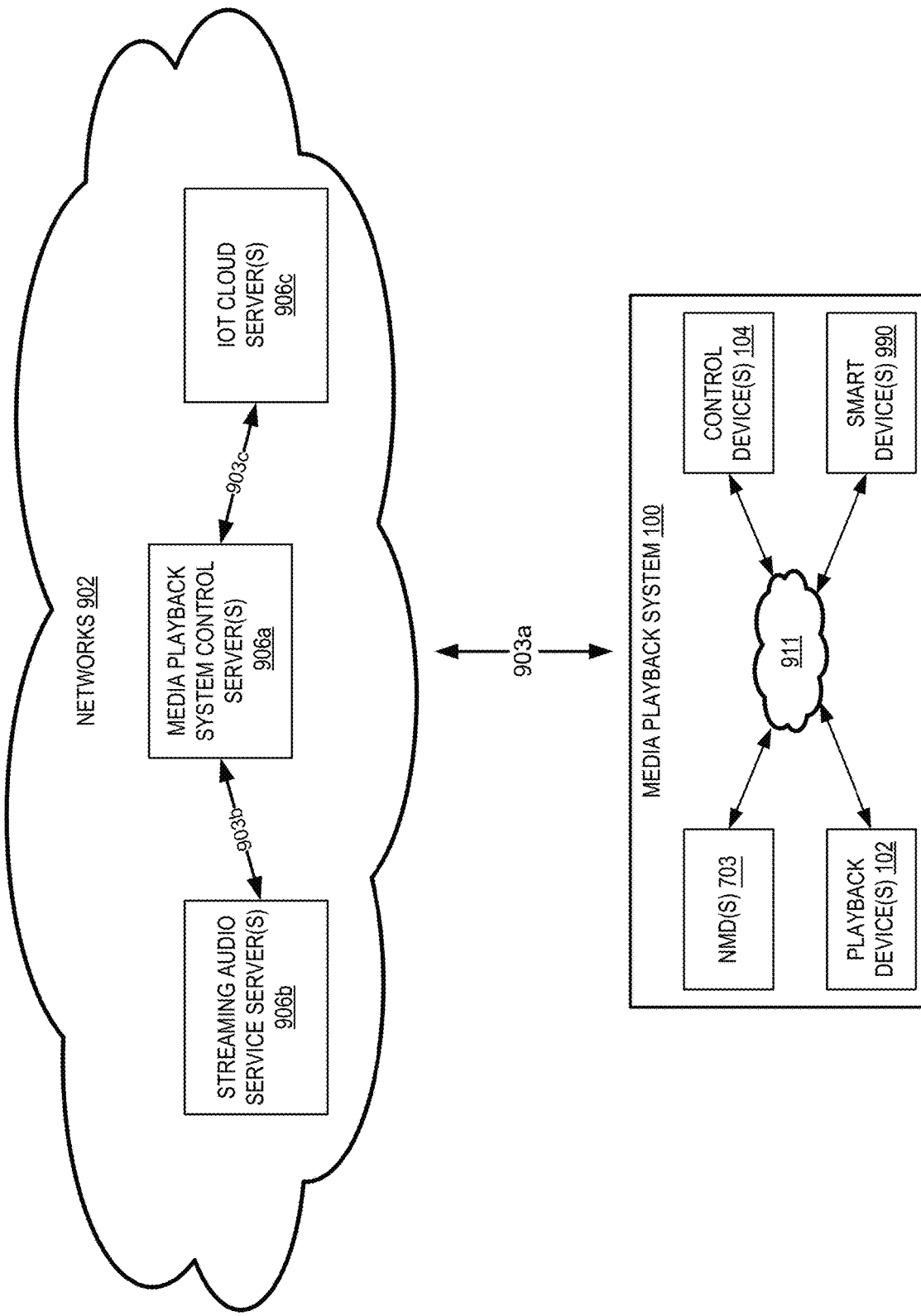

LOCALLY DISTRIBUTED KEYWORD DETECTION

FIELD OF THE DISCLOSURE

The present technology relates to consumer goods and, more particularly, to methods, systems, products, features, services, and other elements directed to voice-assisted control of media playback systems or some aspect thereof.

BACKGROUND

Options for accessing and listening to digital audio in an out-loud setting were limited until in 2002, when SONOS, Inc. began development of a new type of playback system. Sonos then filed one of its first patent applications in 2003, entitled "Method for Synchronizing Audio Playback between Multiple Networked Devices," and began offering its first media playback systems for sale in 2005. The Sonos Wireless Home Sound System enables people to experience music from many sources via one or more networked playback devices. Through a software control application installed on a controller (e.g., smartphone, tablet, computer, voice input device), one can play what she wants in any room having a networked playback device. Media content (e.g., songs, podcasts, video sound) can be streamed to playback devices such that each room with a playback device can play back corresponding different media content. In addition, rooms can be grouped together for synchronous playback of the same media content, and/or the same media content can be heard in all rooms synchronously.

BRIEF DESCRIPTION OF THE DRAWINGS

Features, aspects, and advantages of the presently disclosed technology may be better understood with regard to the following description, appended claims, and accompanying drawings, as listed below. A person skilled in the relevant art will understand that the features shown in the drawings are for purposes of illustrations, and variations, including different and/or additional features and arrangements thereof, are possible.

FIGS. 3A, 3B, 3C, 3D and 3E are diagrams showing example playback device configurations in accordance with aspects of the disclosure.

FIG. 4 is a functional block diagram of an example controller device in accordance with aspects of the disclosure.

FIGS. 5A and 5B are controller interfaces in accordance with aspects of the disclosure.

FIG. 9A shows a first portion of a table illustrating example command keywords and associated conditions in accordance with aspects of the disclosure.

FIG. 9B shows a second portion of a table illustrating example command keywords and associated conditions in accordance with aspects of the disclosure.

FIG. 10 is a schematic diagram illustrating an example media playback system and cloud network in accordance with aspects of the disclosure.

Figure 1A:
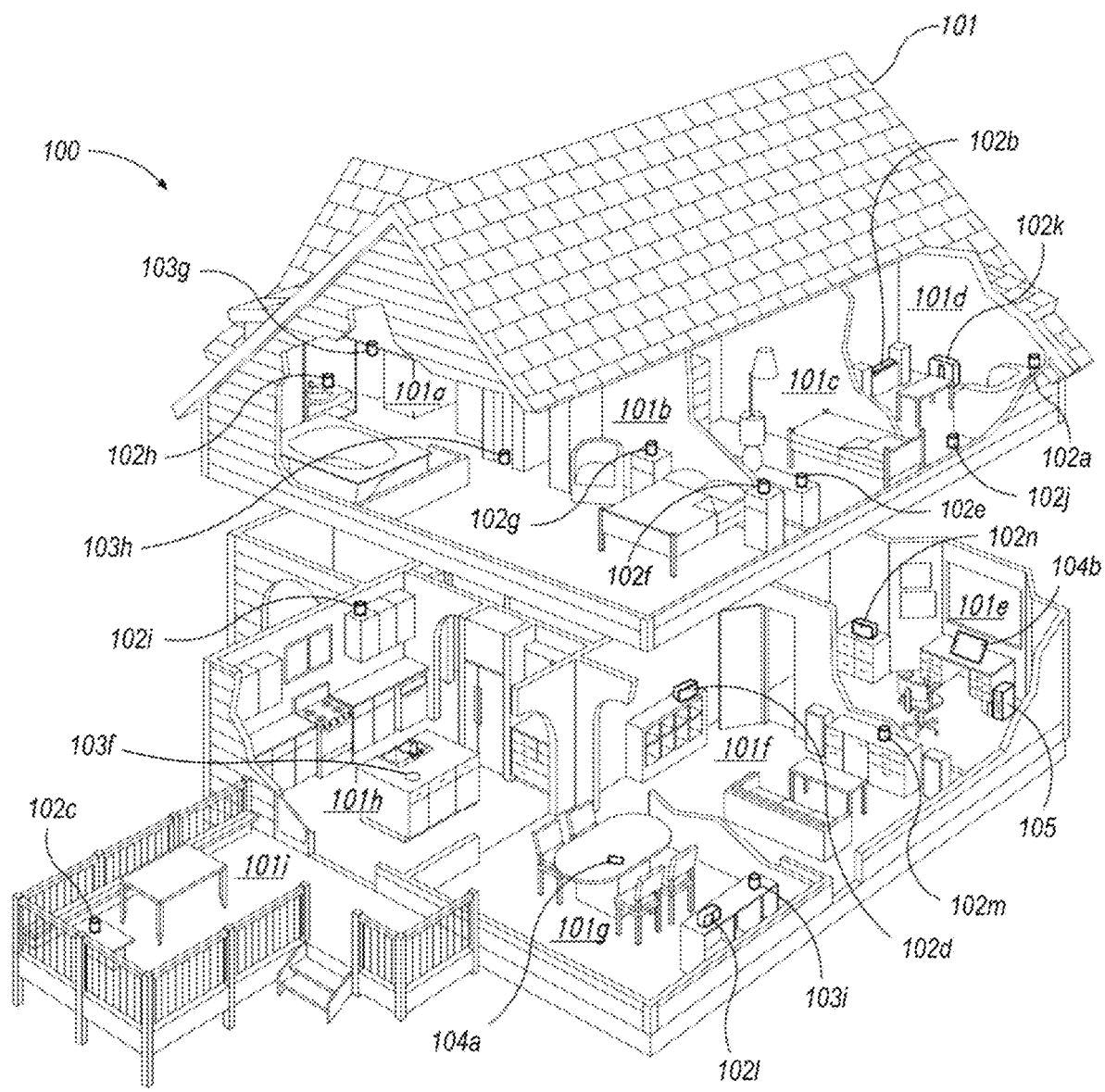
FIG. 1A is a partial cutaway view of an environment having a media playback system configured in accordance with aspects of the disclosed technology.

The drawings are for purposes of illustrating example embodiments, but it should be understood that the inventions are not limited to the arrangements and instrumentality shown in the drawings. In the drawings, identical reference numbers identify at least generally similar elements. To facilitate the discussion of any particular element, the most significant digit or digits of any reference number refers to the Figure in which that element is first introduced. For example, element 103a is first introduced and discussed with reference to FIG. 1A.

DETAILED DESCRIPTION

I. Overview

Example techniques described herein involve keyword engines configured to detect commands. An example network microphone device ("NMD") may implement such a keyword engine in parallel with a wake-word engine that invokes a voice assistant service ("VAS"). While a VAS wake-word engine may be involved with nonce wake-words, a command-keyword engine is invoked with commands, such as "play" or "skip."

Network microphone devices may be used facilitate voice control of smart home devices, such as wireless audio playback devices, illumination devices, appliances, and home-automation devices (e.g., thermostats, door locks, etc.). An NMD is a networked computing device that typically includes an arrangement of microphones, such as a microphone array, that is configured to detect sound present in the NMD's environment. In some examples, an NMD may be implemented within another device, such as an audio playback device.

A voice input to such an NMD will typically include a wake word followed by an utterance comprising a user request. In practice, a wake word is typically a predetermined nonce word or phrase used to "wake up" an NMD and cause it to invoke a particular voice assistant service ("VAS") to interpret the intent of voice input in detected sound. For example, a user might speak the wake word "Alexa" to invoke the AMAZON® VAS, "Ok, Google" to invoke the GOOGLE® VAS, "Hey, Siri" to invoke the APPLE® VAS, or "Hey, Sonos" to invoke a VAS offered by SONOS®, among other examples. In practice, a wake word may also be referred to as, for example, an activation-, trigger-, wakeup-word or -phrase, and may take the form of any suitable word, combination of words (e.g., a particular phrase), and/or some other audio cue.

To identify whether sound detected by the NMD contains a voice input that includes a particular wake word, NMDs often utilize a wake-word engine, which is typically onboard the NMD. The wake-word engine may be configured to identify (i.e., "spot" or "detect") a particular wake word in recorded audio using one or more identification algorithms. Such identification algorithms may include pattern recognition trained to detect the frequency and/or time domain patterns that speaking the wake word creates. This wake-word identification process is commonly referred to as "keyword spotting." In practice, to help facilitate keyword spotting, the NMD may buffer sound detected by a microphone of the NMD and then use the wake-word engine to process that buffered sound to determine whether a wake word is present in the recorded audio.

When a wake-word engine detects a wake word in recorded audio, the NMD may determine that a wake-word event (i.e., a "wake-word trigger") has occurred, which indicates that the NMD has detected sound that includes a potential voice input. The occurrence of the wake-word event typically causes the NMD to perform additional processes involving the detected sound. With a VAS wake-word engine, these additional processes may include extracting detected-sound data from a buffer, among other possible additional processes, such as outputting an alert (e.g., an audible chime and/or a light indicator) indicating that a wake word has been identified. Extracting the detected sound may include reading out and packaging a stream of the detected-sound according to a particular format and transmitting the packaged sound-data to an appropriate VAS for interpretation.

In turn, the VAS corresponding to the wake word that was identified by the wake-word engine receives the transmitted sound data from the NMD over a communication network. A VAS traditionally takes the form of a remote service implemented using one or more cloud servers configured to process voice inputs (e.g., AMAZON's ALEXA, APPLE's SIRI, MICROSOFT's CORTANA, GOOGLE'S ASSISTANT, etc.). In some instances, certain components and functionality of the VAS may be distributed across local and remote devices.

When a VAS receives detected-sound data, the VAS processes this data, which involves identifying the voice input and determining intent of words captured in the voice input. The VAS may then provide a response back to the NMD with some instruction according to the determined intent. Based on that instruction, the NMD may cause one or more smart devices to perform an action. For example, in accordance with an instruction from a VAS, an NMD may cause a playback device to play a particular song or an illumination device to turn on/off, among other examples. In some cases, an NMD, or a media system with NMDs (e.g., a media playback system with NMD-equipped playback devices) may be configured to interact with multiple VASes. In practice, the NMD may select one VAS over another based on the particular wake word identified in the sound detected by the NMD.

In contrast to a predetermined nonce wake word that invokes a VAS, a keyword that invokes a command (referred to herein as a "command keyword") may be a word or a combination of words (e.g., a phrase) that functions as a command itself, such as a playback command. In some implementations, a command keyword may function as both a wake word and the command itself. That is, when a command-keyword engine detects a command keyword in recorded audio, the NMD may determine that a command-keyword event has occurred and responsively performs a command corresponding to the detected keyword. For instance, based on detecting the command keyword "pause," the NMD causes playback to be paused. One advantage of a command-keyword engine is that the recorded audio does not necessarily need to be sent to a VAS for processing, which may result in a quicker response to the voice input as well as increased user privacy, among other possible benefits. In some implementations described below, a detected command-keyword event may cause one or more subsequent actions, such as local natural language processing of a voice input. In some implementations, a command-keyword event may be one condition among one or more other conditions that must be detected before causing such actions. Additional command keyword implementations can be found, for example, in U.S. patent application Ser. No. 16/439,009, filed Jun. 12, 2019, titled "Network Microphone Device with Command Keyword Conditioning"; U.S. patent application Ser. No. 16/439,032, filed Jun. 12, 2019, titled "Network Microphone Device with Command Word Eventing"; and U.S. patent application Ser. No. 16/439,046, filed Jun. 12, 2019, titled "Conditional Wake Word Eventing Based on Environment," which are incorporated herein by reference in their entireties.

According to example techniques described herein, after detecting a command keyword, example NMDs may generate a command-keyword event (and perform a command corresponding to the detected command keyword) only when certain conditions corresponding to the detected command keyword are met. For instance, after detecting the command keyword "skip," an example NMD generates a command-keyword event (and skips to the next track) only when certain playback conditions indicating that a skip should be performed are met. These playback conditions may include, for example, (i) a first condition that a media item is being played back, (ii) a second condition that a queue is active, and (iii) a third condition that the queue includes a media item subsequent to the media item being played back. If any of these conditions are not satisfied, the command-keyword event is not generated (and no skip is performed).

In some instances, detection of a command keyword can be limited by certain conditions. For example, if there is no content currently being played back, the available intents to be identified by the local NLU can be limited, for example by excluding keywords such as "pause," "skip," etc. Accordingly, while the media playback system is certain states, the range of potential keywords to be identified by the NLU can be limited to decrease the rate of false positives.

By requiring both (a) detection of a command keyword and (b) certain conditions corresponding to the detected command keyword before generating a command-keyword event, the prevalence of false positives may be reduced. For instance, when playing TV audio, dialogue or other TV audio would not have the potential to generate false positives for the "skip" command keyword since the TV audio input is active (and not a queue). Moreover, the NMD can continually listen for command keywords (rather than requiring a button press to put the NMD in condition to receive a voice input) as the conditions relating to the state of the controlled device gate command keyword event generation.

Aspects of conditioning keyword events may also be applicable to VAS wake-word engines and other traditional nonce wake-word engines. For example, such conditioning can possibly make practicable other wake word engines in addition to command-keyword engines that might otherwise be prone to false positives. For instance, an NMD may include a streaming audio service wake word engine that supports certain wake words unique to the streaming audio service. For instance, after detecting a streaming audio service wake word, an example NMD generates a streaming audio service wake word event only when certain streaming audio service playback conditions are met. These playback conditions may include, for example, (i) an active subscription to the streaming audio service and (ii) audio tracks from the streaming audio service in a queue, among other examples.

Further, a command keyword may be a single word or a phrase. Phrases generally include more syllables, which generally make the command keyword more unique and easier to identify by the command-keyword engine. Accordingly, in some cases, command keywords that are phrases may be less prone to false positive detections. Further, using a phrase may allow more intent to be incorporated into the command keyword. For instance, a command keyword of "skip forward" signals that a skip should be forward in a queue to a subsequent track, rather than backward to a previous track.

Yet further, an NMD may include a local natural language unit (NLU). As used herein, an NLU can be an onboard natural language understanding processor, or any other component or combination of components configured to recognize language in sound input data. In contrast to an NLU implemented in one or more cloud servers that is capable of recognizing a wide variety of voice inputs, example local NLUs are capable of recognizing a relatively small library of keywords (e.g., 10,000 intents, words and/or phrases), which facilitates practical implementation on the NMD. When the command-keyword engine generates a command-keyword event after detecting a command keyword in a voice input, the local NLU may process the voice input to look for keywords from the library and determine an intent from the found keywords.

If the voice utterance portion of the voice input includes at least one keyword from the library, the NMD may perform the command corresponding to the command keyword according to one or more parameters corresponding to the least one keyword. In other words, the keywords may alter or customize the command corresponding to the command keyword. For instance, the command-keyword engine may be configured to detect "play" as a command keyword and the local NLU library could include the phrase "low volume." Then, if the user speaks "Play music at low volume" as a voice input, the command-keyword engine generates a command-keyword event for "play" and uses the keyword "low volume" as a parameter for the "play" command. Accordingly, the NMD not only causes playback based on this voice input, but also lowers the volume. As another example, the command-keyword engine may be configured to detect "play" as a command keyword and the local NLU library could include the phrase "cancel." Then, if the user speaks "Play music . . . never mind, cancel that" as a voice input, the command-keyword engine may generate a command-keyword event for "play" but the keyword "cancel" is used as a parameter to modify or nullify the "play" command such that no action is taken by the NMD in response to the voice input.

Example techniques involve customizing the keywords in the library to users of the media playback system. For instance, the NMD may populate the library using names (e.g., zone names, smart device names, and user names) that have been configured in the media playback system. Yet further, the NMD may populate the local NLU library with names of favorite playlists, Internet radio stations, and the like. Such customization allows the local NLU to more efficiently assist the user with voice commands. Such customization may also be advantageous because the size of the local NLU library can be limited.

One possible advantage of a local NLU is increased privacy. By processing voice input locally, a user may avoid transmitting voice recordings to the cloud (e.g., to servers of a voice assistant service). Further, in some implementations, the NMD may use a local area network to discover playback devices and/or smart devices connected to the network, which may avoid providing this data to the cloud. Also, the user's preferences and customizations may remain local to the NMD(s) in the household, perhaps only using the cloud as an optional backup. Other advantages are possible as well.

Some environments (e.g., a user's household) can include multiple NMDs, each of which may include a command-keyword engine and/or a local NLU to facilitate local processing of voice input. In these environments, keyword detection can be improved by leveraging the presence multiple NMDs in a number of ways. In some embodiments, results from different NMDs can be compared to cross-check or confirm keyword detection. Additionally or alternatively, multiple NMDs can be used to expand the total library of supported keywords in the user's environment.

In some embodiments, different NMDs within a media playback system can support different libraries of keywords. As noted above, a local NLU associated with an NMD may support a relatively limited library of keywords (e.g., approximately 10,000 intents, words and/or phrases) as compared to its cloud-based counterparts. Accordingly, it can be useful to increase the total available keywords in a media playback system by assigning different libraries of keywords to different NMDs within the media playback system. For example, a first NMD might have a first NLU supporting a first library of keywords, and a second NMD might have a second NLU supporting a second, different library of keywords. As one example, if each NMD has a library with approximately 10,000 keywords, then two NMDs having completely non-overlapping libraries may provide a combined 20,000 keywords for the media playback system of which the two NMDs are a part. In operation, voice input received at any one of the NMDs within the system can be processed for keyword detection among multiple NMDs. As such, a single voice input can be evaluated for detection of keywords supported by two or more of the NMDs, thereby significantly increasing the total library of keywords supported by the system.

In some embodiments, the different libraries can include dedicated directories. For example, a first NLU of a first NMD may include a first library of keywords that are associated with a first intent category (e.g., transport commands), while a second NLU of a second NMD includes a second library of keywords associated with a second intent category (e.g., Internet-of-Things (TOT) commands or media service provider commands). By supporting different directories, a voice input received via a first NMD can be processed for detection of keywords associated with different intent categories, even if a single library on the first NMD would be unable to store or support the keywords associated with each of the different intent categories. In some embodiments, the dedicated directories can include sets of keywords used most often on those particular devices. For example, if, over time, a first NMD detects the command "turn on lights in the living room" repeatedly, keywords associated with this request (e.g., "turn on lights" and "living room") may be stored on the dedicated directory associated with the first NMD. In some cases, those keywords may not be stored in the libraries of other NMDs within the same media playback system.

In some embodiments, the different libraries supported by different NMDs can include partitions. For example, the library of a first NMD can include a first partition of shared keywords and a second partition of dedicated keywords. The shared keywords may be separately stored on the libraries of other NMDs within the same system, while the dedicated keywords may be stored only on that library, or in some instances only on a subset of all the libraries in the system. In some embodiments, the shared keywords can include keywords used most often (e.g., common transport commands such as "pause," "play," etc.). By storing the most commonly used commands in libraries of each NMD, the system may more consistently and responsively detect these keywords and perform associated operations. In some embodiments, there may be multiple partitions supported by each NMD, none of which is completely shared with other libraries. For example, the library of a first NMD might include a first partition storing IOT-command keywords, and a second partition storing transport-control keywords, while the library of a second NMD might include a first partition of user-associated keywords (e.g., the most command command-keywords associated with that user or environment) and a second partition storing keywords associated with media service providers.

Another way to improve local keyword detection via multiple NMDs is to cross-check keyword detection among two or more NMDs of the media playback system. In one example, a first NMD may receive and process voice input for keyword detection to obtain a result (e.g., a detection of the word "pause" in input sound data). In parallel, a second NMD may separately process the voice input for keyword detection and transmit the result back to the first NMD. The first NMD may then compare its own result with that obtained from the second NMD before determining whether to perform a certain action. If, for example, the results match (e.g., both NMDs identify the word "pause" in the voice input), the NMD may perform an action corresponding to the keywords. If, in contrast, the determinations do not match (e.g., the first NMD identified the word "pause," while the second NMD did not identify any keyword), then the first NMD may take no action, as this may indicate a lower confidence in either result. In this way, a second NMD is leveraged to cross-check the determination made by the first NMD.

In some embodiments, the cross-check or confirmation determination can be made not between two different NMDs, but between different subsets of input sound data from different microphones of a single NMD. For example, an NMD may have multiple microphones configured to generate sound data from a voice input. A first subset of the microphones may be used to generate first input sound data that can be evaluated to identify a keyword. A second subset of the microphones may be used to generate second input sound data from the same voice input that can be evaluated to identify a keyword. Comparing the results of these two processes can increase confidence and reduce false positives.

As noted above, example techniques relate to locally distributed keyword detection. A first example implementation involves a device including at least one speaker, one or more microphones configured to detect sound, a network interface, one or more processors, and data storage having instructions stored thereon. The device receives input sound data representing the sound detected by the one or more microphones and detects, via a command-keyword engine, a first command keyword in a first voice input represented in the input sound data. The command-keyword engine is configured to (a) process input sound data representing the sound detected by the at least one microphone and (b) generate a command-keyword event when the command-keyword engine detects, in the input sound data, at least one of a plurality of keywords supported by the command-keyword engine. In response to detecting the first command keyword, the device makes a first determination, via a first local natural language unit (NLU), whether the input sound data includes at least one keyword within a first a first predetermined library of keywords from which the first NLU is configured to determine an intent of a given voice input. The device receives an indication of a second determination made by a second NLU that the input sound data includes at least one keyword from the predetermined library of keywords. The device compares the results of the first determination with the results of the second determination and, based on the comparison, foregoes further processing of input sound data. For example, the comparison may indicate that the two determinations do not match (e.g., they did not identify the same keyword), and so no action is taken by the device.

A second example implementation involves a first device having at least one speaker, one or more microphones configured to detect sound, a network interface, one or more processors, and data storage having instructions stored thereon. The first device receives input sound data representing the sound detected by the one or more microphones and detects, via a command-keyword engine, a first command keyword in a first voice input represented in the input sound data. The command-keyword engine is configured to (a) process input sound data representing the sound detected by the at least one microphone and (b) generate a command-keyword event when the command-keyword engine detects, in the input sound data, one of a plurality of keywords supported by the command-keyword engine. In response to detecting the first command keyword, the first device determines, via a first local natural language unit (NLU), whether the input sound data includes at least one keyword within a first predetermined library of keywords from which the first NLU is configured to determine an intent of a given voice input. The first device transmits, via the network interface over a local area network, the input sound data to a second device, the second device employing a second local NLU with a second predetermined library of keywords from which the second NLU is configured to determine an intent of a given voice input. The first device receives, via the network interface, a response from the second device. After receiving the response from the second device, the first device performs an action based on an intent determined by at least one of the first NLU or the second NLU according to the one or more particular keywords in the voice input.

While some embodiments described herein may refer to functions performed by given actors, such as "users" and/or other entities, it should be understood that this description is for purposes of explanation only. The claims should not be interpreted to require action by any such example actor unless explicitly required by the language of the claims themselves.

Moreover, some functions are described herein as being performed "based on" or "in response to" another element or function. "Based on" should be understood that one element or function is related to another function or element. "In response to" should be understood that one element or function is a necessary result of another function or element. For the sake of brevity, functions are generally described as being based on another function when a functional link exists; however, such disclosure should be understood as disclosing either type of functional relationship.

II. Example Operation Environment

Figure 1B:
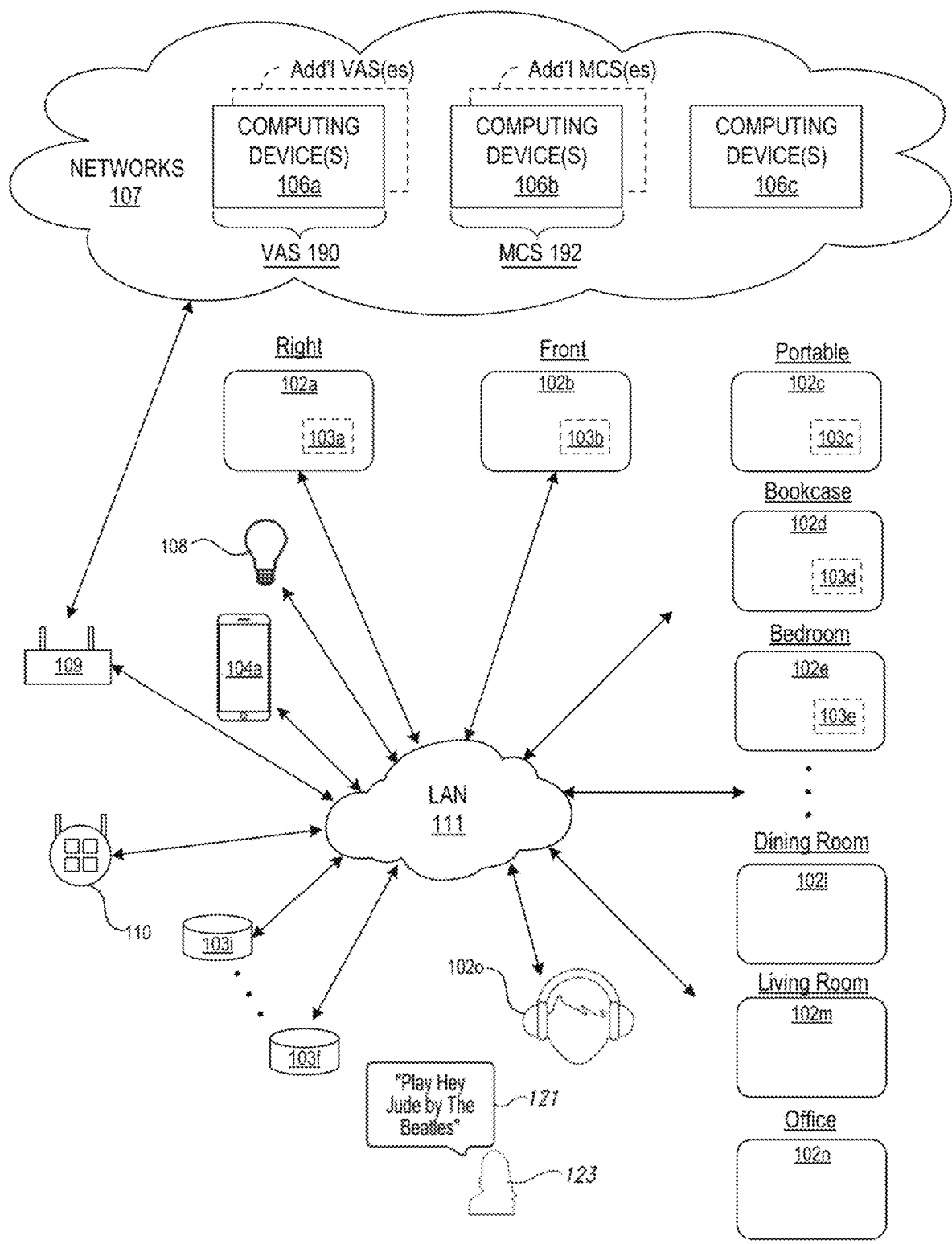
FIG. 1B is a schematic diagram of the media playback system of FIG. 1A and one or more networks.

FIGS. 1A and 1B illustrate an example configuration of a media playback system 100 (or "MPS 100") in which one or more embodiments disclosed herein may be implemented. Referring first to FIG. 1A, the MPS 100 as shown is associated with an example home environment having a plurality of rooms and spaces, which may be collectively referred to as a "home environment," "smart home," or "environment 101." The environment 101 comprises a household having several rooms, spaces, and/or playback zones, including a master bathroom 101a, a master bedroom 101b, (referred to herein as "Nick's Room"), a second bedroom 101c, a family room or den 101d, an office 101e, a living room 101f, a dining room 101g, a kitchen 101h, and an outdoor patio 101i. While certain embodiments and examples are described below in the context of a home environment, the technologies described herein may be implemented in other types of environments. In some embodiments, for example, the MPS 100 can be implemented in one or more commercial settings (e.g., a restaurant, mall, airport, hotel, a retail or other store), one or more vehicles (e.g., a sports utility vehicle, bus, car, a ship, a boat, an airplane), multiple environments (e.g., a combination of home and vehicle environments), and/or another suitable environment where multi-zone audio may be desirable.

Within these rooms and spaces, the MPS 100 includes one or more computing devices. Referring to FIGS. 1A and 1B together, such computing devices can include playback devices 102 (identified individually as playback devices 102a-102o), network microphone devices 103 (identified individually as "NMDs" 103a-102i), and controller devices 104a and 104b (collectively "controller devices 104"). Referring to FIG. 1B, the home environment may include additional and/or other computing devices, including local network devices, such as one or more smart illumination devices 108 (FIG. 1B), a smart thermostat 110, and a local computing device 105 (FIG. 1A). In embodiments described below, one or more of the various playback devices 102 may be configured as portable playback devices, while others may be configured as stationary playback devices. For example, the headphones 102o (FIG. 1B) are a portable playback device, while the playback device 102d on the bookcase may be a stationary device. As another example, the playback device 102c on the Patio may be a battery-powered device, which may allow it to be transported to various areas within the environment 101, and outside of the environment 101, when it is not plugged in to a wall outlet or the like.

With reference still to FIG. 1B, the various playback, network microphone, and controller devices 102, 103, and 104 and/or other network devices of the MPS 100 may be coupled to one another via point-to-point connections and/or over other connections, which may be wired and/or wireless, via a network 111, such as a local area network (LAN) which may include a network router 109. As used herein, a local area network can include any communications technology that is not configured for wide area communications, for example, WiFi, Bluetooth, Digital Enhanced Cordless Telecommunications (DECT), Ultra-WideBand, etc. For example, the playback device 102j in the Den 101d (FIG. 1A), which may be designated as the "Left" device, may have a point-to-point connection with the playback device 102a, which is also in the Den 101d and may be designated as the "Right" device. In a related embodiment, the Left playback device 102j may communicate with other network devices, such as the playback device 102b, which may be designated as the "Front" device, via a point-to-point connection and/or other connections via the NETWORK 111.

As further shown in FIG. 1B, the MPS 100 may be coupled to one or more remote computing devices 106 via a wide area network ("WAN") 107. In some embodiments, each remote computing device 106 may take the form of one or more cloud servers. The remote computing devices 106 may be configured to interact with computing devices in the environment 101 in various ways. For example, the remote computing devices 106 may be configured to facilitate streaming and/or controlling playback of media content, such as audio, in the home environment 101.

In some implementations, the various playback devices, NMDs, and/or controller devices 102-104 may be communicatively coupled to at least one remote computing device associated with a VAS and at least one remote computing device associated with a media content service ("MCS"). For instance, in the illustrated example of FIG. 1B, remote computing devices 106 are associated with a VAS 190 and remote computing devices 106b are associated with an MCS 192. Although only a single VAS 190 and a single MCS 192 are shown in the example of FIG. 1B for purposes of clarity, the MPS 100 may be coupled to multiple, different VASes and/or MCSes. In some implementations, VASes may be operated by one or more of AMAZON, GOOGLE, APPLE, MICROSOFT, SONOS or other voice assistant providers. In some implementations, MCSes may be operated by one or more of SPOTIFY, PANDORA, AMAZON MUSIC, or other media content services.

As further shown in FIG. 1B, the remote computing devices 106 further include remote computing device 106c configured to perform certain operations, such as remotely facilitating media playback functions, managing device and system status information, directing communications between the devices of the MPS 100 and one or multiple VASes and/or MCSes, among other operations. In one example, the remote computing devices 106c provide cloud servers for one or more SONOS Wireless HiFi Systems.

In various implementations, one or more of the playback devices 102 may take the form of or include an on-board (e.g., integrated) network microphone device. For example, the playback devices 102a-e include or are otherwise equipped with corresponding NMDs 103a-e, respectively. A playback device that includes or is equipped with an NMD may be referred to herein interchangeably as a playback device or an NMD unless indicated otherwise in the description. In some cases, one or more of the NMDs 103 may be a stand-alone device. For example, the NMDs 103f and 103g may be stand-alone devices. A stand-alone NMD may omit components and/or functionality that is typically included in a playback device, such as a speaker or related electronics. For instance, in such cases, a stand-alone NMD may not produce audio output or may produce limited audio output (e.g., relatively low-quality audio output).

The various playback and network microphone devices 102 and 103 of the MPS 100 may each be associated with a unique name, which may be assigned to the respective devices by a user, such as during setup of one or more of these devices. For instance, as shown in the illustrated example of FIG. 1B, a user may assign the name "Bookcase" to playback device 102d because it is physically situated on a bookcase. Similarly, the NMD 103f may be assigned the named "Island" because it is physically situated on an island countertop in the Kitchen 101h (FIG. 1A). Some playback devices may be assigned names according to a zone or room, such as the playback devices 102e, 102l, 102m, and 102n, which are named "Bedroom," "Dining Room," "Living Room," and "Office," respectively. Further, certain playback devices may have functionally descriptive names. For example, the playback devices 102a and 102b are assigned the names "Right" and "Front," respectively, because these two devices are configured to provide specific audio channels during media playback in the zone of the Den 101d (FIG. 1A). The playback device 102c in the Patio may be named portable because it is battery-powered and/or readily transportable to different areas of the environment 101. Other naming conventions are possible.

As discussed above, an NMD may detect and process sound from its environment, such as sound that includes background noise mixed with speech spoken by a person in the NMD's vicinity. For example, as sounds are detected by the NMD in the environment, the NMD may process the detected sound to determine if the sound includes speech that contains voice input intended for the NMD and ultimately a particular VAS. For example, the NMD may identify whether speech includes a wake word associated with a particular VAS.

In the illustrated example of FIG. 1B, the NMDs 103 are configured to interact with the VAS 190 over a network via the network 111 and the router 109. Interactions with the VAS 190 may be initiated, for example, when an NMD identifies in the detected sound a potential wake word. The identification causes a wake-word event, which in turn causes the NMD to begin transmitting detected-sound data to the VAS 190. In some implementations, the various local network devices 102-105 (FIG. 1A) and/or remote computing devices 106c of the MPS 100 may exchange various feedback, information, instructions, and/or related data with the remote computing devices associated with the selected VAS. Such exchanges may be related to or independent of transmitted messages containing voice inputs. In some embodiments, the remote computing device(s) and the MPS 100 may exchange data via communication paths as described herein and/or using a metadata exchange channel as described in U.S. application Ser. No. 15/438,749 filed Feb. 21, 2017, and titled "Voice Control of a Media Playback System," which is herein incorporated by reference in its entirety.

Upon receiving the stream of sound data, the VAS 190 determines if there is voice input in the streamed data from the NMD, and if so the VAS 190 will also determine an underlying intent in the voice input. The VAS 190 may next transmit a response back to the MPS 100, which can include transmitting the response directly to the NMD that caused the wake-word event. The response is typically based on the intent that the VAS 190 determined was present in the voice input. As an example, in response to the VAS 190 receiving a voice input with an utterance to "Play Hey Jude by The Beatles," the VAS 190 may determine that the underlying intent of the voice input is to initiate playback and further determine that intent of the voice input is to play the particular song "Hey Jude." After these determinations, the VAS 190 may transmit a command to a particular MCS 192 to retrieve content (i.e., the song "Hey Jude"), and that MCS 192, in turn, provides (e.g., streams) this content directly to the MPS 100 or indirectly via the VAS 190. In some implementations, the VAS 190 may transmit to the MPS 100 a command that causes the MPS 100 itself to retrieve the content from the MCS 192.

In certain implementations, NMDs may facilitate arbitration amongst one another when voice input is identified in speech detected by two or more NMDs located within proximity of one another. For example, the NMD-equipped playback device 102d in the environment 101 (FIG. 1A) is in relatively close proximity to the NMD-equipped Living Room playback device 102m, and both devices 102d and 102m may at least sometimes detect the same sound. In such cases, this may require arbitration as to which device is ultimately responsible for providing detected-sound data to the remote VAS. Examples of arbitrating between NMDs may be found, for example, in previously referenced U.S. application Ser. No. 15/438,749. When performing local command-keyword detection, as described in more detail below, it may be useful to forego or delay any such arbitration, such that two or more NMDs may process the same voice input for command-keyword detection. This can allow results of voice processing of two or more different NMDS to be compared to one another as a way to cross-check keyword detection results. In some embodiments, results of NLU determinations associated with different NMDs can be used to arbitrate between them. For example, if a first NLU associated with a first NMD identifies a keyword with a higher confidence level than that of a second NLU associated with the second NMD, then the first NMD may be selected over the second NMD.

In certain implementations, an NMD may be assigned to, or otherwise associated with, a designated or default playback device that may not include an NMD. For example, the Island NMD 103f in the Kitchen 101h (FIG. 1A) may be assigned to the Dining Room playback device 102l, which is in relatively close proximity to the Island NMD 103f. In practice, an NMD may direct an assigned playback device to play audio in response to a remote VAS receiving a voice input from the NMD to play the audio, which the NMD might have sent to the VAS in response to a user speaking a command to play a certain song, album, playlist, etc. Additional details regarding assigning NMDs and playback devices as designated or default devices may be found, for example, in previously referenced U.S. patent application No.

Further aspects relating to the different components of the example MPS 100 and how the different components may interact to provide a user with a media experience may be found in the following sections. While discussions herein may generally refer to the example MPS 100, technologies described herein are not limited to applications within, among other things, the home environment described above. For instance, the technologies described herein may be useful in other home environment configurations comprising more or fewer of any of the playback, network microphone, and/or controller devices 102-104. For example, the technologies herein may be utilized within an environment having a single playback device 102 and/or a single NMD 103. In some examples of such cases, the NETWORK 111 (FIG. 1B) may be eliminated and the single playback device 102 and/or the single NMD 103 may communicate directly with the remote computing devices 106-d. In some embodiments, a telecommunication network (e.g., an LTE network, a 5G network, etc.) may communicate with the various playback, network microphone, and/or controller devices 102-104 independent of a LAN.

a. Example Playback & Network Microphone Devices

Figure 2A:
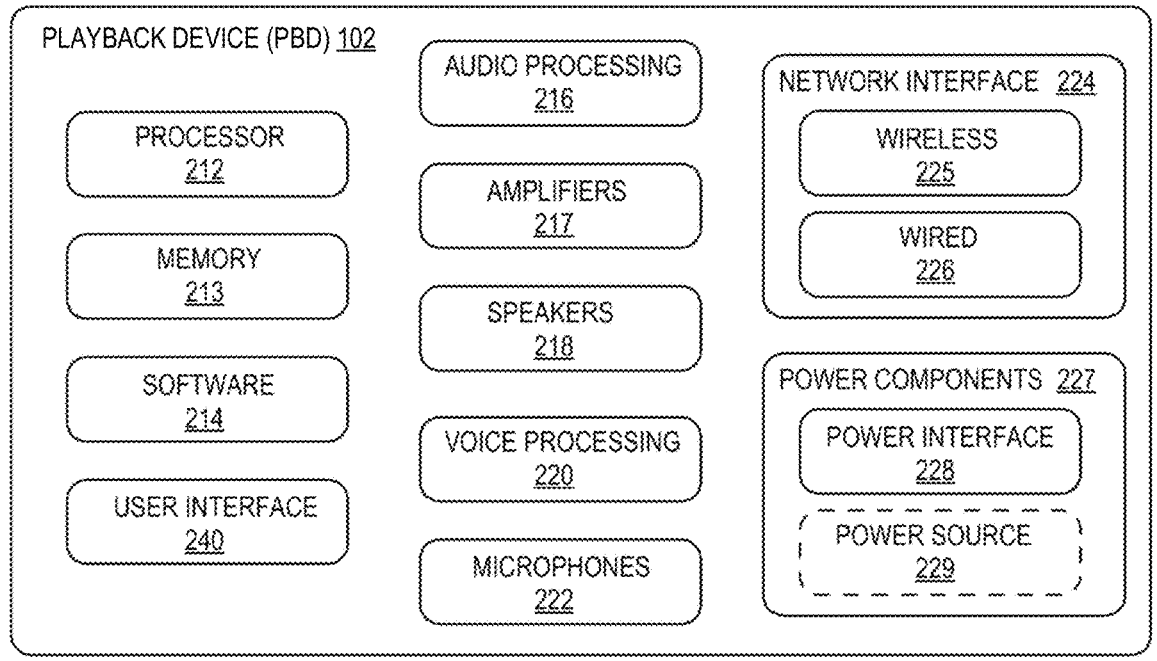
FIG. 2A is a functional block diagram of an example playback device.

FIG. 2A is a functional block diagram illustrating certain aspects of one of the playback devices 102 of the MPS 100 of FIGS. 1A and 1B. As shown, the playback device 102 includes various components, each of which is discussed in further detail below, and the various components of the playback device 102 may be operably coupled to one another via a system bus, communication network, or some other connection mechanism. In the illustrated example of FIG. 2A, the playback device 102 may be referred to as an "NMD-equipped" playback device because it includes components that support the functionality of an NMD, such as one of the NMDs 103 shown in FIG. 1A.

As shown, the playback device 102 includes at least one processor 212, which may be a clock-driven computing component configured to process input data according to instructions stored in memory 213. The memory 213 may be a tangible, non-transitory, computer-readable medium configured to store instructions that are executable by the processor 212. For example, the memory 213 may be data storage that can be loaded with software code 214 that is executable by the processor 212 to achieve certain functions.

In one example, these functions may involve the playback device 102 retrieving audio data from an audio source, which may be another playback device. In another example, the functions may involve the playback device 102 sending audio data, detected-sound data (e.g., corresponding to a voice input), and/or other information to another device on a network via at least one network interface 224. In yet another example, the functions may involve the playback device 102 causing one or more other playback devices to synchronously playback audio with the playback device 102. In yet a further example, the functions may involve the playback device 102 facilitating being paired or otherwise bonded with one or more other playback devices to create a multi-channel audio environment. Numerous other example functions are possible, some of which are discussed below.

As just mentioned, certain functions may involve the playback device 102 synchronizing playback of audio content with one or more other playback devices. During synchronous playback, a listener may not perceive time-delay differences between playback of the audio content by the synchronized playback devices. U.S. Pat. No. 8,234,395 filed on Apr. 4, 2004, and titled "System and method for synchronizing operations among a plurality of independently clocked digital data processing devices," which is hereby incorporated by reference in its entirety, provides in more detail some examples for audio playback synchronization among playback devices.

To facilitate audio playback, the playback device 102 includes audio processing components 216 that are generally configured to process audio prior to the playback device 102 rendering the audio. In this respect, the audio processing components 216 may include one or more digital-to-analog converters ("DAC"), one or more audio preprocessing components, one or more audio enhancement components, one or more digital signal processors ("DSPs"), and so on. In some implementations, one or more of the audio processing components 216 may be a subcomponent of the processor 212. In operation, the audio processing components 216 receive analog and/or digital audio and process and/or otherwise intentionally alter the audio to produce audio signals for playback.

The produced audio signals may then be provided to one or more audio amplifiers 217 for amplification and playback through one or more speakers 218 operably coupled to the amplifiers 217. The audio amplifiers 217 may include components configured to amplify audio signals to a level for driving one or more of the speakers 218.

Each of the speakers 218 may include an individual transducer (e.g., a "driver") or the speakers 218 may include a complete speaker system involving an enclosure with one or more drivers. A particular driver of a speaker 218 may include, for example, a subwoofer (e.g., for low frequencies), a mid-range driver (e.g., for middle frequencies), and/or a tweeter (e.g., for high frequencies). In some cases, a transducer may be driven by an individual corresponding audio amplifier of the audio amplifiers 217. In some implementations, a playback device may not include the speakers 218, but instead may include a speaker interface for connecting the playback device to external speakers. In certain embodiments, a playback device may include neither the speakers 218 nor the audio amplifiers 217, but instead may include an audio interface (not shown) for connecting the playback device to an external audio amplifier or audio-visual receiver.

In addition to producing audio signals for playback by the playback device 102, the audio processing components 216 may be configured to process audio to be sent to one or more other playback devices, via the network interface 224, for playback. In example scenarios, audio content to be processed and/or played back by the playback device 102 may be received from an external source, such as via an audio line-in interface (e.g., an auto-detecting 3.5 mm audio line-in connection) of the playback device 102 (not shown) or via the network interface 224, as described below.

As shown, the at least one network interface 224, may take the form of one or more wireless interfaces 225 and/or one or more wired interfaces 226. A wireless interface may provide network interface functions for the playback device 102 to wirelessly communicate with other devices (e.g., other playback device(s), NMD(s), and/or controller device(s)) in accordance with a communication protocol (e.g., any wireless standard including IEEE 802.11a, 802.11b, 802.11g, 802.11n, 802.11ac, 802.15, 4G mobile communication standard, and so on). A wired interface may provide network interface functions for the playback device 102 to communicate over a wired connection with other devices in accordance with a communication protocol (e.g., IEEE 802.3). While the network interface 224 shown in FIG. 2A include both wired and wireless interfaces, the playback device 102 may in some implementations include only wireless interface(s) or only wired interface(s).

In general, the network interface 224 facilitates data flow between the playback device 102 and one or more other devices on a data network. For instance, the playback device 102 may be configured to receive audio content over the data network from one or more other playback devices, network devices within a LAN, and/or audio content sources over a WAN, such as the Internet. In one example, the audio content and other signals transmitted and received by the playback device 102 may be transmitted in the form of digital packet data comprising an Internet Protocol (IP)-based source address and IP-based destination addresses. In such a case, the network interface 224 may be configured to parse the digital packet data such that the data destined for the playback device 102 is properly received and processed by the playback device 102.

As shown in FIG. 2A, the playback device 102 also includes voice processing components 220 that are operably coupled to one or more microphones 222. The microphones 222 are configured to detect sound (i.e., acoustic waves) in the environment of the playback device 102, which is then provided to the voice processing components 220. More specifically, each microphone 222 is configured to detect sound and convert the sound into a digital or analog signal representative of the detected sound, which can then cause the voice processing component 220 to perform various functions based on the detected sound, as described in greater detail below. In one implementation, the microphones 222 are arranged as an array of microphones (e.g., an array of six microphones). In some implementations, the playback device 102 includes more than six microphones (e.g., eight microphones or twelve microphones) or fewer than six microphones (e.g., four microphones, two microphones, or a single microphones).

In operation, the voice-processing components 220 are generally configured to detect and process sound received via the microphones 222, identify potential voice input in the detected sound, and extract detected-sound data to enable a VAS, such as the VAS 190 (FIG. 1B), to process voice input identified in the detected-sound data. The voice processing components 220 may include one or more analog-to-digital converters, an acoustic echo canceller ("AEC"), a spatial processor (e.g., one or more multi-channel Wiener filters, one or more other filters, and/or one or more beam former components), one or more buffers (e.g., one or more circular buffers), one or more wake-word engines, one or more voice extractors, and/or one or more speech processing components (e.g., components configured to recognize a voice of a particular user or a particular set of users associated with a household), among other example voice processing components. In example implementations, the voice processing components 220 may include or otherwise take the form of one or more DSPs or one or more modules of a DSP. In this respect, certain voice processing components 220 may be configured with particular parameters (e.g., gain and/or spectral parameters) that may be modified or otherwise tuned to achieve particular functions. In some implementations, one or more of the voice processing components 220 may be a subcomponent of the processor 212.

As further shown in FIG. 2A, the playback device 102 also includes power components 227. The power components 227 include at least an external power source interface 228, which may be coupled to a power source (not shown) via a power cable or the like that physically connects the playback device 102 to an electrical outlet or some other external power source. Other power components may include, for example, transformers, converters, and like components configured to format electrical power.

In some implementations, the power components 227 of the playback device 102 may additionally include an internal power source 229 (e.g., one or more batteries) configured to power the playback device 102 without a physical connection to an external power source. When equipped with the internal power source 229, the playback device 102 may operate independent of an external power source. In some such implementations, the external power source interface 228 may be configured to facilitate charging the internal power source 229. As discussed before, a playback device comprising an internal power source may be referred to herein as a "portable playback device." On the other hand, a playback device that operates using an external power source may be referred to herein as a "stationary playback device," although such a device may in fact be moved around a home or other environment.

The playback device 102 further includes a user interface 240 that may facilitate user interactions independent of or in conjunction with user interactions facilitated by one or more of the controller devices 104. In various embodiments, the user interface 240 includes one or more physical buttons and/or supports graphical interfaces provided on touch sensitive screen(s) and/or surface(s), among other possibilities, for a user to directly provide input. The user interface 240 may further include one or more of lights (e.g., LEDs) and the speakers to provide visual and/or audio feedback to a user.

Figure 2B:
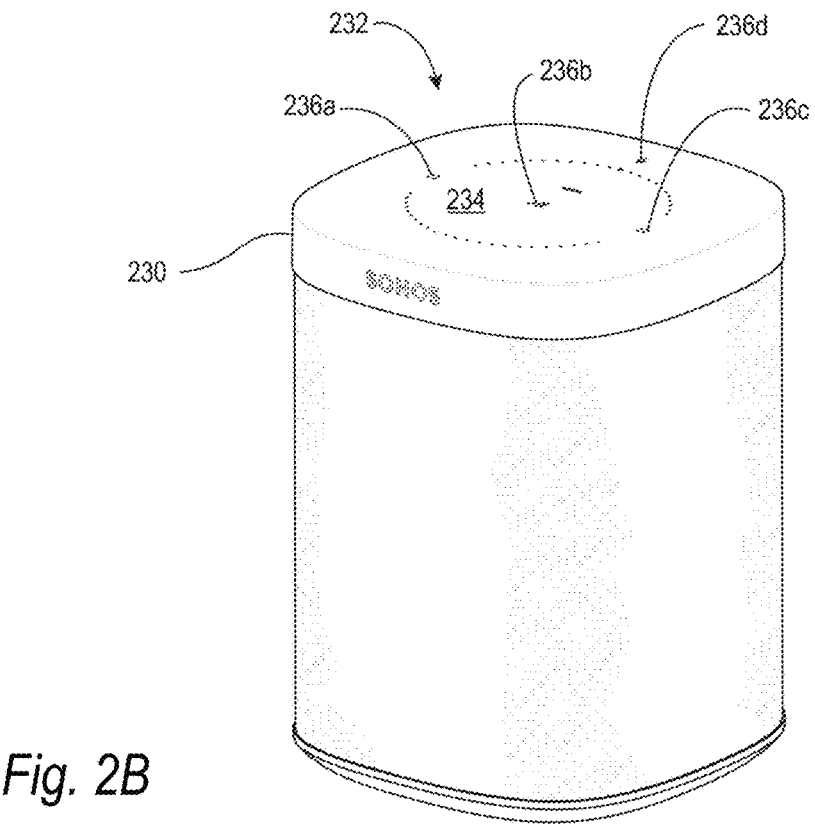
FIG. 2B is an isometric diagram of an example housing of the playback device of FIG. 2A.

As an illustrative example, FIG. 2B shows an example housing 230 of the playback device 102 that includes a user interface in the form of a control area 232 at a top portion 234 of the housing 230. The control area 232 includes buttons 236a-c for controlling audio playback, volume level, and other functions. The control area 232 also includes a button 236d for toggling the microphones 222 to either an on state or an off state.

As further shown in FIG. 2B, the control area 232 is at least partially surrounded by apertures formed in the top portion 234 of the housing 230 through which the microphones 222 (not visible in FIG. 2B) receive the sound in the environment of the playback device 102. The microphones 222 may be arranged in various positions along and/or within the top portion 234 or other areas of the housing 230 so as to detect sound from one or more directions relative to the playback device 102.

By way of illustration, SONOS, Inc. presently offers (or has offered) for sale certain playback devices that may implement certain of the embodiments disclosed herein, including a "PLAY: 1," "PLAY: 3," "PLAY: 5," "PLAYBAR," "CONNECT:AMP," "PLAYBASE," "BEAM," "CONNECT," and "SUB." Any other past, present, and/or future playback devices may additionally or alternatively be used to implement the playback devices of example embodiments disclosed herein. Additionally, it should be understood that a playback device is not limited to the examples illustrated in FIG. 2A or 2B or to the SONOS product offerings. For example, a playback device may include, or otherwise take the form of, a wired or wireless headphone set, which may operate as a part of the MPS 100 via a network interface or the like. In another example, a playback device may include or interact with a docking station for personal mobile media playback devices. In yet another example, a playback device may be integral to another device or component such as a television, a lighting fixture, or some other device for indoor or outdoor use.

Figure 2C:
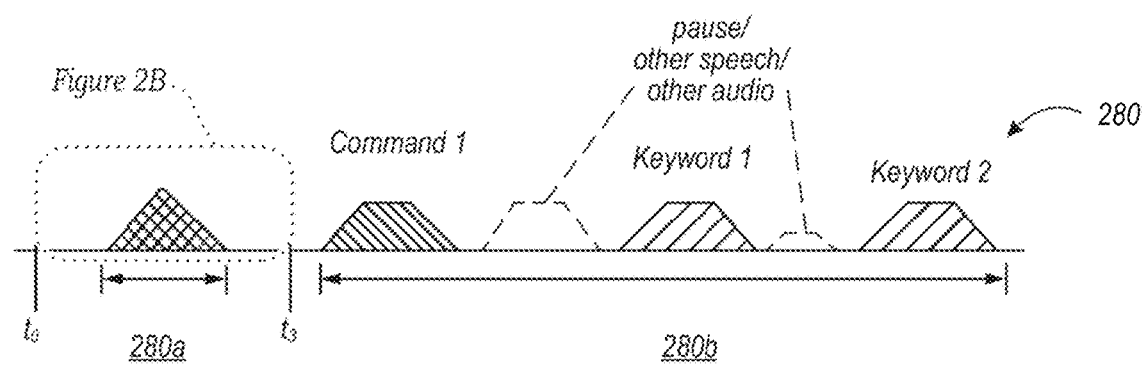
FIG. 2C is a diagram of an example voice input.

FIG. 2C is a diagram of an example voice input 280 that may be processed by an NMD or an NMD-equipped playback device. The voice input 280 may include a keyword portion 280a and an utterance portion 280b. The keyword portion 280a may include a wake word or a command keyword. In the case of a wake word, the keyword portion 280a corresponds to detected sound that caused a command-keyword event. The utterance portion 280b corresponds to detected sound that potentially comprises a user request following the keyword portion 280a. An utterance portion 280b can be processed to identify the presence of any words in detected-sound data by the NMD in response to the event caused by the keyword portion 280a. In various implementations, an underlying intent can be determined based on the words in the utterance portion 280b. In certain implementations, an underlying intent can also be based or at least partially based on certain words in the keyword portion 280a, such as when keyword portion includes a command keyword. In any case, the words may correspond to one or more commands, as well as a certain command and certain keywords. A keyword in the voice utterance portion 280b may be, for example, a word identifying a particular device or group in the MPS 100. For instance, in the illustrated example, the keywords in the voice utterance portion 280b may be one or more words identifying one or more zones in which the music is to be played, such as the Living Room and the Dining Room (FIG. 1A). In some cases, the utterance portion 280b may include additional information, such as detected pauses (e.g., periods of non-speech) between words spoken by a user, as shown in FIG. 2C. The pauses may demarcate the locations of separate commands, keywords, or other information spoke by the user within the utterance portion 280b.

Based on certain command criteria, the NMD and/or a remote VAS may take actions as a result of identifying one or more commands in the voice input. Command criteria may be based on the inclusion of certain keywords within the voice input, among other possibilities. Additionally, or alternatively, command criteria for commands may involve identification of one or more control-state and/or zone-state variables in conjunction with identification of one or more particular commands. Control-state variables may include, for example, indicators identifying a level of volume, a queue associated with one or more devices, and playback state, such as whether devices are playing a queue, paused, etc. Zone-state variables may include, for example, indicators identifying which, if any, zone players are grouped.

In some implementations, the MPS 100 is configured to temporarily reduce the volume of audio content that it is playing upon detecting a certain keyword, such as a wake word, in the keyword portion 280a. The MPS 100 may restore the volume after processing the voice input 280. Such a process can be referred to as ducking, examples of which are disclosed in U.S. patent application Ser. No. 15/438,749, incorporated by reference herein in its entirety.

Figure 2D:
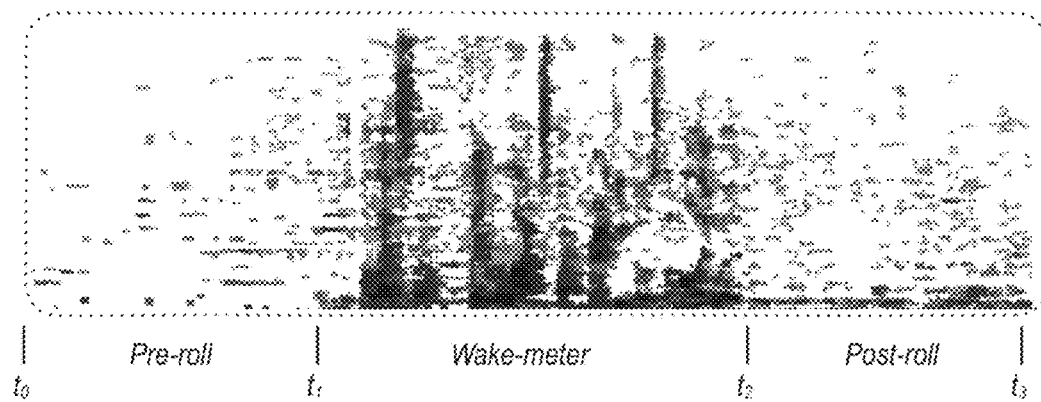
FIG. 2D is a graph depicting an example sound specimen in accordance with aspects of the disclosure.

FIG. 2D shows an example sound specimen. In this example, the sound specimen corresponds to the sound-data stream (e.g., one or more audio frames) associated with a spotted wake word or command keyword in the keyword portion 280a of FIG. 2A. As illustrated, the example sound specimen comprises sound detected in an NMD's environment (i) immediately before a wake or command word was spoken, which may be referred to as a pre-roll portion (between times $t_0$ and $t_1$), (ii) while a wake or command word was spoken, which may be referred to as a wake-meter portion (between times $t_1$ and $t_2$), and/or (iii) after the wake or command word was spoken, which may be referred to as a post-roll portion (between times $t_2$ and $t_3$). Other sound specimens are also possible. In various implementations, aspects of the sound specimen can be evaluated according to an acoustic model which aims to map mels/spectral features to phonemes in a given language model for further processing. For example, automatic speech recognition (ASR) may include such mapping for keyword detection. Wake-word detection engines, by contrast, may be precisely tuned to identify a specific wake-word, and a downstream action of invoking a VAS (e.g., by targeting only nonce words in the voice input processed by the playback device).

ASR for command keyword detection may be tuned to accommodate a wide range of keywords (e.g., 5, 10, 100, 1,000, 10,000 keywords). Command-keyword detection, in contrast to wake-word detection, may involve feeding ASR output to an onboard, local NLU which together with the ASR determine when command-keyword events have occurred. In some implementations described below, the local NLU may determine an intent based on one or more other keywords in the ASR output produced by a particular voice input. In these or other implementations, a playback device may act on a detected command-keyword event only when the playback devices determines that certain conditions have been met, such as environmental conditions (e.g., low background noise). In some embodiments, multiple devices within a single media playback system may have different onboard, local ASRs and/or NLUs, for example supporting different libraries of keywords.

b. Example Playback Device Configurations

FIGS. 3A-3E show example configurations of playback devices. Referring first to FIG. 3A, in some example instances, a single playback device may belong to a zone. For example, the playback device 102c (FIG. 1A) on the Patio may belong to Zone A. In some implementations described below, multiple playback devices may be "bonded" to form a "bonded pair," which together form a single zone. For example, the playback device 102f (FIG. 1A) named "Bed 1" in FIG. 3A may be bonded to the playback device 102g (FIG. 1A) named "Bed 2" in FIG. 3A to form Zone B. Bonded playback devices may have different playback responsibilities (e.g., channel responsibilities). In another implementation described below, multiple playback devices may be merged to form a single zone. For example, the playback device 102d named "Bookcase" may be merged with the playback device 102m named "Living Room" to form a single Zone C. The merged playback devices 102d and 102m may not be specifically assigned different playback responsibilities. That is, the merged playback devices 102d and 102m may, aside from playing audio content in synchrony, each play audio content as they would if they were not merged.

For purposes of control, each zone in the MPS 100 may be represented as a single user interface ("UI") entity. For example, as displayed by the controller devices 104, Zone A may be provided as a single entity named "Portable," Zone B may be provided as a single entity named "Stereo," and Zone C may be provided as a single entity named "Living Room."

In various embodiments, a zone may take on the name of one of the playback devices belonging to the zone. For example, Zone C may take on the name of the Living Room device 102m (as shown). In another example, Zone C may instead take on the name of the Bookcase device 102d. In a further example, Zone C may take on a name that is some combination of the Bookcase device 102d and Living Room device 102m. The name that is chosen may be selected by a user via inputs at a controller device 104. In some embodiments, a zone may be given a name that is different than the device(s) belonging to the zone. For example, Zone B in FIG. 3A is named "Stereo" but none of the devices in Zone B have this name. In one aspect, Zone B is a single UI entity representing a single device named "Stereo," composed of constituent devices "Bed 1" and "Bed 2." In one implementation, the Bed 1 device may be playback device 102f in the master bedroom 101b (FIG. 1A) and the Bed 2 device may be the playback device 102g also in the master bedroom 101h (FIG. 1A).

As noted above, playback devices that are bonded may have different playback responsibilities, such as playback responsibilities for certain audio channels. For example, as shown in FIG. 3B, the Bed 1 and Bed 2 devices 102f and 102g may be bonded so as to produce or enhance a stereo effect of audio content. In this example, the Bed 1 playback device 102f may be configured to play a left channel audio component, while the Bed 2 playback device 102g may be configured to play a right channel audio component. In some implementations, such stereo bonding may be referred to as "pairing."

Additionally, playback devices that are configured to be bonded may have additional and/or different respective speaker drivers. As shown in FIG. 3C, the playback device 102*b* named "Front" may be bonded with the playback device 102*k* named "SUB." The Front device 102*b* may render a range of mid to high frequencies, and the SUB device 102*k* may render low frequencies as, for example, a subwoofer. When unbonded, the Front device 102*b* may be configured to render a full range of frequencies. As another example, FIG. 3D shows the Front and SUB devices 102*b* and 102*k* further bonded with Right and Left playback devices 102*a* and 102*j*, respectively. In some implementations, the Right and Left devices 102*a* and 102*j* may form surround or "satellite" channels of a home theater system. The bonded playback devices 102*a*, 102*b*, 102*j*, and 102*k* may form a single Zone D (FIG. 3A).

In some implementations, playback devices may also be "merged." In contrast to certain bonded playback devices, playback devices that are merged may not have assigned playback responsibilities, but may each render the full range of audio content that each respective playback device is capable of. Nevertheless, merged devices may be represented as a single UI entity (i.e., a zone, as discussed above). For instance, FIG. 3E shows the playback devices 102*d* and 102*m* in the Living Room merged, which would result in these devices being represented by the single UI entity of Zone C. In one embodiment, the playback devices 102*d* and 102*m* may playback audio in synchrony, during which each outputs the full range of audio content that each respective playback device 102*d* and 102*m* is capable of rendering.

In some embodiments, a stand-alone NMD may be in a zone by itself. For example, the NMD 103*h* from FIG. 1A is named "Closet" and forms Zone I in FIG. 3A. An NMD may also be bonded or merged with another device so as to form a zone. For example, the NMD 103*f* named "Island" may be bonded with the playback device 102*i* Kitchen, which together form Zone F, which is also named "Kitchen." Additional details regarding assigning NMDs and playback devices as designated or default devices may be found, for example, in previously referenced U.S. patent application Ser. No. 15/438,749. In some embodiments, a stand-alone NMD may not be assigned to a zone.

Zones of individual, bonded, and/or merged devices may be arranged to form a set of playback devices that playback audio in synchrony. Such a set of playback devices may be referred to as a "group," "zone group," "synchrony group," or "playback group." In response to inputs provided via a controller device 104, playback devices may be dynamically grouped and ungrouped to form new or different groups that synchronously play back audio content. For example, referring to FIG. 3A, Zone A may be grouped with Zone B to form a zone group that includes the playback devices of the two zones. As another example, Zone A may be grouped with one or more other Zones C-I. The Zones A-I may be grouped and ungrouped in numerous ways. For example, three, four, five, or more (e.g., all) of the Zones A-I may be grouped. When grouped, the zones of individual and/or bonded playback devices may play back audio in synchrony with one another, as described in previously referenced U.S. Pat. No. 8,234,395. Grouped and bonded devices are example types of associations between portable and stationary playback devices that may be caused in response to a trigger event, as discussed above and described in greater detail below.

In various implementations, the zones in an environment may be assigned a particular name, which may be the default name of a zone within a zone group or a combination of the names of the zones within a zone group, such as "Dining Room+Kitchen," as shown in FIG. 3A. In some embodiments, a zone group may be given a unique name selected by a user, such as "Nick's Room," as also shown in FIG. 3A. The name "Nick's Room" may be a name chosen by a user over a prior name for the zone group, such as the room name "Master Bedroom."

Referring back to FIG. 2A, certain data may be stored in the memory 213 as one or more state variables that are periodically updated and used to describe the state of a playback zone, the playback device(s), and/or a zone group associated therewith. The memory 213 may also include the data associated with the state of the other devices of the MPS 100, which may be shared from time to time among the devices so that one or more of the devices have the most recent data associated with the system.

In some embodiments, the memory 213 of the playback device 102 may store instances of various variable types associated with the states. Variables instances may be stored with identifiers (e.g., tags) corresponding to type. For example, certain identifiers may be a first type "a1" to identify playback device(s) of a zone, a second type "b1" to identify playback device(s) that may be bonded in the zone, and a third type "c1" to identify a zone group to which the zone may belong. As a related example, in FIG. 1A, identifiers associated with the Patio may indicate that the Patio is the only playback device of a particular zone and not in a zone group. Identifiers associated with the Living Room may indicate that the Living Room is not grouped with other zones but includes bonded playback devices 102*a*, 102*b*, 102*j*, and 102*k*. Identifiers associated with the Dining Room may indicate that the Dining Room is part of Dining Room+Kitchen group and that devices 103*f* and 102*i* are bonded. Identifiers associated with the Kitchen may indicate the same or similar information by virtue of the Kitchen being part of the Dining Room+Kitchen zone group. Other example zone variables and identifiers are described below.

In yet another example, the MPS 100 may include variables or identifiers representing other associations of zones and zone groups, such as identifiers associated with Areas, as shown in FIG. 3A. An Area may involve a cluster of zone groups and/or zones not within a zone group. For instance, FIG. 3A shows a first area named "First Area" and a second area named "Second Area." The First Area includes zones and zone groups of the Patio, Den, Dining Room, Kitchen, and Bathroom. The Second Area includes zones and zone groups of the Bathroom, Nick's Room, Bedroom, and Living Room. In one aspect, an Area may be used to invoke a cluster of zone groups and/or zones that share one or more zones and/or zone groups of another cluster. In this respect, such an Area differs from a zone group, which does not share a zone with another zone group. Further examples of techniques for implementing Areas may be found, for example, in U.S. application Ser. No. 15/682,506 filed Aug. 21, 2017 and titled "Room Association Based on Name," and U.S. Pat. No. 8,483,853 filed Sep. 11, 2007, and titled "Controlling and manipulating groupings in a multi-zone media system." Each of these applications is incorporated herein by reference in its entirety. In some embodiments, the MPS 100 may not implement Areas, in which case the system may not store variables associated with Areas.

The memory 213 may be further configured to store other data. Such data may pertain to audio sources accessible by the playback device 102 or a playback queue that the playback device (or some other playback device(s)) may be associated with. In embodiments described below, the memory 213 is configured to store a set of command data for selecting a particular VAS when processing voice inputs. During operation, one or more playback zones in the environment of FIG. 1A may each be playing different audio content. For instance, the user may be grilling in the Patio zone and listening to hip hop music being played by the playback device 102c, while another user may be preparing food in the Kitchen zone and listening to classical music being played by the playback device 102i. In another example, a playback zone may play the same audio content in synchrony with another playback zone.

For instance, the user may be in the Office zone where the playback device 102n is playing the same hip-hop music that is being playing by playback device 102c in the Patio zone. In such a case, playback devices 102c and 102n may be playing the hip-hop in synchrony such that the user may seamlessly (or at least substantially seamlessly) enjoy the audio content that is being played out-loud while moving between different playback zones. Synchronization among playback zones may be achieved in a manner similar to that of synchronization among playback devices, as described in previously referenced U.S. Pat. No. 8,234,395.

As suggested above, the zone configurations of the MPS 100 may be dynamically modified. As such, the MPS 100 may support numerous configurations. For example, if a user physically moves one or more playback devices to or from a zone, the MPS 100 may be reconfigured to accommodate the change(s). For instance, if the user physically moves the playback device 102c from the Patio zone to the Office zone, the Office zone may now include both the playback devices 102c and 102n. In some cases, the user may pair or group the moved playback device 102c with the Office zone and/or rename the players in the Office zone using, for example, one of the controller devices 104 and/or voice input. As another example, if one or more playback devices 102 are moved to a particular space in the home environment that is not already a playback zone, the moved playback device(s) may be renamed or associated with a playback zone for the particular space.

Further, different playback zones of the MPS 100 may be dynamically combined into zone groups or split up into individual playback zones. For example, the Dining Room zone and the Kitchen zone may be combined into a zone group for a dinner party such that playback devices 102i and 102l may render audio content in synchrony. As another example, bonded playback devices in the Den zone may be split into (i) a television zone and (ii) a separate listening zone. The television zone may include the Front playback device 102b. The listening zone may include the Right, Left, and SUB playback devices 102a, 102j, and 102k, which may be grouped, paired, or merged, as described above. Splitting the Den zone in such a manner may allow one user to listen to music in the listening zone in one area of the living room space, and another user to watch the television in another area of the living room space. In a related example, a user may utilize either of the NMD 103a or 103b (FIG. 1B) to control the Den zone before it is separated into the television zone and the listening zone. Once separated, the listening zone may be controlled, for example, by a user in the vicinity of the NMD 103a, and the television zone may be controlled, for example, by a user in the vicinity of the NMD 103b. As described above, however, any of the NMDs 103 may be configured to control the various playback and other devices of the MPS 100.

c. Example Controller Devices

FIG. 4 is a functional block diagram illustrating certain aspects of a selected one of the controller devices 104 of the MPS 100 of FIG. 1A. Such controller devices may also be referred to herein as a "control device" or "controller." The controller device shown in FIG. 4 may include components that are generally similar to certain components of the network devices described above, such as a processor 412, memory 413 storing program software 414, at least one network interface 424, and one or more microphones 422. In one example, a controller device may be a dedicated controller for the MPS 100. In another example, a controller device may be a network device on which media playback system controller application software may be installed, such as for example, an iPhone™, iPad™ or any other smart phone, tablet, or network device (e.g., a networked computer such as a PC or Mac™).

The memory 413 of the controller device 104 may be configured to store controller application software and other data associated with the MPS 100 and/or a user of the system 100. The memory 413 may be loaded with instructions in software 414 that are executable by the processor 412 to achieve certain functions, such as facilitating user access, control, and/or configuration of the MPS 100. The controller device 104 is configured to communicate with other network devices via the network interface 424, which may take the form of a wireless interface, as described above.

In one example, system information (e.g., such as a state variable) may be communicated between the controller device 104 and other devices via the network interface 424. For instance, the controller device 104 may receive playback zone and zone group configurations in the MPS 100 from a playback device, an NMD, or another network device. Likewise, the controller device 104 may transmit such system information to a playback device or another network device via the network interface 424. In some cases, the other network device may be another controller device.

The controller device 104 may also communicate playback device control commands, such as volume control and audio playback control, to a playback device via the network interface 424. As suggested above, changes to configurations of the MPS 100 may also be performed by a user using the controller device 104. The configuration changes may include adding/removing one or more playback devices to/from a zone, adding/removing one or more zones to/from a zone group, forming a bonded or merged player, separating one or more playback devices from a bonded or merged player, among others.

As shown in FIG. 4, the controller device 104 also includes a user interface 440 that is generally configured to facilitate user access and control of the MPS 100. The user interface 440 may include a touch-screen display or other physical interface configured to provide various graphical controller interfaces, such as the controller interfaces 540a and 540b shown in FIGS. 5A and 5B. Referring to FIGS. 5A and 5B together, the controller interfaces 540a and 540b includes a playback control region 542, a playback zone region 543, a playback status region 544, a playback queue region 546, and a sources region 548. The user interface as shown is just one example of an interface that may be provided on a network device, such as the controller device shown in FIG. 4, and accessed by users to control a media playback system, such as the MPS 100. Other user interfaces of varying formats, styles, and interactive sequences may alternatively be implemented on one or more network devices to provide comparable control access to a media playback system.

The playback control region 542 (FIG. 5A) may include selectable icons (e.g., by way of touch or by using a cursor) that, when selected, cause playback devices in a selected playback zone or zone group to play or pause, fast forward, rewind, skip to next, skip to previous, enter/exit shuffle mode, enter/exit repeat mode, enter/exit cross fade mode, etc. The playback control region 542 may also include selectable icons that, when selected, modify equalization settings and/or playback volume, among other possibilities.

The playback zone region 543 (FIG. 5B) may include representations of playback zones within the MPS 100. The playback zones regions 543 may also include a representation of zone groups, such as the Dining Room+Kitchen zone group, as shown.

In some embodiments, the graphical representations of playback zones may be selectable to bring up additional selectable icons to manage or configure the playback zones in the MPS 100, such as a creation of bonded zones, creation of zone groups, separation of zone groups, and renaming of zone groups, among other possibilities.

For example, as shown, a "group" icon may be provided within each of the graphical representations of playback zones. The "group" icon provided within a graphical representation of a particular zone may be selectable to bring up options to select one or more other zones in the MPS 100 to be grouped with the particular zone. Once grouped, playback devices in the zones that have been grouped with the particular zone will be configured to play audio content in synchrony with the playback device(s) in the particular zone. Analogously, a "group" icon may be provided within a graphical representation of a zone group. In this case, the "group" icon may be selectable to bring up options to deselect one or more zones in the zone group to be removed from the zone group. Other interactions and implementations for grouping and ungrouping zones via a user interface are also possible. The representations of playback zones in the playback zone region 543 (FIG. 5B) may be dynamically updated as playback zone or zone group configurations are modified.

The playback status region 544 (FIG. 5A) may include graphical representations of audio content that is presently being played, previously played, or scheduled to play next in the selected playback zone or zone group. The selected playback zone or zone group may be visually distinguished on a controller interface, such as within the playback zone region 543 and/or the playback status region 544. The graphical representations may include track title, artist name, album name, album year, track length, and/or other relevant information that may be useful for the user to know when controlling the MPS 100 via a controller interface.

The playback queue region 546 may include graphical representations of audio content in a playback queue associated with the selected playback zone or zone group. In some embodiments, each playback zone or zone group may be associated with a playback queue comprising information corresponding to zero or more audio items for playback by the playback zone or zone group. For instance, each audio item in the playback queue may comprise a uniform resource identifier (URI), a uniform resource locator (URL), or some other identifier that may be used by a playback device in the playback zone or zone group to find and/or retrieve the audio item from a local audio content source or a networked audio content source, which may then be played back by the playback device.

In one example, a playlist may be added to a playback queue, in which case information corresponding to each audio item in the playlist may be added to the playback queue. In another example, audio items in a playback queue may be saved as a playlist. In a further example, a playback queue may be empty, or populated but "not in use" when the playback zone or zone group is playing continuously streamed audio content, such as Internet radio that may continue to play until otherwise stopped, rather than discrete audio items that have playback durations. In an alternative embodiment, a playback queue can include Internet radio and/or other streaming audio content items and be "in use" when the playback zone or zone group is playing those items. Other examples are also possible.

When playback zones or zone groups are "grouped" or "ungrouped," playback queues associated with the affected playback zones or zone groups may be cleared or re-associated. For example, if a first playback zone including a first playback queue is grouped with a second playback zone including a second playback queue, the established zone group may have an associated playback queue that is initially empty, that contains audio items from the first playback queue (such as if the second playback zone was added to the first playback zone), that contains audio items from the second playback queue (such as if the first playback zone was added to the second playback zone), or a combination of audio items from both the first and second playback queues. Subsequently, if the established zone group is ungrouped, the resulting first playback zone may be re-associated with the previous first playback queue or may be associated with a new playback queue that is empty or contains audio items from the playback queue associated with the established zone group before the established zone group was ungrouped. Similarly, the resulting second playback zone may be re-associated with the previous second playback queue or may be associated with a new playback queue that is empty or contains audio items from the playback queue associated with the established zone group before the established zone group was ungrouped. Other examples are also possible.

With reference still to FIGS. 5A and 5B, the graphical representations of audio content in the playback queue region 646 (FIG. 5A) may include track titles, artist names, track lengths, and/or other relevant information associated with the audio content in the playback queue. In one example, graphical representations of audio content may be selectable to bring up additional selectable icons to manage and/or manipulate the playback queue and/or audio content represented in the playback queue. For instance, a represented audio content may be removed from the playback queue, moved to a different position within the playback queue, or selected to be played immediately, or after any currently playing audio content, among other possibilities. A playback queue associated with a playback zone or zone group may be stored in a memory on one or more playback devices in the playback zone or zone group, on a playback device that is not in the playback zone or zone group, and/or some other designated device. Playback of such a playback queue may involve one or more playback devices playing back media items of the queue, perhaps in sequential or random order.

The sources region 548 may include graphical representations of selectable audio content sources and/or selectable voice assistants associated with a corresponding VAS. The VASes may be selectively assigned. In some examples, multiple VASes, such as AMAZON's Alexa, MICROSOFT's Cortana, etc., may be invokable by the same NMD. In some embodiments, a user may assign a VAS exclusively to one or more NMDs. For example, a user may assign a first VAS to one or both of the playback devices 102a and 102b in the Living Room shown in FIG. 1A, and a second VAS to the NMD 103f in the Kitchen. Other examples are possible.

d. Example Audio Content Sources

The audio sources in the sources region 548 may be audio content sources from which audio content may be retrieved and played by the selected playback zone or zone group.

One or more playback devices in a zone or zone group may be configured to retrieve for playback audio content (e.g., according to a corresponding URI or URL for the audio content) from a variety of available audio content sources. In one example, audio content may be retrieved by a playback device directly from a corresponding audio content source (e.g., via a line-in connection). In another example, audio content may be provided to a playback device over a network via one or more other playback devices or network devices. As described in greater detail below, in some embodiments, audio content may be provided by one or more media content services.

Example audio content sources may include a memory of one or more playback devices in a media playback system such as the MPS 100 of FIG. 1, local music libraries on one or more network devices (e.g., a controller device, a network-enabled personal computer, or a networked-attached storage ("NAS")), streaming audio services providing audio content via the Internet (e.g., cloud-based music services), or audio sources connected to the media playback system via a line-in input connection on a playback device or network device, among other possibilities.

In some embodiments, audio content sources may be added or removed from a media playback system such as the MPS 100 of FIG. 1A. In one example, an indexing of audio items may be performed whenever one or more audio content sources are added, removed, or updated. Indexing of audio items may involve scanning for identifiable audio items in all folders/directories shared over a network accessible by playback devices in the media playback system and generating or updating an audio content database comprising metadata (e.g., title, artist, album, track length, among others) and other associated information, such as a URI or URL for each identifiable audio item found. Other examples for managing and maintaining audio content sources may also be possible.

Figure 6:
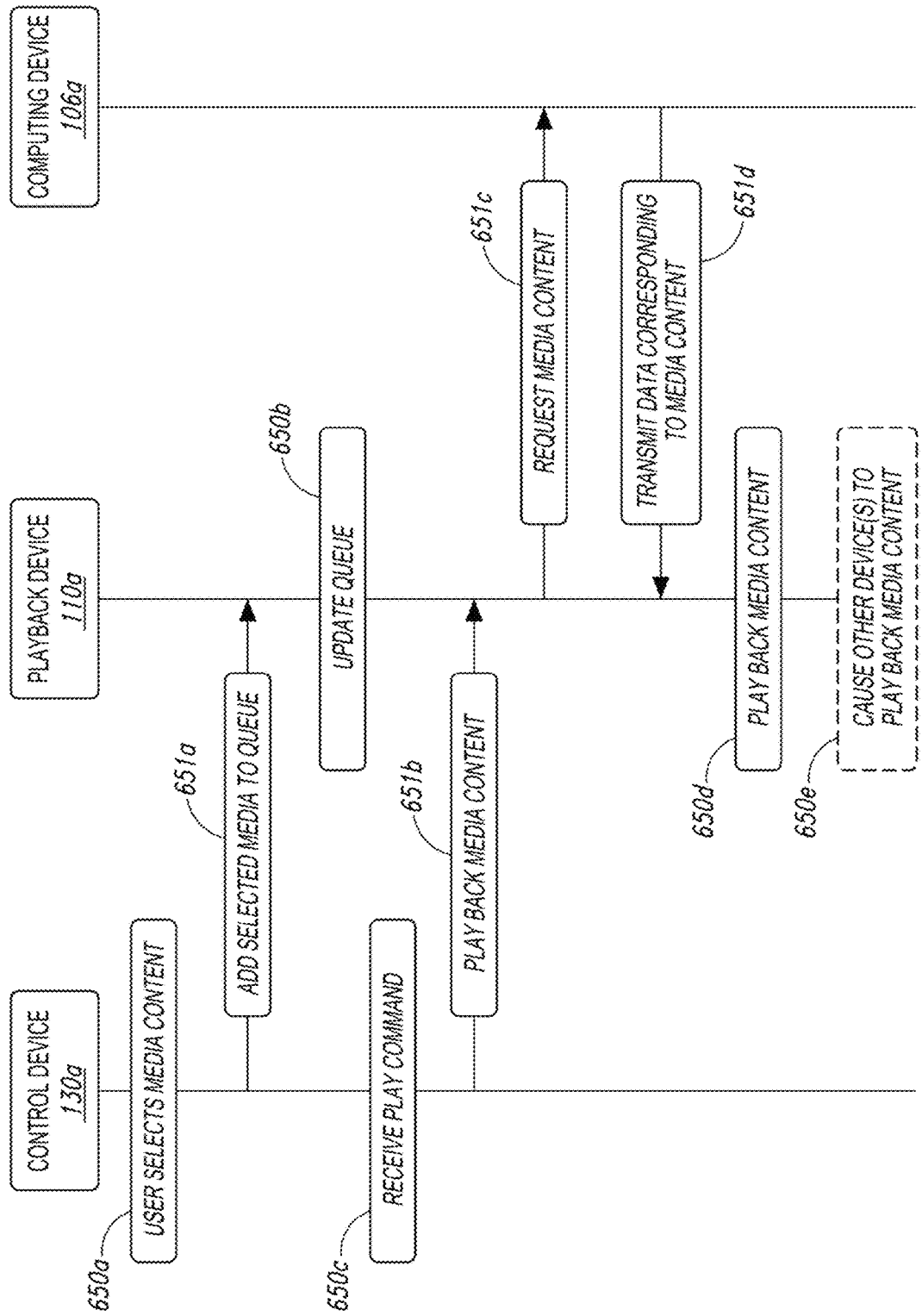
FIG. 6 is a message flow diagram of a media playback system.

FIG. 6 is a message flow diagram illustrating data exchanges between devices of the MPS 100. At step 650a, the MPS 100 receives an indication of selected media content (e.g., one or more songs, albums, playlists, podcasts, videos, stations) via the control device 104. The selected media content can comprise, for example, media items stored locally on or more devices (e.g., the audio source 105 of FIG. 1C) connected to the media playback system and/or media items stored on one or more media service servers (one or more of the remote computing devices 106 of FIG. 1B). In response to receiving the indication of the selected media content, the control device 104 transmits a message 651a to the playback device 102 (FIGS. 1A-1C) to add the selected media content to a playback queue on the playback device 102.

At step 650b, the playback device 102 receives the message 651a and adds the selected media content to the playback queue for play back.

At step 650c, the control device 104 receives input corresponding to a command to play back the selected media content. In response to receiving the input corresponding to the command to play back the selected media content, the control device 104 transmits a message 651b to the playback device 102 causing the playback device 102 to play back the selected media content. In response to receiving the message 651b, the playback device 102 transmits a message 651c to the computing device 106 requesting the selected media content. The computing device 106, in response to receiving the message 651c, transmits a message 651d comprising data (e.g., audio data, video data, a URL, a URI) corresponding to the requested media content.

At step 650d, the playback device 102 receives the message 651d with the data corresponding to the requested media content and plays back the associated media content.

At step 650e, the playback device 102 optionally causes one or more other devices to play back the selected media content. In one example, the playback device 102 is one of a bonded zone of two or more players (FIG. 1M). The playback device 102 can receive the selected media content and transmit all or a portion of the media content to other devices in the bonded zone. In another example, the playback device 102 is a coordinator of a group and is configured to transmit and receive timing information from one or more other devices in the group. The other one or more devices in the group can receive the selected media content from the computing device 106, and begin playback of the selected media content in response to a message from the playback device 102 such that all of the devices in the group play back the selected media content in synchrony.

III. Example Command-Keyword Eventing

Figure 7A:
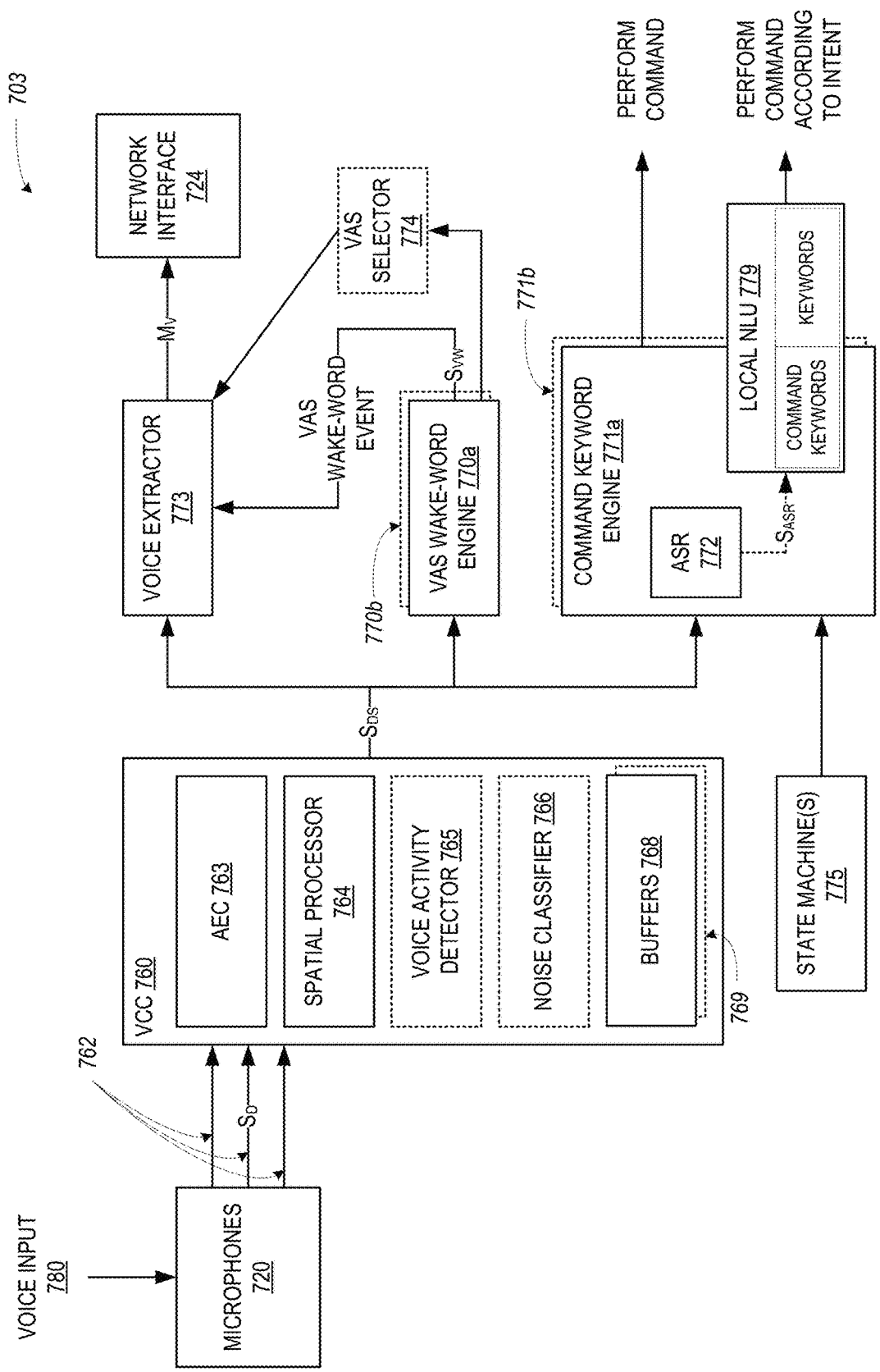
FIG. 7A is a functional block diagram of certain components of an example network microphone device in accordance with aspects of the disclosure.

FIG. 7A is functional block diagram showing aspects of an NMD 703 configured in accordance with embodiments of the disclosure. The NMD 703 may be generally similar to the NMD 103 and include similar components. As described in more detail below, the NMD 703 (FIG. 7A) is configured to handle certain voice inputs locally, without necessarily transmitting data representing the voice input to a voice assistant service. However, the NMD 703 is also configured to process other voice inputs using a voice assistant service.

Referring to FIG. 7A, the NMD 703 includes voice capture components ("VCC") 760, a VAS wake-word engine 770a, and a voice extractor 773. The VAS wake-word engine 770a and the voice extractor 773 are operably coupled to the VCC 760. The NMD 703 further comprises a command-keyword engine 771a operably coupled to the VCC 760.

The NMD 703 further includes microphones 720 and the at least one network interface 724 as described above and may also include other components, such as audio amplifiers, a user interface, etc., which are not shown in FIG. 7A for purposes of clarity. The microphones 720 of the NMD 703 are configured to provide detected sound, $S_D$, from the environment of the NMD 703 to the VCC 760. The detected sound $S_D$ may take the form of one or more analog or digital signals. In example implementations, the detected sound $S_D$ may be composed of a plurality signals associated with respective channels 762 that are fed to the VCC 760.

Each channel 762 may correspond to a particular microphone 720. For example, an NMD having six microphones may have six corresponding channels. Each channel of the detected sound $S_D$ may bear certain similarities to the other channels but may differ in certain regards, which may be due to the position of the given channel's corresponding microphone relative to the microphones of other channels. For example, one or more of the channels of the detected sound $S_D$ may have a greater signal to noise ratio ("SNR") of speech to background noise than other channels.

As further shown in FIG. 7A, the VCC 760 includes an AEC 763, a spatial processor 764, and one or more buffers 768. In operation, the AEC 763 receives the detected sound $S_D$ and filters or otherwise processes the sound to suppress echoes and/or to otherwise improve the quality of the detected sound $S_D$. That processed sound may then be passed to the spatial processor 764.

The spatial processor 764 is typically configured to analyze the detected sound $S_D$ and identify certain characteristics, such as a sound's amplitude (e.g., decibel level), frequency spectrum, directionality, etc. In one respect, the spatial processor 764 may help filter or suppress ambient noise in the detected sound $S_D$ from potential user speech based on similarities and differences in the constituent channels 762 of the detected sound $S_D$, as discussed above. As one possibility, the spatial processor 764 may monitor metrics that distinguish speech from other sounds. Such metrics can include, for example, energy within the speech band relative to background noise and entropy within the speech band—a measure of spectral structure—which is typically lower in speech than in most common background noise. In some implementations, the spatial processor 764 may be configured to determine a speech presence probability, examples of such functionality are disclosed in U.S. patent application Ser. No. 15/984,073, filed May 18, 2018, titled "Linear Filtering for Noise-Suppressed Speech Detection," which is incorporated herein by reference in its entirety.

In operation, the one or more buffers 768—one or more of which may be part of or separate from the memory 213 (FIG. 2A)—capture data corresponding to the detected sound $S_D$. More specifically, the one or more buffers 768 capture detected-sound data that was processed by the upstream AEC 764 and spatial processor 764.

The network interface 724 may then provide this information to a remote server that may be associated with the MPS 100. In one aspect, the information stored in the additional buffer 769 does not reveal the content of any speech but instead is indicative of certain unique features of the detected sound itself. In a related aspect, the information may be communicated between computing devices, such as the various computing devices of the MPS 100, without necessarily implicating privacy concerns. In practice, the MPS 100 can use this information to adapt and fine tune voice processing algorithms, including sensitivity tuning as discussed below. In some implementations the additional buffer may comprise or include functionality similar to lookback buffers disclosed, for example, in U.S. patent application Ser. No. 15/989,715, filed May 25, 2018, titled "Determining and Adapting to Changes in Microphone Performance of Playback Devices"; U.S. patent application Ser. No. 16/141,875, filed Sep. 25, 2018, titled "Voice Detection Optimization Based on Selected Voice Assistant Service"; and U.S. patent application Ser. No. 16/138,111, filed Sep. 21, 2018, titled "Voice Detection Optimization Using Sound Metadata," which are incorporated herein by reference in their entireties.

In any event, the detected-sound data forms a digital representation (i.e., sound-data stream), $S_{DS}$, of the sound detected by the microphones 720. In practice, the sound-data stream $S_{DS}$ may take a variety of forms. As one possibility, the sound-data stream $S_{DS}$ may be composed of frames, each of which may include one or more sound samples. The frames may be streamed (i.e., read out) from the one or more buffers 768 for further processing by downstream components, such as the VAS wake-word engines 770 and the voice extractor 773 of the NMD 703.

In some implementations, at least one buffer 768 captures detected-sound data utilizing a sliding window approach in which a given amount (i.e., a given window) of the most recently captured detected-sound data is retained in the at least one buffer 768 while older detected sound data is overwritten when it falls outside of the window. For example, at least one buffer 768 may temporarily retain 20 frames of a sound specimen at given time, discard the oldest frame after an expiration time, and then capture a new frame, which is added to the 19 prior frames of the sound specimen.

In practice, when the sound-data stream $S_{DS}$ is composed of frames, the frames may take a variety of forms having a variety of characteristics. As one possibility, the frames may take the form of audio frames that have a certain resolution (e.g., 16 bits of resolution), which may be based on a sampling rate (e.g., 44,100 Hz). Additionally, or alternatively, the frames may include information corresponding to a given sound specimen that the frames define, such as metadata that indicates frequency response, power input level, SNR, microphone channel identification, and/or other information of the given sound specimen, among other examples. Thus, in some embodiments, a frame may include a portion of sound (e.g., one or more samples of a given sound specimen) and metadata regarding the portion of sound. In other embodiments, a frame may only include a portion of sound (e.g., one or more samples of a given sound specimen) or metadata regarding a portion of sound.

In any case, downstream components of the NMD 703 may process the sound-data stream $S_{DS}$. For instance, the VAS wake-word engines 770 are configured to apply one or more identification algorithms to the sound-data stream $S_{DS}$ (e.g., streamed sound frames) to spot potential wake words in the detected-sound $S_D$. This process may be referred to as automatic speech recognition. The VAS wake-word engine 770a and command-keyword engine 771a apply different identification algorithms corresponding to their respective wake words, and further generate different events based on detecting a wake word in the detected sound $S_D$.

Example wake word detection algorithms accept audio as input and provide an indication of whether a wake word is present in the audio. Many first- and third-party wake word detection algorithms are known and commercially available. For instance, operators of a voice service may make their algorithm available for use in third-party devices. Alternatively, an algorithm may be trained to detect certain wake-words.

For instance, when the VAS wake-word engine 770a detects a potential VAS wake word, the VAS work-word engine 770a provides an indication of a "VAS wake-word event" (also referred to as a "VAS wake-word trigger"). In the illustrated example of FIG. 7A, the VAS wake word engine 770a outputs a signal, $S_{VW}$, that indicates the occurrence of a VAS wake-word event to the voice extractor 773.

In multi-VAS implementations, the NMD 703 may include a VAS selector 774 (shown in dashed lines) that is generally configured to direct extraction by the voice extractor 773 and transmission of the sound-data stream $S_{DS}$ to the appropriate VAS when a given wake-word is identified by a particular wake-word engine (and a corresponding wake-word trigger), such as the VAS wake-word engine 770a and at least one additional VAS wake-word engine 770b (shown in dashed lines). In such implementations, the NMD 703 may include multiple, different VAS wake word engines and/or voice extractors, each supported by a respective VAS.

Similar to the discussion above, each VAS wake-word engine 770 may be configured to receive as input the sound-data stream $S_{DS}$ from the one or more buffers 768 and apply identification algorithms to cause a wake-word trigger for the appropriate VAS. Thus, as one example, the VAS wake-word engine 770a may be configured to identify the wake word "Alexa" and cause the NMD 703 to invoke the AMAZON VAS when "Alexa" is spotted. As another example, the wake-word engine 770b may be configured to identify the wake word "Ok, Google" and cause the NMD 520 to invoke the GOOGLE VAS when "Ok, Google" is spotted. In single-VAS implementations, the VAS selector 774 may be omitted.

In response to the VAS wake-word event (e.g., in response to the signal $S_{VW}$ indicating the wake-word event), the voice extractor 773 is configured to receive and format (e.g., packetize) the sound-data stream $S_{DS}$. For instance, the voice extractor 773 packetizes the frames of the sound-data stream $S_{DS}$ into messages. The voice extractor 773 transmits or streams these messages, $M_V$, that may contain voice input in real time or near real time to a remote VAS via the network interface 724.

The VAS is configured to process the sound-data stream $S_{DS}$ contained in the messages $M_V$ sent from the NMD 703. More specifically, the NMD 703 is configured to identify a voice input 780 based on the sound-data stream $S_{DS}$. As described in connection with FIG. 2C, the voice input 780 may include a keyword portion and an utterance portion. The keyword portion corresponds to detected sound that caused a wake-word event, or leads to a command-keyword event when one or more certain conditions, such as certain playback conditions, are met. For instance, when the voice input 780 includes a VAS wake word, the keyword portion corresponds to detected sound that caused the wake-word engine 770a to output the wake-word event signal $S_{VW}$ to the voice extractor 773. The utterance portion in this case corresponds to detected sound that potentially comprises a user request following the keyword portion.

When a VAS wake-word event occurs, the VAS may first process the keyword portion within the sound data stream $S_{DS}$ to verify the presence of a VAS wake word. In some instances, the VAS may determine that the keyword portion comprises a false wake word (e.g., the word "Election" when the word "Alexa" is the target VAS wake word). In such an occurrence, the VAS may send a response to the NMD 703 with an instruction for the NMD 703 to cease extraction of sound data, which causes the voice extractor 773 to cease further streaming of the detected-sound data to the VAS. The VAS wake-word engine 770a may resume or continue monitoring sound specimens until it spots another potential VAS wake word, leading to another VAS wake-word event. In some implementations, the VAS does not process or receive the keyword portion but instead processes only the utterance portion.

In any case, the VAS processes the utterance portion to identify the presence of any words in the detected-sound data and to determine an underlying intent from these words. The words may correspond to one or more commands, as well as certain keywords. The keyword may be, for example, a word in the voice input identifying a particular device or group in the MPS 100. For instance, in the illustrated example, the keyword may be one or more words identifying one or more zones in which the music is to be played, such as the Living Room and the Dining Room (FIG. 1A).

To determine the intent of the words, the VAS is typically in communication with one or more databases associated with the VAS (not shown) and/or one or more databases (not shown) of the MPS 100. Such databases may store various user data, analytics, catalogs, and other information for natural language processing and/or other processing. In some implementations, such databases may be updated for adaptive learning and feedback for a neural network based on voice-input processing. In some cases, the utterance portion may include additional information, such as detected pauses (e.g., periods of non-speech) between words spoken by a user, as shown in FIG. 2C. The pauses may demarcate the locations of separate commands, keywords, or other information spoke by the user within the utterance portion.

After processing the voice input, the VAS may send a response to the MPS 100 with an instruction to perform one or more actions based on an intent it determined from the voice input. For example, based on the voice input, the VAS may direct the MPS 100 to initiate playback on one or more of the playback devices 102, control one or more of these playback devices 102 (e.g., raise/lower volume, group/ungroup devices, etc.), or turn on/off certain smart devices, among other actions. After receiving the response from the VAS, the wake-word engine 770a of the NMD 703 may resume or continue to monitor the sound-data stream $S_{DS1}$ until it spots another potential wake-word, as discussed above.

In general, the one or more identification algorithms that a particular VAS wake-word engine, such as the VAS wake-word engine 770a, applies are configured to analyze certain characteristics of the detected sound stream $S_{DS}$ and compare those characteristics to corresponding characteristics of the particular VAS wake-word engine's one or more particular VAS wake words. For example, the wake-word engine 770a may apply one or more identification algorithms to spot temporal and spectral characteristics in the detected sound stream $S_{DS}$ that match the temporal and spectral characteristics of the engine's one or more wake words, and thereby determine that the detected sound $S_D$ comprises a voice input including a particular VAS wake word.

In some implementations, the one or more identification algorithms may be third-party identification algorithms (i.e., developed by a company other than the company that provides the NMD 703). For instance, operators of a voice service (e.g., AMAZON) may make their respective algorithms (e.g., identification algorithms corresponding to AMAZON's ALEXA) available for use in third-party devices (e.g., the NMDs 103), which are then trained to identify one or more wake words for the particular voice assistant service. Additionally, or alternatively, the one or more identification algorithms may be first-party identification algorithms that are developed and trained to identify certain wake words that are not necessarily particular to a given voice service. Other possibilities also exist.

As noted above, the NMD 703 also includes a command-keyword engine 771a in parallel with the VAS wake-word engine 770a. Like the VAS wake-word engine 770a, the command-keyword engine 771a may apply one or more identification algorithms corresponding to one or more wake words. A "command-keyword event" is generated when a particular command keyword is identified in the detected sound $S_D$. In contrast to the nonce words typically as utilized as VAS wake words, command keywords function as both the activation word and the command itself. For instance, example command keywords may correspond to playback commands (e.g., "play," "pause," "skip," etc.) as well as control commands ("turn on"), among other examples. Under appropriate conditions, based on detecting one of these command keywords, the NMD 703 performs the corresponding command.

The command-keyword engine 771a can employ an automatic speech recognizer 772. The ASR 772 is configured to output phonetic or phonemic representations, such as text corresponding to words, based on sound in the sound-data stream $S_{DS}$ to text. For instance, the ASR 772 may transcribe spoken words represented in the sound-data stream $S_{DS}$ to one or more strings representing the voice input 780 as text. The command-keyword engine 771 can feed ASR output (labeled as $S_{ASR}$) to a local natural language unit (NLU) 779 that identifies particular keywords as being command keywords for invoking command-keyword events, as described below.

As noted above, in some example implementations, the NMD 703 is configured to perform natural language processing, which may be carried out using an onboard natural language understanding processor, referred to herein as a natural language unit (NLU) 779. The local NLU 779 is configured to analyze text output of the ASR 772 of the command-keyword engine 771a to spot (i.e., detect or identify) keywords in the voice input 780. In FIG. 7A, this output is illustrated as the signal $S_{ASR}$. The local NLU 779 includes a library of keywords (i.e., words and phrases) corresponding to respective commands and/or parameters.

In one aspect, the library of the local NLU 779 includes command keywords. When the local NLU 779 identifies a command keyword in the signal $S_{ASR}$, the command-keyword engine 771a generates a command-keyword event and performs a command corresponding to the command keyword in the signal $S_{ASR}$, assuming that one or more conditions corresponding to that command keyword are satisfied.

Further, the library of the local NLU 779 may also include keywords corresponding to parameters. The local NLU 779 may then determine an underlying intent from the matched keywords in the voice input 780. For instance, if the local NLU matches the keywords "David Bowie" and "kitchen" in combination with a play command, the local NLU 779 may determine an intent of playing David Bowie in the Kitchen 101h on the playback device 102i. In contrast to a processing of the voice input 780 by a cloud-based VAS, local processing of the voice input 780 by the local NLU 779 may be relatively less sophisticated, as the NLU 779 does not have access to the relatively greater processing capabilities and larger voice databases that a VAS generally has access to. As described in greater detail below, in some implementations multiple NMDs of a single media playback system may be equipped with different libraries of their respective local NLUs 779. Voice input captured via a first NMD may be processed for detection of keywords stored in any one of the libraries of the various NMDs of the media playback system. As a result, the presence of multiple NMDs can increase the total available keywords for local detection. In various embodiments, the libraries of the NMDs can be identical, partially overlapping, or completely non-overlapping.

In some examples, the local NLU 779 may determine an intent with one or more slots, which correspond to respective keywords. For instance, referring back to the play David Bowie in the Kitchen example, when processing the voice input, the local NLU 779 may determine that an intent is to play music (e.g., intent=playMusic), while a first slot includes David Bowie as target content (e.g., slot1=DavidBowie) and a second slot includes the Kitchen 101h as the target playback device (e.g., slot2=kitchen). Here, the intent (to "playMusic") is based on the command keyword and the slots are parameters modifying the intent to a particular target content and playback device.

Within examples, the command-keyword engine 771a outputs a signal that indicates the occurrence of a command-keyword event to the local NLU 779. In response to the command-keyword event (e.g., in response to the signal indicating the command-keyword event), the local NLU 779 is configured to receive and process the signal $S_{ASR}$. In particular, the local NLU 779 looks at the words within the signal $S_{ASR}$ to find keywords that match keywords in the library of the local NLU 779. In some embodiments, the signal $S_{ASR}$ can be transmitted from the NMD to another NMD for processing via its local NLU. For example, the ASR 772 of a first NMD may generate output signal $S_{ASR}$ which can include, for example, one or more strings representing a transcription of the voice input 780. This signal $S_{ASR}$ may then be transmitted to the local NLU of a second, separate NMD for processing to identify an intent based on the $S_{ASR}$. In various embodiments, this transmission of the signal $S_{ASR}$ to a second, separate NMD can be performed instead of or in parallel with passing the signal $S_{ASR}$ to the local NLU 779 of the first NMD.

Some error in performing local automatic speech recognition is expected. Within examples, the ASR 772 may generate a confidence score when transcribing spoken words to text, which indicates how closely the spoken words in the voice input 780 matches the sound patterns for that word. In some implementations, generating a command-keyword event is based on the confidence score for a given command keyword. For instance, the command-keyword engine 771a may generate a command-keyword event when the confidence score for a given sound exceeds a given threshold value (e.g., 0.5 on a scale of 0-1, indicating that the given sound is more likely than not the command keyword). Conversely, when the confidence score for a given sound is at or below the given threshold value, the command-keyword engine 771a does not generate the command-keyword event.

Similarly, some error in performing keyword matching is expected. Within examples, the local NLU may generate a confidence score when determining an intent, which indicates how closely the transcribed words in the signal $S_{ASR}$ match the corresponding keywords in the library of the local NLU. In some implementations, performing an operation according to a determined intent is based on the confidence score for keywords matched in the signal $S_{ASR}$. For instance, the NMD 703 may perform an operation according to a determined intent when the confidence score for a given sound exceeds a given threshold value (e.g., 0.5 on a scale of 0-1, indicating that the given sound is more likely than not the command keyword). Conversely, when the confidence score for a given intent is at or below the given threshold value, the NMD 703 does not perform the operation according to the determined intent.

In some embodiments, keyword matching can be performed via NLUs of two or more different NMDs on a local network, and the results can be compared or otherwise combined to cross-check the results, thereby increasing confidence and reducing the rate of false positives. For example, a first NMD may identify a keyword in voice input with a first confidence score. A second NMD may separately perform keyword detection on the same voice input (either by separately capturing the same user speech or by receiving sound input data from the first NMD transmitted over the local area network). The second NMD may transmit the results of its keyword matching to the first NMD for comparison and evaluation. If, for example, the first and second NMD each identified the same keyword, a false positive is less likely. If, by contrast, the first and second NMD each identified a different keyword (or if one did not identify a keyword at all), then a false positive is more likely, and the first NMD may decline to take further action. In some embodiments, the identified keywords and/or any associated confidence scores can be compared between the two NMDs to make a final intent determination. In some embodiments, the respective NLUs of the first and second NMDs can be similarly or identically configured (e.g., having the same libraries of keywords), or optionally the NLUs can be configured differently (e.g., having different libraries of keywords). Although these examples are described with respect to two NMDs, this comparison can be extended to three, four, five, or more different NMDs.

In some embodiments, such cross-checking can be performed not between two different NMDs, but between different sound data streams $S_{DS}$ obtained via a single NMD 703. For example, the NMD 703 can be configured to generate a first sound-data stream $S_{DS}$ representing data obtained from a first subset of the microphones 720, and to generate a second sound-data stream $S_{DS}$ representing data obtained from a second subset of the microphones 720 that is different from the first. In an NMD having six microphones 720, the first sound-data stream $S_{DS}$ may be generated using data from microphones 1-3, while the second sound-data stream $S_{DS}$ may be generated using data from microphones 4-6. Optionally, in some embodiments the subsets of the microphones can include some overlapping microphones—for example the first sound-data stream $S_{DS}$ can include data from microphones 1-4 and the second sound data stream can include data from microphones 3-6. Additionally, in some embodiments there may be three, four, five, or more different sound-data streams $S_{DS}$ generated using different subsets of microphones or other variations in processing of voice input. Optionally, in some instances a sound-data stream $S_{DS}$ can include input from individual microphones of different NMDs, for example combining inputs from two microphones of a first NMD and two microphones of a second NMD. However generated, these different sound-data streams $S_{DS}$ can then be separately evaluated by the command-keyword engine 771 and the results can be compared or otherwise combined. For example, the NMD 703 may perform an action if and only if each of the local NLU 779 identifies the same keyword(s) in each of the evaluated sound-data streams $S_{DS}$.

As noted above, in some implementations, a phrase may be used as a command keyword, which provides additional syllables to match (or not match). For instance, the phrase "play me some music" has more syllables than "play," which provides additional sound patterns to match to words. Accordingly, command keywords that are phrases may generally be less prone to false wake word triggers.

As indicated above, the NMD 703 generates a command-keyword event (and performs a command corresponding to the detected command keyword) only when certain conditions corresponding to a detected command keyword are met. These conditions are intended to lower the prevalence of false positive command-keyword events. For instance, after detecting the command keyword "skip," the NMD 703 generates a command-keyword event (and skips to the next track) only when certain playback conditions indicating that a skip should be performed are met. These playback conditions may include, for example, (i) a first condition that a media item is being played back, (ii) a second condition that a queue is active, and (iii) a third condition that the queue includes a media item subsequent to the media item being played back. If any of these conditions are not satisfied, the command-keyword event is not generated (and no skip is performed).

The NMD 703 includes the one or more state machine(s) 775 to facilitate determining whether the appropriate conditions are met. The state machine 775 transitions between a first state and a second state based on whether one or more conditions corresponding to the detected command keyword are met. In particular, for a given command keyword corresponding to a particular command requiring one or more particular conditions, the state machine 775 transitions into a first state when one or more particular conditions are satisfied and transitions into a second state when at least one condition of the one or more particular conditions is not satisfied.

Within example implementations, the command conditions are based on states indicated in state variables. As noted above, the devices of the MPS 100 may store state variables describing the state of the respective device. For instance, the playback devices 102 may store state variables indicating the state of the playback devices 102, such as the audio content currently playing (or paused), the volume levels, network connection status, and the like). These state variables are updated (e.g., periodically, or based on an event (i.e., when a state in a state variable changes)) and the state variables further can be shared among the devices of the MPS 100, including the NMD 703.

Similarly, the NMD 703 may maintain these state variables (either by virtue of being implemented in a playback device or as a stand-alone NMD). The state machine 775 monitors the states indicated in these state variables, and determines whether the states indicated in the appropriate state variables indicate that the command condition(s) are satisfied. Based on these determinations, the state machine 775 transitions between the first state and the second state, as described above.

In some implementations, the command-keyword engine 771 may be disabled unless certain conditions have been met via the state machines, and/or the available keywords to be identified by the command-keyword engine can be limited based on conditions as reflected via the state machines. As one example, the first state and the second state of the state machine 775 may operate as enable/disable toggles to the command-keyword engine 771a. In particular, while a state machine 775 corresponding to a particular command keyword is in the first state, the state machine 775 enables the command-keyword engine 771a of the particular command keyword. Conversely, while the state machine 775 corresponding to the particular command keyword is in the second state, the state machine 775 disables the command-keyword engine 771a of the particular command keyword. Accordingly, the disabled command-keyword engine 771a ceases analyzing the sound-data stream $S_{DS}$. In such cases when at least one command condition is not satisfied, the NMD 703 may suppress generation of command-keyword event when the command-keyword engine 771a detects a command keyword. Suppressing generation may involve gating, blocking or otherwise preventing output from the command-keyword engine 771a from generating the command-keyword event. Alternatively, suppressing generation may involve the NMD 703 ceasing to feed the sound data stream $S_{DS}$ to the ASR 772. Such suppression prevents a command corresponding to the detected command keyword from being performed when at least one command condition is not satisfied. In such embodiments, the command-keyword engine 771a may continue analyzing the sound data stream $S_{DS}$ while the state machine 775 is in the first state, but command-keyword events are disabled.

Other example conditions may be based on the output of a voice activity detector ("VAD") 765. The VAD 765 is configured to detect the presence (or lack thereof) of voice activity in the sound-data stream $S_{DS}$. In particular, the VAD 765 may analyze frames corresponding to the pre-roll portion of the voice input 780 (FIG. 2D) with one or more voice detection algorithms to determine whether voice activity was present in the environment in certain time windows prior to a keyword portion of the voice input 780.

The VAD 765 may utilize any suitable voice activity detection algorithms. Example voice detection algorithms involve determining whether a given frame includes one or more features or qualities that correspond to voice activity, and further determining whether those features or qualities diverge from noise to a given extent (e.g., if a value exceeds a threshold for a given frame). Some example voice detection algorithms involve filtering or otherwise reducing noise in the frames prior to identifying the features or qualities.

In some examples, the VAD 765 may determine whether voice activity is present in the environment based on one or more metrics. For example, the VAD 765 can be configured distinguish between frames that include voice activity and frames that don't include voice activity. The frames that the VAD determines have voice activity may be caused by speech regardless of whether it near- or far-field. In this example and others, the VAD 765 may determine a count of frames in the pre-roll portion of the voice input 780 that indicate voice activity. If this count exceeds a threshold percentage or number of frames, the VAD 765 may be configured to output a signal or set a state variable indicating that voice activity is present in the environment. Other metrics may be used as well in addition to, or as an alternative to, such a count.

The presence of voice activity in an environment may indicate that a voice input is being directed to the NMD 73. Accordingly, when the VAD 765 indicates that voice activity is not present in the environment (perhaps as indicated by a state variable set by the VAD 765) this may be configured as one of the command conditions for the command keywords. When this condition is met (i.e., the VAD 765 indicates that voice activity is present in the environment), the state machine 775 will transition to the first state to enable performing commands based on command keywords, so long as any other conditions for a particular command keyword are satisfied.

Further, in some implementations, the NMD 703 may include a noise classifier 766. The noise classifier 766 is configured to determine sound metadata (frequency response, signal levels, etc.) and identify signatures in the sound metadata corresponding to various noise sources. The noise classifier 766 may include a neural network or other mathematical model configured to identify different types of noise in detected sound data or metadata. One classification of noise may be speech (e.g., far-field speech). Another classification may be a specific type of speech, such as background speech, and example of which is described in greater detail with reference to FIG. 8. Background speech may be differentiated from other types of voice-like activity, such as more general voice activity (e.g., cadence, pauses, or other characteristics) of voice-like activity detected by the VAD 765.

For example, analyzing the sound metadata can include comparing one or more features of the sound metadata with known noise reference values or a sample population data with known noise. For example, any features of the sound metadata such as signal levels, frequency response spectra, etc. can be compared with noise reference values or values collected and averaged over a sample population. In some examples, analyzing the sound metadata includes projecting the frequency response spectrum onto an eigenspace corresponding to aggregated frequency response spectra from a population of NMDs. Further, projecting the frequency response spectrum onto an eigenspace can be performed as a pre-processing step to facilitate downstream classification.

In various embodiments, any number of different techniques for classification of noise using the sound metadata can be used, for example machine learning using decision trees, or Bayesian classifiers, neural networks, or any other classification techniques. Alternatively or additionally, various clustering techniques may be used, for example K-Means clustering, mean-shift clustering, expectation-maximization clustering, or any other suitable clustering technique. Techniques to classify noise may include one or more techniques disclosed in U.S. application Ser. No. 16/227,308 filed Dec. 20, 2018, and titled "Optimization of Network Microphone Devices Using Noise Classification," which is herein incorporated by reference in its entirety.

Figure 8:
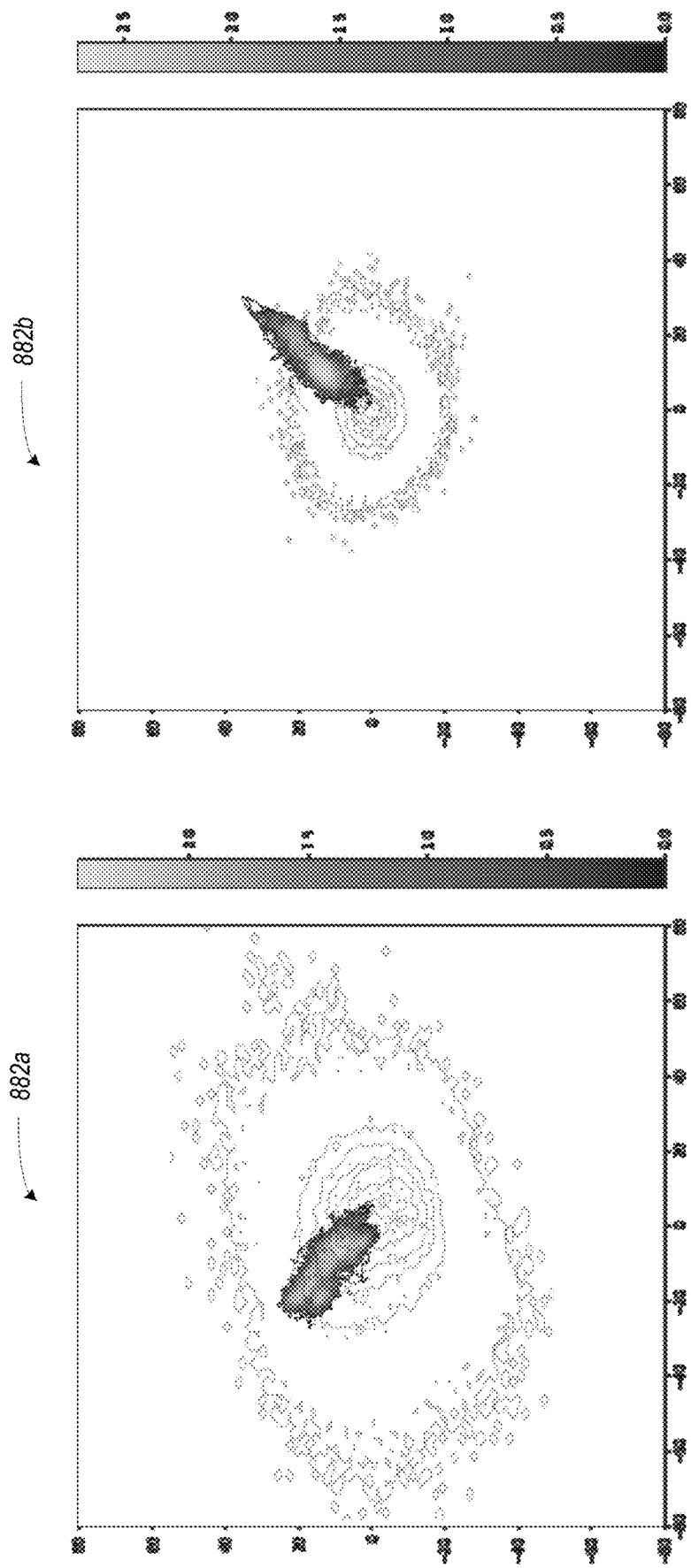
FIG. 8 shows example noise graphs illustrating analyzed sound metadata associated with background speech.

To illustrate, FIG. 8 shows a first plot 882a and a second plot 882b. The first plot 882a and the second plot 882b show analyzed sound metadata associated with background speech. These signatures shown in the plots are generated using principal component analysis (PCA). Collected data from a variety of NMDs provides an overall distribution of possible frequency response spectra. In general, principal component analysis can be used to find the orthogonal basis that describes the variance in all the field data. This eigenspace is reflected in the contours shown in the plots of FIG. 8. Each dot in the plot represents a known noise value (e.g., a single frequency response spectrum from an NMD exposed to the noted noise source) that is projected onto the eigenspace. As seen in FIG. 8, these known noise values cluster together when projected onto the eigenspace. In this example, the FIG. 8 plots are representative of a four-vector analysis, where each vector corresponds to a respective feature. The features collectively are a signature for background speech.

Referring back to FIG. 7A, in some implementations, the additional buffer 769 (shown in dashed lines) may store information (e.g., metadata or the like) regarding the detected sound $S_D$ that was processed by the upstream AEC 763 and spatial processor 764. This additional buffer 769 may be referred to as a "sound metadata buffer." Examples of such sound metadata include: (1) frequency response data, (2) echo return loss enhancement measures, (3) voice direction measures; (4) arbitration statistics; and/or (5) speech spectral data. In example implementations, the noise classifier 766 may analyze the sound metadata in the buffer 769 to classify noise in the detected sound $S_D$.

As noted above, one classification of sound may be background speech, such as speech indicative of far-field speech and/or speech indicative of a conversation not involving the NMD 703. The noise classifier 766 may output a signal and/or set a state variable indicating that background speech is present in the environment. The presence of voice activity (i.e., speech) in the pre-roll portion of the voice input 780 indicates that the voice input 780 might not be directed to the NMD 703, but instead be conversational speech within the environment. For instance, a household member might speak something like "our kids should have a play date soon" without intending to direct the command keyword "play" to the NMD 703.

Further, when the noise classifier indicates that background speech is present is present in the environment, this condition may disable the command-keyword engine 771a. In some implementations, the condition of background speech being absent in the environment (perhaps as indicated by a state variable set by the noise classifier 766) is configured as one of the command conditions for the command keywords. Accordingly, the state machine 775 will not transition to the first state when the noise classifier 766 indicates that background speech is present in the environment.

Further, the noise classifier 766 may determine whether background speech is present in the environment based on one or more metrics. For example, the noise classifier 766 may determine a count of frames in the pre-roll portion of the voice input 780 that indicate background speech. If this count exceeds a threshold percentage or number of frames, the noise classifier 766 may be configured to output the signal or set the state variable indicating that background speech is present in the environment. Other metrics may be used as well in addition to, or as an alternative to, such a count.

Within example implementations, the NMD 703 may support a plurality of command keywords. To facilitate such support, the command-keyword engine 771a may implement multiple identification algorithms corresponding to respective command keywords. Alternatively, the NMD 703 may implement additional command-keyword engines 771b configured to identify respective command keywords. Yet further, the library of the local NLU 779 may include a plurality of command keywords and be configured to search for text patterns corresponding to these command keywords in the signal $S_{ASR}$.

Further, command keywords may require different conditions. For instance, the conditions for "skip" may be different than the conditions for "play" as "skip" may require that the condition that a media item is being played back and play may require the opposite condition that a media item is not being played back. To facilitate these respective conditions, the NMD 703 may implement respective state machines 775 corresponding to each command keyword. Alternatively, the NMD 703 may implement a state machine 775 having respective states for each command keyword. Other examples are possible as well.

Figure 7B:
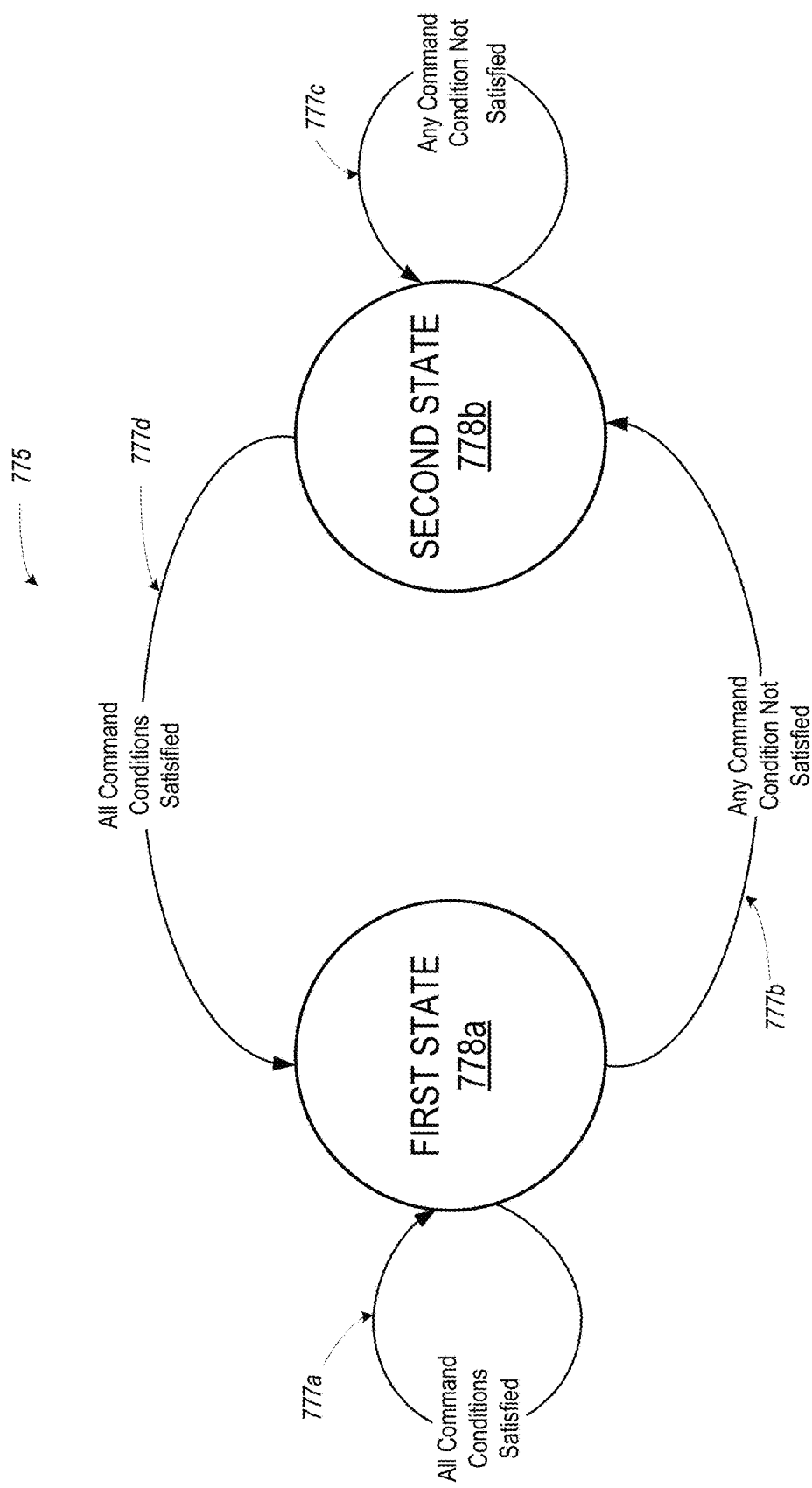
FIG. 7B is a functional block diagram illustrating an example state machine in accordance with aspects of the disclosure.

To illustrate exemplary state machine operation, FIG. 7B is a block diagram illustrating the state machine 775 for an example command keyword requiring one or more command conditions. At 777a, the state machine 775 remains in the first state 778a while all the command conditions are satisfied. While the state machine 775 remains in the first state 778a (and all command conditions are met), the NMD 703 will generate a command-keyword event when the command keyword is detected by the command-keyword engine 771a.

At 777b, the state machine 775 transitions into the second state 778b when any command condition is not satisfied. At 777c, the state machine 775 remains in the second state 778b while any command condition is not satisfied. While the state machine 775 remains in the second state 778b, the NMD 703 will not act on the command-keyword event when the command keyword is detected by the command-keyword engine 771a.

Referring back to FIG. 7A, in some examples, the one or more additional command-keyword engines 771b may include custom command-keyword engines. Cloud service providers, such as streaming audio services, may provide a custom keyword engine pre-configured with identification algorithms configured to spot service-specific command keywords. These service-specific command keywords may include commands for custom service features and/or custom names used in accessing the service.

For instance, the NMD 703 may include a particular streaming audio service (e.g., Apple Music) command-keyword engine 771b. This particular command-keyword engine 771b may be configured to detect command keywords specific to the particular streaming audio service and generate streaming audio service wake word events. For instance, one command keyword may be "Friends Mix," which corresponds to a command to play back a custom playlist generated from playback histories of one or more "friends" within the particular streaming audio service.

In some embodiments, different NMDs 703 of the same media playback system 100 can have different additional custom command-keyword engines 771b. For example, a first NMD may include a custom command-keyword engine 771b having an NLU configured with a library of keywords configured for a particular streaming audio service (e.g., Apple Music) while a second NMD includes a custom-command keyword engine 771b having an NLU configured with a library of keywords configured to a different streaming audio service (e.g., Spotify). In operation, voice input received at either NMD may be transmitted to the other NMD for processing, such that in combination the media playback system may effectively evaluate voice input for keywords with the benefit of multiple different custom command-keyword engines 771b distributed among multiple different NMDs 703.

A custom command-keyword engine 771b may be relatively more prone to false wake words than the VAS wake-word engine 770a, as generally the VAS wake-word engine 770a is more sophisticated than a custom command-keyword engine 771b. To mitigate this, custom command keywords may require one or more conditions to be satisfied before generating a custom command-keyword event. Further, in some implementations, in an effort to reduce the prevalence of false positives, multiple conditions may be imposed as a requirement to include a custom command-keyword engine 771b in the NMD 703.

These custom command keyword conditions may include service-specific conditions. For instance, command keywords corresponding to premium features or playlists may require a subscription as a condition. As another example, custom command keywords corresponding to a particular streaming audio service may require media items from that streaming audio service in the playback queue. Other conditions are possible as well.

To gate custom command-keyword engines based on the custom command keyword conditions, the NMD 703 may additional state machines 775 corresponding to each custom command keyword. Alternatively, the NMD 703 may implement a state machine 775 having respective states for each custom command keyword. Other examples are possible as well. These custom command conditions may depend on the state variables maintained by the devices within the MPS 100, and may also depend on state variables or other data structures representing a state of a user account of a cloud service, such as a streaming audio service.

FIGS. 9A and 9B show a table 985 illustrating exemplary command keywords and corresponding conditions. As shown in the Figures, example command keywords may include cognates having similar intent and requiring similar conditions. For instance, the "next" command keyword has cognates of "skip" and "forward," each of which invokes a skip command under appropriate conditions. The conditions shown in the table 985 are illustrative; various implementations may use different conditions.

Referring back to FIG. 7A, in example embodiments, the VAS wake-word engine 770a and the command-keyword engine 771a may take a variety of forms. For example, the VAS wake-word engine 770a and the command-keyword engine 771a may take the form of one or more modules that are stored in memory of the NMD 703 (e.g., the memory 112b of FIG. 1F). As another example, the VAS wake-word engine 770a and the command-keyword engine 771a may take the form of a general purposes or special-purpose processor, or modules thereof. In this respect, multiple wake word engines 770 and 771 may be part of the same component of the NMD 703 or each wake-word engine 770 and 771 may take the form of a component that is dedicated for the particular wake-word engine. Other possibilities also exist.

To further reduce false positives, the command-keyword engine 771a may utilize a relative low sensitivity compared with the VAS wake-word engine 770a. In practice, a wake-word engine may include a sensitivity level setting that is modifiable. The sensitivity level may define a degree of similarity between a word identified in the detected sound stream $S_{DS1}$ and the wake-word engine's one or more particular wake words that is considered to be a match (i.e., that triggers a VAS wake-word or command-keyword event). In other words, the sensitivity level defines how closely, as one example, the spectral characteristics in the detected sound stream $S_{DS2}$ must match the spectral characteristics of the engine's one or more wake words to be a wake-word trigger.

In this respect, the sensitivity level generally controls how many false positives that the VAS wake-word engine 770a and command-keyword engine 771a identifies. For example, if the VAS wake-word engine 770a is configured to identify the wake-word "Alexa" with a relatively high sensitivity, then false wake words of "Election" or "Lexus" may cause the wake-word engine 770a to flag the presence of the wake-word "Alexa." In contrast, if the command-keyword engine 771a is configured with a relatively low sensitivity, then the false wake words of "may" or "day" would not cause the command-keyword engine 771a to flag the presence of the command keyword "Play."

In practice, a sensitivity level may take a variety of forms. In example implementations, a sensitivity level takes the form of a confidence threshold that defines a minimum confidence (i.e., probability) level for a wake-word engine that serves as a dividing line between triggering or not triggering a wake-word event when the wake-word engine is analyzing detected sound for its particular wake word. In this regard, a higher sensitivity level corresponds to a lower confidence threshold (and more false positives), whereas a lower sensitivity level corresponds to a higher confidence threshold (and fewer false positives). For example, lowering a wake-word engine's confidence threshold configures it to trigger a wake-word event when it identifies words that have a lower likelihood that they are the actual particular wake word, whereas raising the confidence threshold configures the engine to trigger a wake-word event when it identifies words that have a higher likelihood that they are the actual particular wake word. Within examples, a sensitivity level of the command-keyword engine 771a may be based on more or more confidence scores, such as the confidence score in spotting a command keyword and/or a confidence score in determining an intent. Other examples of sensitivity levels are also possible.

In example implementations, sensitivity level parameters (e.g., the range of sensitivities) for a particular wake-word engine can be updated, which may occur in a variety of manners. As one possibility, a VAS or other third-party provider of a given wake-word engine may provide to the NMD 703 a wake-word engine update that modifies one or more sensitivity level parameters for the given VAS wake-word engine 770a. By contrast, the sensitive level parameters of the command-keyword engine 771a may be configured by the manufacturer of the NMD 703 or by another cloud service (e.g., for a custom wake-word engine 771b).

Notably, within certain examples, the NMD 703 foregoes sending any data representing the detected sound $S_D$ (e.g., the messages $M_V$) to a VAS when processing a voice input 780 including a command keyword. In implementations including the local NLU 779, the NMD 703 can further process the voice utterance portion of the voice input 780 (in addition to the keyword word portion) without necessarily sending the voice utterance portion of the voice input 780 to the VAS. Accordingly, speaking a voice input 780 (with a command keyword) to the NMD 703 may provide increased privacy relative to other NMDs that process all voice inputs using a VAS.

As indicated above, the keywords in the library of the local NLU 779 can correspond to parameters. These parameters may define to perform the command corresponding to the detected command keyword. When keywords are recognized in the voice input 780, the command corresponding to the detected command keyword is performed according to parameters corresponding to the detected keywords.

For instance, an example voice input 780 may be "play music at low volume" with "play" being the command keyword portion (corresponding to a playback command) and "music at low volume" being the voice utterance portion. When analyzing this voice input 780, the NLU 779 may recognize that "low volume" is a keyword in its library corresponding to a parameter representing a certain (low) volume level. Accordingly, the NLU 779 may determine an intent to play at this lower volume level. Then, when performing the playback command corresponding to "play," this command is performed according to the parameter representing a certain volume level.

In a second example, another example voice input 780 may be "play my favorites in the Kitchen" with "play" again being the command keyword portion (corresponding to a playback command) and "my favorites in the Kitchen" as the voice utterance portion. When analyzing this voice input 780, the NLU 779 may recognize that "favorites" and "Kitchen" match keywords in its library. In particular, "favorites" corresponds to a first parameter representing particular audio content (i.e., a particular playlist that includes a user's favorite audio tracks) while "Kitchen" corresponds to a second parameter representing a target for the playback command (i.e., the kitchen 101h zone. Accordingly, the NLU 779 may determine an intent to play this particular playlist in the kitchen 101h zone.

In a third example, a further example voice input 780 may be "volume up" with "volume" being the command keyword portion (corresponding to a volume adjustment command) and "up" being the voice utterance portion. When analyzing this voice input 780, the NLU 779 may recognize that "up" is a keyword in its library corresponding to a parameter representing a certain volume increase (e.g., a 10-point increase on a 100-point volume scale). Accordingly, the NLU 779 may determine an intent to increase volume. Then, when performing the volume adjustment command corresponding to "volume," this command is performed according to the parameter representing the certain volume increase.

Within examples, certain command keywords are functionally linked to a subset of the keywords within the library of the local NLU 779, which may hasten analysis. For instance, the command keyword "skip" may be functionality linked to the keywords "forward" and "backward" and their cognates. Accordingly, when the command keyword "skip" is detected in a given voice input 780, analyzing the voice utterance portion of that voice input 780 with the local NLU 779 may involve determining whether the voice input 780 includes any keywords that match these functionally linked keywords (rather than determining whether the voice input 780 includes any keywords that match any keyword in the library of the local NLU 779). Since vastly fewer keywords are checked, this analysis is relatively quicker than a full search of the library. By contrast, a nonce VAS wake word such as "Alexa" provides no indication as to the scope of the accompanying voice input.

Some commands may require one or more parameters, as such the command keyword alone does not provide enough information to perform the corresponding command. For example, the command keyword "volume" might require a parameter to specify a volume increase or decrease, as the intent of "volume" of volume alone is unclear. As another example, the command keyword "group" may require two or more parameters identifying the target devices to group.

Accordingly, in some example implementations, when a given command keyword is detected in the voice input 780 by the command-keyword engine 771*a*, the local NLU 779 may determine whether the voice input 780 includes keywords matching keywords in the library corresponding to the required parameters. If the voice input 780 does include keywords matching the required parameters, the NMD 703 proceeds to perform the command (corresponding to the given command keyword) according to the parameters specified by the keywords.

However, if the voice input 780 does include keywords matching the required parameters for the command, the NMD 703 may prompt the user to provide the parameters. For instance, in a first example, the NMD 703 may play an audible prompt such as "I've heard a command, but I need more information" or "Can I help you with something?" Alternatively, the NMD 703 may send a prompt to a user's personal device via a control application (e.g., the software components 132*c* of the control device(s) 104).

In further examples, the NMD 703 may play an audible prompt customized to the detected command keyword. For instance, after detecting a command keyword corresponding to a volume adjustment command (e.g., "volume"), the audible prompt may include a more specific request such as "Do you want to adjust the volume up or down?" As another example, for a grouping command corresponding to the command keyword "group," the audible prompt may be "Which devices do you want to group?" Supporting such specific audible prompts may be made practicable by supporting a relatively limited number of command keywords (e.g., less than 100), but other implementations may support more command keywords with the trade-off of requiring additional memory and processing capability.

Within additional examples, when a voice utterance portion does not include keywords corresponding to one or more required parameters, the NMD 703 may perform the corresponding command according to one or more default parameters. For instance, if a playback command does not include keywords indicating target playback devices 102 for playback, the NMD 703 may default to playback on the NMD 703 itself (e.g., if the NMD 703 is implemented within a playback device 102) or to playback on one or more associated playback devices 102 (e.g., playback devices 102 in the same room or zone as the NMD 703). Further, in some examples, the user may configure default parameters using a graphical user interface (e.g., user interface 430) or voice user interface. For example, if a grouping command does not specify the playback devices 102 to group, the NMD 703 may default to instructing two or more pre-configured default playback devices 102 to form a synchrony group. Default parameters may be stored in data storage (e.g., the memory 112*b* (FIG. 1F)) and accessed when the NMD 703 determines that keywords exclude certain parameters. Other examples are possible as well.

In some cases, the NMD 703 sends the voice input 780 to a VAS when the local NLU 779 is unable to process the voice input 780 (e.g., when the local NLU is unable to find matches to keywords in the library, or when the local NLU 779 has a low confidence score as to intent). In an example, to trigger sending the voice input 780, the NMD 703 may generate a bridging event, which causes the voice extractor 773 to process the sound-data stream $S_D$, as discussed above. That is, the NMD 703 generates a bridging event to trigger the voice extractor 773 without a VAS wake-word being detected by the VAS wake word engine 770*a* (instead based on a command keyword in the voice input 780, as well as the NLU 779 being unable to process the voice input 780).

Before sending the voice input 780 to the VAS (e.g., via the messages $M_V$), the NMD 703 may obtain confirmation from the user that the user acquiesces to the voice input 780 being sent to the VAS. For instance, the NMD 703 may play an audible prompt to send the voice input to a default or otherwise configured VAS, such as "I'm sorry, I didn't understand that. May I ask Alexa?" In another example, the NMD 703 may play an audible prompt using a VAS voice (i.e., a voice that is known to most users as being associated with a particular VAS), such as "Can I help you with something?" In such examples, generation of the bridging event (and triggering of the voice extractor 773) is contingent on a second affirmative voice input 780 from the user.

Within certain example implementations, the local NLU 779 may process the signal $S_{ASR}$ without necessarily a command-keyword event being generated by the command-keyword engine 771*a* (i.e., directly). That is, the automatic speech recognition 772 may be configured to perform automatic speech recognition on the sound-data stream $S_D$, which the local NLU 779 processes for matching keywords without requiring a command-keyword event. If keywords in the voice input 780 are found to match keywords corresponding to a command (possibly with one or more keywords corresponding to one or more parameters), the NMD 703 performs the command according to the one or more parameters.

Further, in such examples, the local NLU 779 may process the signal $S_{ASR}$ directly only when certain conditions are met. In particular, in some embodiments, the local NLU 779 processes the signal $S_{ASR}$ only when the state machine 775 is in the first state. The certain conditions may include a condition corresponding to no background speech in the environment. An indication of whether background speech is present in the environment may come from the noise classifier 766. As noted above, the noise classifier 766 may be configured to output a signal or set a state variable indicating that far-field speech is present in the environment. Further, another condition may correspond to voice activity in the environment. The VAD 765 may be configured to output a signal or set a state variable indicating that voice activity is present in the environment. Similarly, the prevalence of false positive detection of commands with a direct processing approach may be mitigated using the conditions determined by the state machine 775.

In some examples, the library of the local NLU 779 is partially customized to the individual user(s). In a first aspect, the library may be customized to the devices that are within the household of the NMD (e.g., the household within the environment 101 (FIG. 1A)). For instance, the library of the local NLU may include keywords corresponding to the names of the devices within the household, such as the zone names of the playback devices 102 in the MPS 100. In a second aspect, the library may be customized to the users of the devices within the household. For example, the library of the local NLU 779 may include keywords corresponding to names or other identifiers of a user's preferred playlists, artists, albums, and the like. Then, the user may refer to these names or identifiers when directing voice inputs to the command-keyword engine 771a and the local NLU 779. In some embodiments, different NMDs 703 of the same media playback system 100 can have different NLUs 779 with different customized libraries. For example, a first NMD may include a first subset of device and zone names, and a second NMD may include a second subset of device and zone names.

Within example implementations, the NMD 703 may populate the library of the local NLU 779 locally within the network 111 (FIG. 1B). As noted above, the NMD 703 may maintain or have access to state variables indicating the respective states of devices connected to the network 111 (e.g., the playback devices 104). These state variables may include names of the various devices. For instance, the kitchen 101h may include the playback device 102b, which are assigned the zone name "Kitchen." The NMD 703 may read these names from the state variables and include them in the library of the local NLU 779 by training the local NLU 779 to recognize them as keywords. The keyword entry for a given name may then be associated with the corresponding device in an associated parameter (e.g., by an identifier of the device, such as a MAC address or IP address). The NMD 703 can then use the parameters to customize control commands and direct the commands to a particular device.

In further examples, the NMD 703 may populate the library by discovering devices connected to the network 111. For instance, the NMD 703 may transmit discovery requests via the network 111 according to a protocol configured for device discovery, such as universal plug-and-play (UPnP) or zero-configuration networking. Devices on the network 111 may then respond to the discovery requests and exchange data representing the device names, identifiers, addresses and the like to facilitate communication and control via the network 111. The NMD 703 may read these names from the exchanged messages and include them in the library of the local NLU 779 by training the local NLU 779 to recognize them as keywords.

In further examples, the NMD 703 may populate the library using the cloud. To illustrate, FIG. 10 is a schematic diagram of the MPS 100 and a cloud network 902. The cloud network 902 includes cloud servers 906, identified separately as media playback system control servers 906a, streaming audio service servers 906b, and IOT cloud servers 906c. The streaming audio service servers 906b may represent cloud servers of different streaming audio services. Similarly, the IOT cloud servers 906c may represent cloud servers corresponding to different cloud services supporting smart devices 990 in the MPS 100.

One or more communication links 903a, 903b, and 903c (referred to hereinafter as "the links 903") communicatively couple the MPS 100 and the cloud servers 906. The links 903 can include one or more wired networks and one or more wireless networks (e.g., the Internet). Further, similar to the network 111 (FIG. 1B), a network 911 communicatively couples the links 903 and at least a portion of the devices (e.g., one or more of the playback devices 102, NMDs 103 and 703, control devices 104, and/or smart devices 990) of the MPS 100.

In some implementations, the media playback system control servers 906a facilitate populating the library of local NLU 779 with the NMD(s) 703 (representing one or more of the NMD 703 (FIG. 7A) within the MPS 100). In an example, the media playback system control servers 906a may receive data representing a request to populate the library of a local NLU 779 from the NMD 703. Based on this request, the media playback system control servers 906a may communicate with the streaming audio service servers 906b and/or IOT cloud servers 906c to obtain keywords specific to the user.

In some embodiments, different NMDs 703 of the same media playback system 100 can have different NLUs 779 with different customized libraries. For example, a first NMD may have an NLU 779 with a library of keywords associated with IOT commands while a second NMD may have an NLU 779 with a library of keywords associated with media streaming services commands. In some embodiments, the library of an NLU 779 can include two or more partitions having different sets of keywords. For example, an NLU 779 can include a first partition of keywords associated with transport commands, and a second partition of keywords associated with IOT commands. One or more of such partitions can be populated using the cloud as described above. For example, the NLU 779 can have an IOT partition in its library that contains keywords populated by one or more of the IOT cloud servers 906c, while a different NLU can have a media streaming service partition in its library that contains keywords populated by one or more of the audio service servers 906b.

In some examples, the media playback system control servers 906a may utilize user accounts and/or user profiles in obtaining keywords specific to the user. As noted above, a user of the MPS 100 may set-up a user profile to define settings and other information within the MPS 100. The user profile may then in turn be registered with user accounts of one or more streaming audio services to facilitate streaming audio from such services to the playback devices 102 of the MPS 100.

Through use of these registered streaming audio services, the streaming audio service servers 906b may collect data indicating a user's saved or preferred playlists, artists, albums, tracks, and the like, either via usage history or via user input (e.g., via a user input designating a media item as saved or a favorite). This data may be stored in a database on the streaming audio service servers 906b to facilitate providing certain features of the streaming audio service to the user, such as custom playlists, recommendations, and similar features. Under appropriate conditions (e.g., after receiving user permission), the streaming audio service servers 906b may share this data with the media playback system control servers 906a over the links 903b.

Accordingly, within examples, the media playback system control servers 906a may maintain or have access to data indicating a user's saved or preferred playlists, artists, albums, tracks, genres, and the like. If a user has registered their user profile with multiple streaming audio services, the saved data may include saved playlists, artists, albums, tracks, and the like from two or more streaming audio services. Further, the media playback system control servers 906a may develop a more complete understanding of the user's preferred playlists, artists, albums, tracks, and the like by aggregating data from the two or more streaming audio services, as compared with a streaming audio service that only has access to data generated through use of its own service.

Moreover, in some implementations, in addition to the data shared from the streaming audio service servers 906b, the media playback system control servers 906a may collect usage data from the MPS 100 over the links 903a, after receiving user permission. This may include data indicating a user's saved or preferred media items on a zone basis. Different types of music may be preferred in different rooms.

For instance, a user may prefer upbeat music in the Kitchen 101*h* and more mellow music to assist with focus in the Office 101*e*.

Using the data indicating a user's saved or preferred playlists, artists, albums, tracks, and the like, the media playback system control servers 906*a* may identify names of playlists, artists, albums, tracks, and the like that the user is likely to refer to when providing playback commands to the NMDs 703 via voice input. Data representing these names can then be transmitted via the links 903*a* and the network 904 to the NMDs 703 and then added to the library of the local NLU 779 as keywords. For instance, the media playback system control servers 906*a* may send instructions to the NMDs 703 to include certain names as keywords in the library of the local NLU 779. Alternatively, the NMDs 703 (or another device of the MPS 100) may identify names of playlists, artists, albums, tracks, and the like that the user is likely to refer to when providing playback commands to the NMDs 703 via voice input and then include these names in the library of the local NLU 779.

Due to such customization, similar voice inputs may result in different operations being performed when the voice input is processed by the local NLU 779 as compared with processing by a VAS. For instance, a first voice input of "Alexa, play me my favorites in the Office" may trigger a VAS wake word event, as it includes a VAS wake word ("Alexa"). A second voice input of "Play me my favorites in the Office" may trigger a command keyword, as it includes a command keyword ("play"). Accordingly, the first voice input is sent by the NMD 703 to the VAS, while the second voice input is processed by the local NLU 779.

While these voice inputs are nearly identical, they may cause different operations. In particular, the VAS may, to the best of its ability, determine a first playlist of audio tracks to add to a queue of the playback device 102*f* in the office 101*e*. Similarly, the local NLU 779 may recognize keywords "favorites" and "kitchen" in the second voice input. Accordingly, the NMD 703 performs the voice command of "play" with parameters of <favorites playlist> and <kitchen 101*h* zone>, which causes a second playlist of audio tracks to be added to the queue of the playback device 102*f* in the office 101*e*. However, the second playlist of audio tracks may include a more complete and/or more accurate collection of the user's favorite audio tracks, as the second playlist of audio tracks may draw on data indicating a user's saved or preferred playlists, artists, albums, and tracks from multiple streaming audio services, and/or the usage data collected by the media playback system control servers 906*a*. In contrast, the VAS may draw on its relatively limited conception of the user's saved or preferred playlists, artists, albums, and tracks when determining the first playlist.

Figure 11:
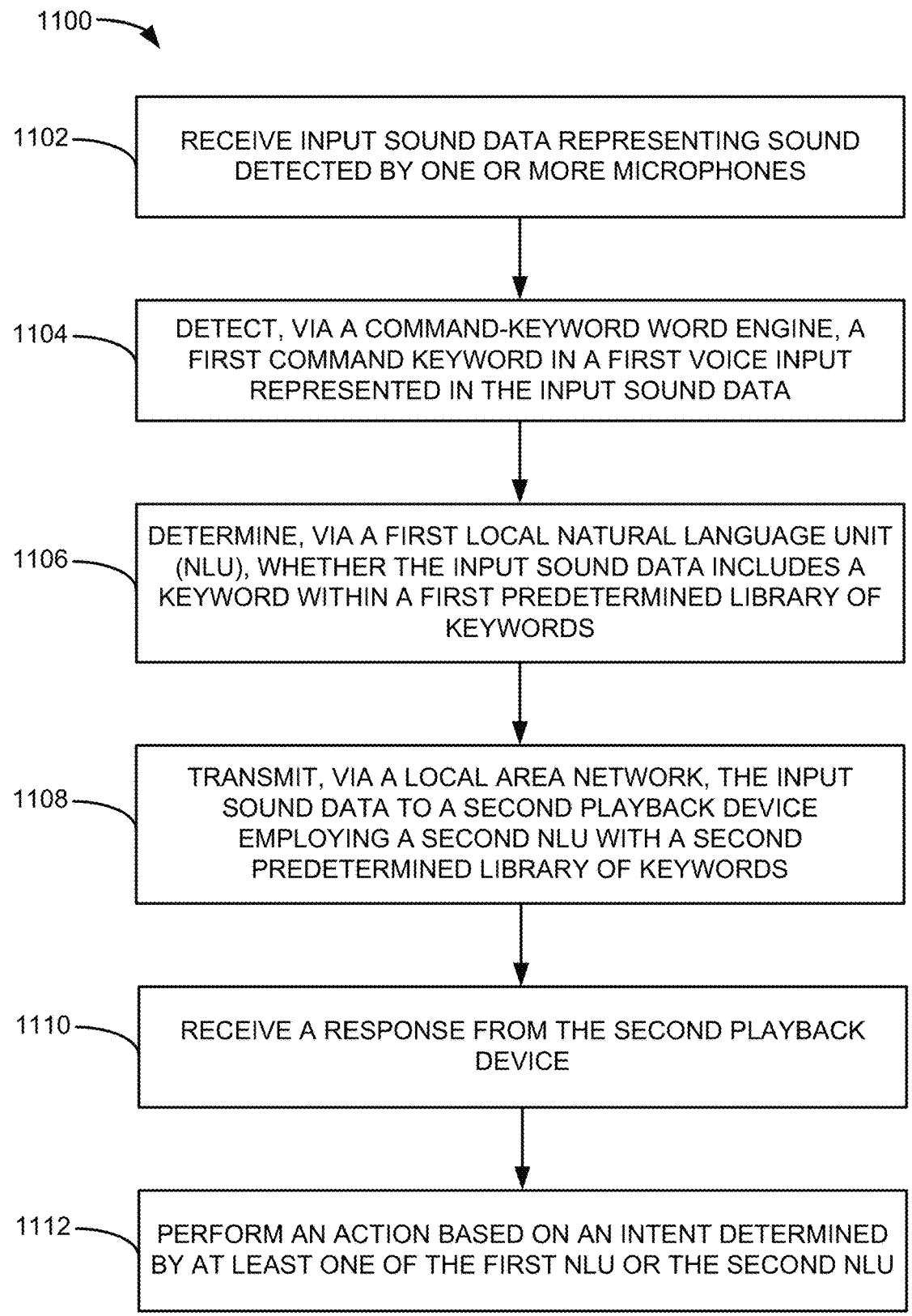
FIG. 11 is a flow diagram of an example method for locally distributed keyword detection in accordance with aspects of the disclosure.

To illustrate, FIG. 11 shows a table 1100 illustrating the respective contents of a first and second playlist determined based on similar voice inputs, but processed differently. In particular, the first playlist is determined by a VAS while the second playlist is determined by the NMD 703 (perhaps in conjunction with the media playback system control servers 906*a*). As shown, while both playlists purport to include a user's favorites, the two playlists include audio content from dissimilar artists and genres. In particular, the second playlist is configured according to usage of the playback device 102*f* in the Office 101*e* and also the user's interactions with multiple streaming audio services, while the first playlist is based on the multiple user's interactions with the VAS. As a result, the second playlist is more attuned to the types of music that the user prefers to listen to in the office 101*e* (e.g., indie rock and folk) while the first playlist is more representative of the interactions with the VAS as a whole.

A household may include multiple users. Two or more users may configure their own respective user profiles with the MPS 100. Each user profile may have its own user accounts of one or more streaming audio services associated with the respective user profile. Further, the media playback system control servers 906*a* may maintain or have access to data indicating each user's saved or preferred playlists, artists, albums, tracks, genres, and the like, which may be associated with the user profile of that user.

In various examples, names corresponding to user profiles may be populated in the library of the local NLU 779. This may facilitate referring to a particular user's saved or preferred playlists, artists, albums, tracks, or genres. For instance, when a voice input of "Play Anne's favorites on the patio" is processed by the local NLU 779, the local NLU 779 may determine that "Anne" matches a stored keyword corresponding to a particular user. Then, when performing the playback command corresponding to that voice input, the NMD 703 adds a playlist of that particular user's favorite audio tracks to the queue of the playback device 102*c* in the patio 101*i*. In some embodiments, different NMDs 703 of the MPS 100 have local NLUs 779 storing keywords associated with different user profiles. For example, a first NMD can have a first NLU 779 with keywords associated with a first user, Anne. Meanwhile, a second NMD can have a second NLU 779 storing keywords associated with a second user, Bryan.

In some cases, a voice input might not include a keyword corresponding to a particular user, but multiple user profiles are configured with the MPS 100. In some cases, the NMD 703 may determine the user profile to use in performing a command using voice recognition. Alternatively, the NMD 703 may default to a certain user profile. Further, the NMD 703 may use preferences from the multiple user profiles when performing a command corresponding to a voice input that did not identify a particular user profile. For instance, the NMD 703 may determine a favorites playlist including preferred or saved audio tracks from each user profile registered with the MPS 100.

The IOT cloud servers 906*c* may be configured to provide supporting cloud services to the smart devices 990. The smart devices 990 may include various "smart" internet-connected devices, such as lights, thermostats, cameras, security systems, appliances, and the like. For instance, an TOT cloud server 906*c* may provide a cloud service supporting a smart thermostat, which allows a user to control the smart thermostat over the internet via a smartphone app or website.

Accordingly, within examples, the TOT cloud servers 906*c* may maintain or have access to data associated with a user's smart devices 990, such as device names, settings, and configuration. Under appropriate conditions (e.g., after receiving user permission), the TOT cloud servers 906*c* may share this data with the media playback system control servers 906*a* and/or the NMD 703 via the links 903*c*. For instance, the TOT cloud servers 906*c* that provide the smart thermostat cloud service may provide data representing such keywords to the NMD 703, which facilitates populating the library of the local NLU 779 with keywords corresponding to the temperature.

Yet further, in some cases, the TOT cloud servers 906*c* may also provide keywords specific to control of their corresponding smart devices 990. For instance, the TOT cloud server 906*c* that provides the cloud service supporting the smart thermostat may provide a set of keywords corresponding to voice control of a thermostat, such as "temperature," "warmer," or "cooler," among other examples. Data representing such keywords may be sent to the NMDs 703 over the links 903 and the network 904 from the TOT cloud servers 906c.

As noted above, some households may include more than NMD 703. In example implementations, two or more NMDs 703 may synchronize or otherwise update the libraries of their respective local NLU 779. For instance, a first NMD 703 and a second NMD 703 may share data representing the libraries of their respective local NLU 779, possibly using a network (e.g., the network 904). Such sharing may facilitate the NMDs 703 being able to respond to voice input similarly, among other possible benefits. As noted elsewhere herein, in various embodiments the libraries of the respective local NLUs 779 of the NMD 703 can be identical or may vary from one to the next. In operation, voice input received at one NMD may be processed for keyword detection using local NLUs 779 of multiple different NMDs. This can advantageously expand the number of possible keywords to be identified in the voice input, as different NMDs can have NLUs 779 that support different libraries of keywords. For example, if a voice input contains a keyword that is not stored on the library of a first NLU 779 of a first NMD 703, the keyword may nonetheless be present in a library of a second NLU 779 of a second NMD 703. In some embodiments, this can also allow cross-checking of keyword detection to improve confidence and lower error rates.

In some instances, an NMD 703 that receives a voice input can selectively transmit the voice input to some but not all of the other NMDs 703 on the local network to perform keyword detection. For example, a first NMD 703 may identify the keyword "Spotify" in a voice input. Based on this keyword detection, the first NMD may transmit the voice input to a second NMD that is identified as having a library associated with Spotify commands (or media streaming service commands more generally). Similarly, if the first NMD 703 identifies the keyword "thermostat" in a voice input, the first NMD may transmit the voice input to a third NMD on the local network that is identified as having a library associated with IOT commands. Additionally or alternatively, a first NMD 703 may process voice input via its ASR and then, based on one or more keywords identified via the ASR, pass the ASR output to a second NMD for processing via its own NLU, which may include a different library of keywords associated with different intent categories. As one example, a first NMD 703 may identify the keyword "Spotify" in voice input via its onboard ASR. Based on this identified keyword, the output of the ASR (e.g., a text string representing the voice input) can be transmitted to a particular NMD having an NLU with a library of keywords associated with Spotify-specific commands. As a result, even if the identified keyword (in this example, "Spotify") is not sufficient to identify an associated intent, the identified keyword via the ASR is sufficient to direct the ASR output to an appropriate NLU for intent evaluation. In such a configuration, an environment may include multiple devices each having one or more ASRs and each having different NLUs with intent engines configured to identify intents based on the ASR output. For example, one device may have a local NLU configured to determine intents relating to music playback, while another device has an NLU configured to determine intents relating to home automation. In another example, one device could have an NLU with a rules-based intent engine, while a second device may have an NLU with a statistical intent engine, and a third device has a hybrid intent engine. Accordingly, an ASR output can be routed from one device to one or more different NLUs having different libraries and configured to identify different categories of intents.

In some embodiments, the ASR output can be evaluated in context to determine which device should receive the ASR output for intent processing. For example, the ASR output may have an associated confidence score associated with different text strings. In some instances, even if a particular text string has a low associated confidence, the context (i.e., the other words or phrases in the ASR output) may raise the overall confidence. For example, based on a user speaking the word "Spotify" in noisy conditions, the ASR output may provide a 40% confidence that the term "Spotify" is detected, and a 50% confidence that the term "notify" is detected. However, if the same ASR output also contains higher confidence in the terms "play" and "my favorites," then the ASR output may be modified to assign a higher confidence to the term "Spotify," since, in the context of "play my favorites," the overall likelihood of "Spotify" in the voice input is higher than "notify." In response, the ASR output may be transmitted to an NMD having a local NLU with a library of keywords associated with Spotify commands.

In some instances, the system can receive feedback regarding whether the analysis was correct (i.e., whether the user is satisfied with the identified intent). Over time, the distribution of NLUs may be organized such that the intent engines evolve over time towards higher performance. For example, over time, each NMD may apply small changes to its intent engine (e.g., changing supported keywords, changing statistical thresholds for identification of intent, changing internal rules for intent determination, etc.). Based on collected feedback, whichever device proves to be correct most often may then be copied into other devices. These devices may then again make small changes to their respective intent engines and the cycle repeats.

In some embodiments, the various NLUs distributed among a plurality of devices in the user environment can be configured such that each NLU performs a specific function or set of functions on ASR output (whether received from that particular NMD or from another local NMD). For example, one NLU may perform parsing, another may tag keywords, another may perform grammar analysis, etc.

In some embodiments, one or more of the components described above can operate in conjunction with the microphones 720 to detect and store a user's voice profile, which may be associated with a user account of the MPS 100. In some embodiments, voice profiles may be stored as and/or compared to variables stored in a set of command information or data table. The voice profile may include aspects of the tone or frequency of a user's voice and/or other unique aspects of the user, such as those described in previously referenced U.S. patent application Ser. No. 15/438,749.

In some embodiments, one or more of the components described above can operate in conjunction with the microphones 720 to determine the location of a user in the home environment and/or relative to a location of one or more of the NMDs 103. Techniques for determining the location or proximity of a user may include one or more techniques disclosed in previously referenced U.S. patent application Ser. No. 15/438,749, U.S. Pat. No. 9,084,058 filed Dec. 29, 2011, and titled "Sound Field Calibration Using Listener Localization," and U.S. Pat. No. 8,965,033 filed Aug. 31, 2012, and titled "Acoustic Optimization." Each of these applications is herein incorporated by reference in its entirety.

V. Example Locally Distributed Keyword Detection

As noted above, in media playback systems 100 having multiple NMDs 703, keyword detection can be improved by leveraging the presence of multiple NMDs 703 in a number of ways. In some embodiments, detection of keywords can be locally distributed among one or more NMDs 703 connected over a network (e.g., a local area network). For example, a first NMD 703 may receive a voice input and generate input sound data to be analyzed for detection of a command keyword as described previously. Concurrently or sequentially, the input sound data may be transmitted from the first NMD to a second NMD for evaluation and potential keyword detection.

In some embodiments, the first NMD can transmit input sound data (e.g., signal $S_{DS}$ as output from the VCC 760 of FIG. 7A) to the second NMD, which can then be evaluated via a command-keyword engine 771 of the second NMD, including evaluation using a local NLU 779 of the second NMD 703. In some embodiments, the first NMD can transmit the ASR output (e.g., signal $S_{ASR}$ of FIG. 7A), which can be evaluated by a local NLU 779 of the second NMD without first being evaluated for command-keyword detection.

The results of the keyword-detection processes performed by each of the NMDs 703 (e.g., the output of the respective command-keyword engine 771 of each NMD 703) can be compared to cross-check or confirm keyword detection. Such cross-checking can decrease error rates in keyword detection, for example by reducing the rate of false positives. Additionally or alternatively, different NMDs 703 can have different NLUs 779 with different libraries of keywords, and accordingly multiple NMDs 703 can be used to expand the total library of supported keywords in a user's environment. Accordingly, using multiple NMDs 703 to evaluate input sound data can improve local keyword detection by decreasing error rates and/or by expanding the number of supported keywords, thereby allowing keyword detection even in cases where a single NMD 703 may be unable to verify the presence of a keyword in the input sound data.

In some embodiments, processing the voice input via the NLU 779 is performed in response to detection of a command keyword via command-keyword engine 771a. Additionally or alternatively, voice input can be processed via the NLU 779 in response to detection of a wake-word event (e.g., detection of a VAS wake-word via the VAS wake-word engine 770a) or any other suitable trigger event. In such embodiments, following detection of a VAS wake word in voice input, the NLUs 779 of multiple NMDs can cooperate to provide an expanded library of keywords and/or to cross-check keyword detection results as described elsewhere herein.

FIG. 11 is a flow diagram showing an example method 1100 for locally distributed keyword detection. The keyword may be detected by leveraging the operation of two or more NMDs together. The method 1100 may be performed by a networked microphone device, such as the NMD 120 (FIG. 1A), which may include features of the NMD 703 (FIG. 7). In some implementations, the NMD is implemented within a playback device, as illustrated by the playback device 102r (FIG. 1G).

At block 1102, the method 1100 involves receiving input sound data representing sound detected by one or more microphones of an NMD 703 (which may be part of a playback device). For instance, the NMD 703 may detect sound via the microphones 720 (FIG. 7A). Further, the NMD 703 may process the detected sound using one or more components of the VCC 760 to produce input sound data for further processing.

At block 1104, the method 1100 involves detecting, via a command-keyword engine (e.g., command-keyword engine 771 of FIG. 7A), a first command keyword in a first voice input represented in the input sound data. To determine whether the voice input includes a command keyword, the command-keyword engine 771a may analyze the sound-data stream $S_{DS}$ (FIG. 7A). In particular, the ASR 772 may transcribe the sound-data stream $S_{DS}$ to text (e.g., the signal $S_{ASR}$) and the local NLU 779 may determine that words matching a keyword are in the transcribed text. In other examples, the command-keyword engine 771a may use one or more keyword identification algorithms on the sound-data stream $S_{DS}$. Other examples are possible as well.

At block 1106, the method 1100 includes determining, via a first NLU, whether the input sound data includes a keyword within a first predetermined library of keywords. For example, the local NLU 779 may detect that the input sound data at least one keyword (or any keywords) from the library of the local NLU 779. The local NLU 779 is configured to analyze the signal $S_{ASR}$ to spot (i.e., detect or identify) keywords in the voice input. The local NLU can also determine an intent based on the at least one keyword. For instance, the local NLU 779 may determine an intent from one or more keyword in the input sound data. As indicated above, the keywords in the library of the local NLU 779 can correspond to parameters. The keyword(s) in a voice input may indicate an intent, such as to play particular audio content in a particular zone.

At block 1108, the method 1200 involves transmitting, via a local area network, the input sound data to a second device. The second device can be, for example, a second NMD 703 having a second command-keyword engine 771 and a second NLU with a second predetermined library of keywords. In some embodiments, the second predetermined library of keywords of the second NMD can be substantially or completely identical to the first predetermined library of the first NMD. In some embodiments, some or all of the keywords present in the first predetermined library can vary from those present in the second predetermined library. The use of two (or more) different predetermined libraries introduces the possibility of dramatically increasing the total number of supported keywords. As one example, if each NMD has a library with approximately 10,000 keywords, then two NMDs having completely non-overlapping libraries may provide a combined 20,000 keywords for the media playback system of which the two NMDs are a part. In operation, voice input received at any one of the NMDs within the system can be processed for keyword detection among multiple NMDs. As such, a single voice input can be evaluated for detection of keywords supported by two or more of the NMDs, thereby significantly increasing the total library of keywords supported by the system.

In some embodiments, the different libraries can include dedicated directories. For example, the first predetermined library can include keywords that are associated with a first intent category (e.g., transport commands), while the predetermined library can include keywords that are associated with a second intent category (e.g., Internet-of-Things (IOT) commands or media service provider commands). By supporting different directories, a voice input received via the first NMD can be processed for detection of keywords associated with different intent categories, even if a single library on the first NMD would be unable to store or support the keywords associated with each of the different intent categories.

In some embodiments, the different libraries supported by the different NMDs can include partitions. For example, the first predetermined library can include a first partition of shared keywords and a second partition of dedicated keywords. The second predetermined library may then include a first partition of the shared keywords that is substantially or completely identical to the first partition of first predetermined library. The second predetermined library can also include a second partition of dedicated keywords that is substantially or completely distinct from the second partition of the first predetermined library. For example, the dedicated partition of the first predetermined library can store keywords associated with IOT commands, while the dedicated partition of the second predetermined library can store keywords associated with streaming media services commands. In some embodiments, the shared keywords can include keywords used most often (e.g., common transport commands such as "pause," "play," etc.). By storing the most commonly used commands in libraries of each NMD, the system may more consistently and responsively detect these keywords and perform associated operations. In some embodiments, there may be multiple partitions supported by each NMD, none of which is completely shared with other libraries.

At block 1110, a response from the second playback device is received at the first playback device. The response can include results of the second playback device evaluating the input sound data to identify keywords and/or an intent. In some embodiments, the response can include both any identified keyword(s) as well as associated confidence scores or other indicia relating to the likelihood of a matched keyword. If the libraries of the respective NLUs 779 of the respective first and second devices are different, it may be the case that the first NLU does not identify a keyword in the input sound data, while the second NLU of the second device does identify a keyword in the input sound data. Although these examples are described with respect to two NMDs, this process can be extended to any number of different NMDs, any or all of which can have different NLUs storing different libraries of keywords.

Finally, at block 1112, the device performs an action based on an intent determined by at least one of the first NLU or the second NLU. In one example, the first NLU of the first device does not identify a keyword match, while the response from the second NLU indicates an identified keyword (and, optionally, a sufficiently high confidence score). As a result, the first device may perform a command corresponding to the keyword identified via the second NLU. For instance, the NMD 703 may perform a playback command, which may involve generating one or more instructions to perform the command, which cause the target playback device(s) to perform the first playback command.

In some embodiments, instructing the target playback device(s) to perform the first playback command may be explicitly or implicitly defined. For example, the target playback devices may be explicitly defined by reference in the voice input 780 to the name(s) of one or more playback devices (e.g., by reference to a zone or zone group name). Alternatively, the voice input might not include any reference to the name(s) of one or more playback devices and instead may implicitly refer to playback device(s) 102 associated with the NMD 703. Playback devices 102 associated with the NMD 703 may include a playback device implementing the NMD 703, as illustrated by the playback device 102*d* implementing the NMD 103*d* (FIG. 1B)) or playback devices configured to be associated (e.g., where the playback devices 102 are in the same room or area as the NMD 703).

Within examples, performing an action may involve transmitting one or more instructions over one or more networks. For instance, the NMD 703 may transmit instructions locally over the network 903 to one or more playback devices 102 to perform instructions such as transport commands (FIG. 10), similar to the message exchange illustrated in FIG. 6. Further, the NMD 703 may transmit requests to the streaming audio service service(s) 906*b* to stream one or more audio tracks to the target playback device(s) 102 for playback over the links 903 (FIG. 10). Alternatively, the instructions may be provided internally (e.g., over a local bus or other interconnection system) to one or more software or hardware components (e.g., the electronics 112 of the playback device 102).

Figure 12:
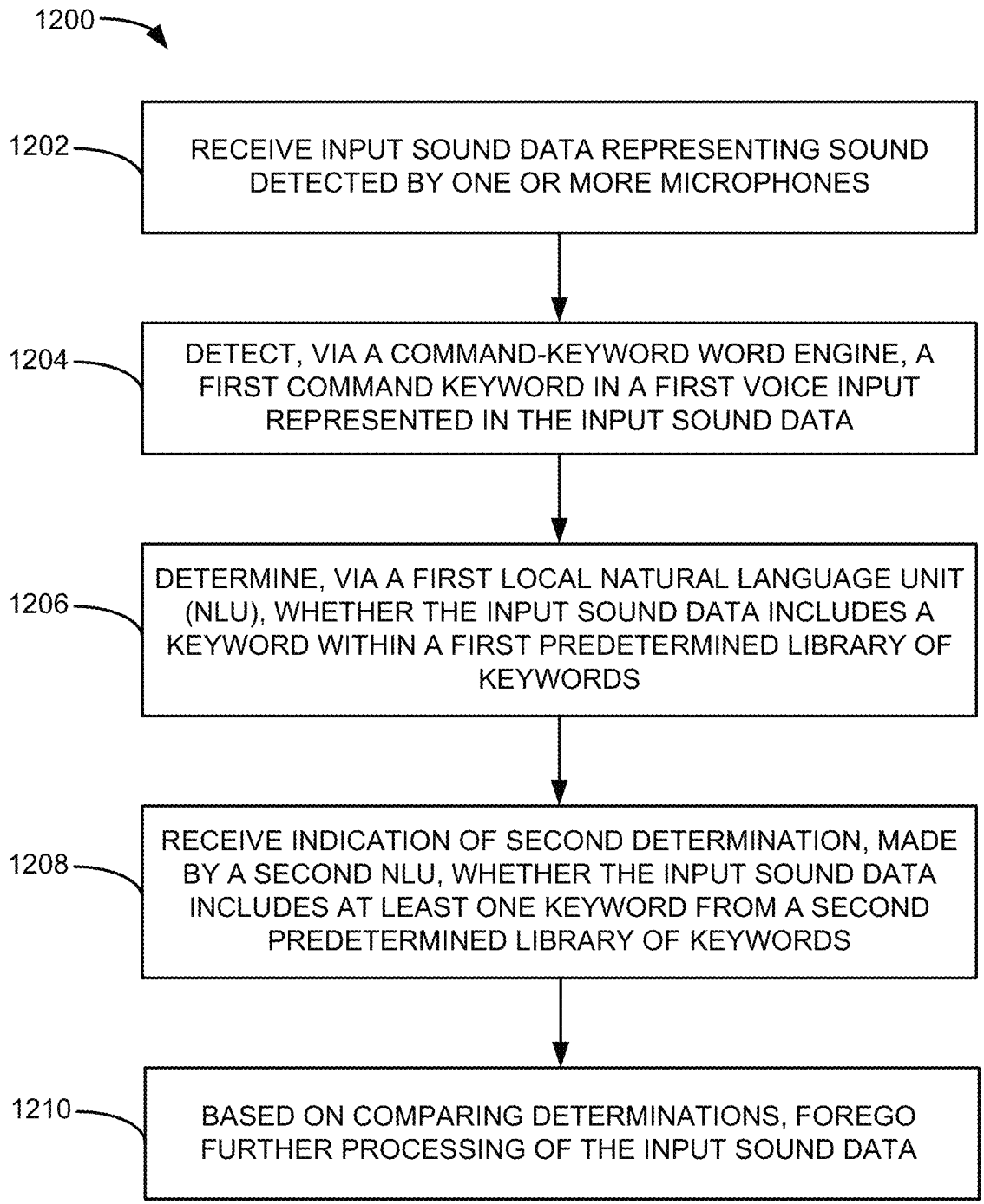
FIG. 12 is a flow diagram of another example method for locally distributed keyword detection in accordance with aspects of the disclosure.

FIG. 12 is a flow diagram showing another example method 1200 for locally distributed keyword detection. The method 1200 can facilitate cross-checking of keyword detection either among multiple NMDs or within different subsets of input sound data captured by microphones of a single NMD. As with the method 1100, the method 1200 may be performed by a networked microphone device, such as the NMD 103*s* (FIG. 1A), which may include features of the NMD 703 (FIG. 7A). In some implementations, the NMD is implemented within a playback device, as illustrated by the playback device 102*r* (FIG. 1G).

At block 1202, the method 1200 involves receiving input sound data representing sound detected by one or more microphones of an NMD. At block 1204, the method 1200 involves detecting, via a command-keyword engine (e.g., command-keyword engine 771 of FIG. 7A), a first command keyword in a first voice input represented in the input sound data. At block 1206, the method 1200 includes determining, via a first NLU, whether the input sound data includes a keyword within a first predetermined library of keywords. Blocks 1202, 1204, and 1206 can be carried out similar to blocks 1102, 1104, and 1106 described above with respect to the method 1100 of FIG. 11.

With continued reference to FIG. 12, at block 1208, the method 1200 involves receiving, at the first playback device, an indication that a second NLU has made a second determination that the input sound data includes at least one keyword within the predetermined library of keywords. In some embodiments, the second NLU can store a library of keywords that substantially or identically corresponds to the predetermined library of keywords stored by the first NLU. In other embodiments, the second NLU stores a library of keywords that partially but not completely overlaps with the library of keywords stored by the first NLU. In the case of overlapping or shared keywords that are present in libraries of both the first NLU and the second NLU, the second NLU can cross-check or confirm detection of such shared keywords by the first NLU. The response can include results of the second NLU evaluating the input sound data to identify keywords and/or an intent. In some embodiments, the response includes both any identified keyword(s) as well as associated confidence scores or other indicia relating to the likelihood of a matched keyword.

In some embodiments, the second NLU can be part of a second NMD having a second keyword engine. For example, the second NMD may separately detect the same user speech as voice input and process the voice input via the second NLU to determine whether a keyword is present. The results of this determination can then be transmitted over a local area network to the first device. In other embodiments, the first device may transmit, via a local area network, the input sound data to the second device for processing via its second NLU. The second device may then provide a response to the first device that includes a determination regarding whether a keyword was identified via the second NLU.

In some embodiments, the second NLU is not on a different device, but is on the same device and configured to evaluate different input sound data from the first NLU. For example, the NMD may have multiple microphones configured to generate sound data from a voice input. A first subset of the microphones may be used to generate first input sound data that can be evaluated to identify a keyword via the first NLU. A second subset of the microphones may be used to generate second input sound data from the same voice input that can be evaluated via the second NLU to identify a keyword. For example, the NMD 703 can be configured to generate a first sound-data stream $S_{DS}$ representing data obtained from a first subset of the microphones 720 (FIG. 7A), and to generate a second sound-data stream $S_{DS}$ representing data obtained from a second subset of the microphones 720 that is different from the first. Optionally, in some embodiments the subsets of the microphones can include some overlapping. Additionally, in some embodiments there may be three, four, five, or more different sound-data streams $S_{DS}$ generated using different subsets of microphones or other variations in processing of voice input. These different sound-data streams $S_{DS}$ can be separately evaluated for keyword detection. As a result, a single NMD may generate two determinations as outputs of keyword-detection engines: a first determination involving the first NLU analyzing the first input sound data, and a second determination involving the second NLU analyzing the second input sound data. In some embodiments the same NLU can be used to process each of the two (or more) different sound-data streams $S_{DS}$ for comparison.

At block 1210, the method involves comparing the first and second determinations and, based at least in part on the comparison, foregoing further processing. If, for example, the results do not match (e.g., the first NLU identifies the word "pause" but the second NLU does not identify any keyword), the NMD may decline to forego further processing of the input sound data. This reflects the assessment that detection of the word "pause" via the first NLU is likely a false positive, due to the lack of confirmation from the second NLU. If, in contrast, the determinations did match, the NMD may perform an action corresponding to the identified keyword. In this way, a second NLU is leveraged to cross-check the determination of the first NLU.

Figure 13:
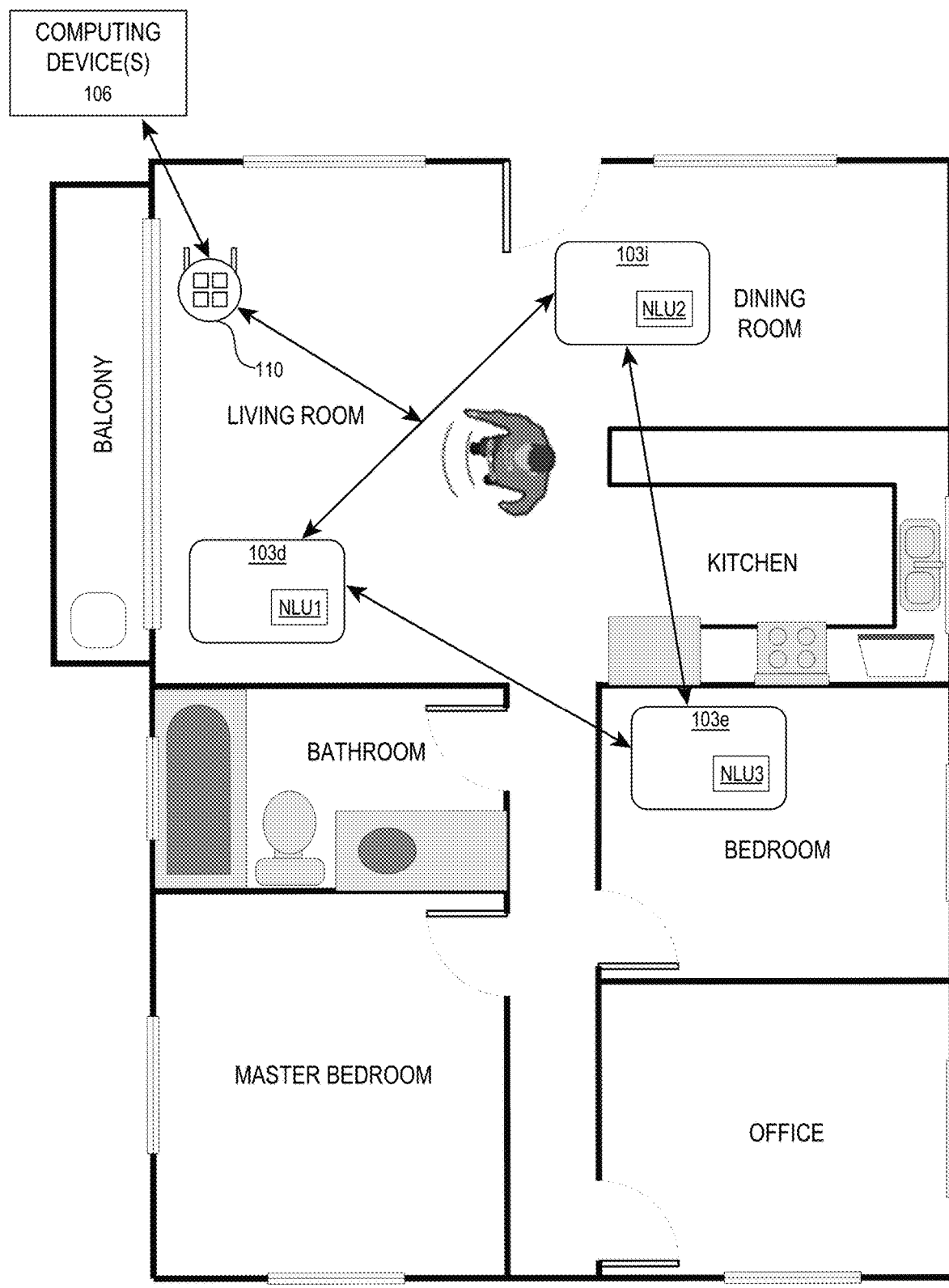
FIGS. 13-15 illustrate examples of locally distributed keyword detection via multiple network microphone devices in accordance with aspects of the disclosure.
Figure 14:
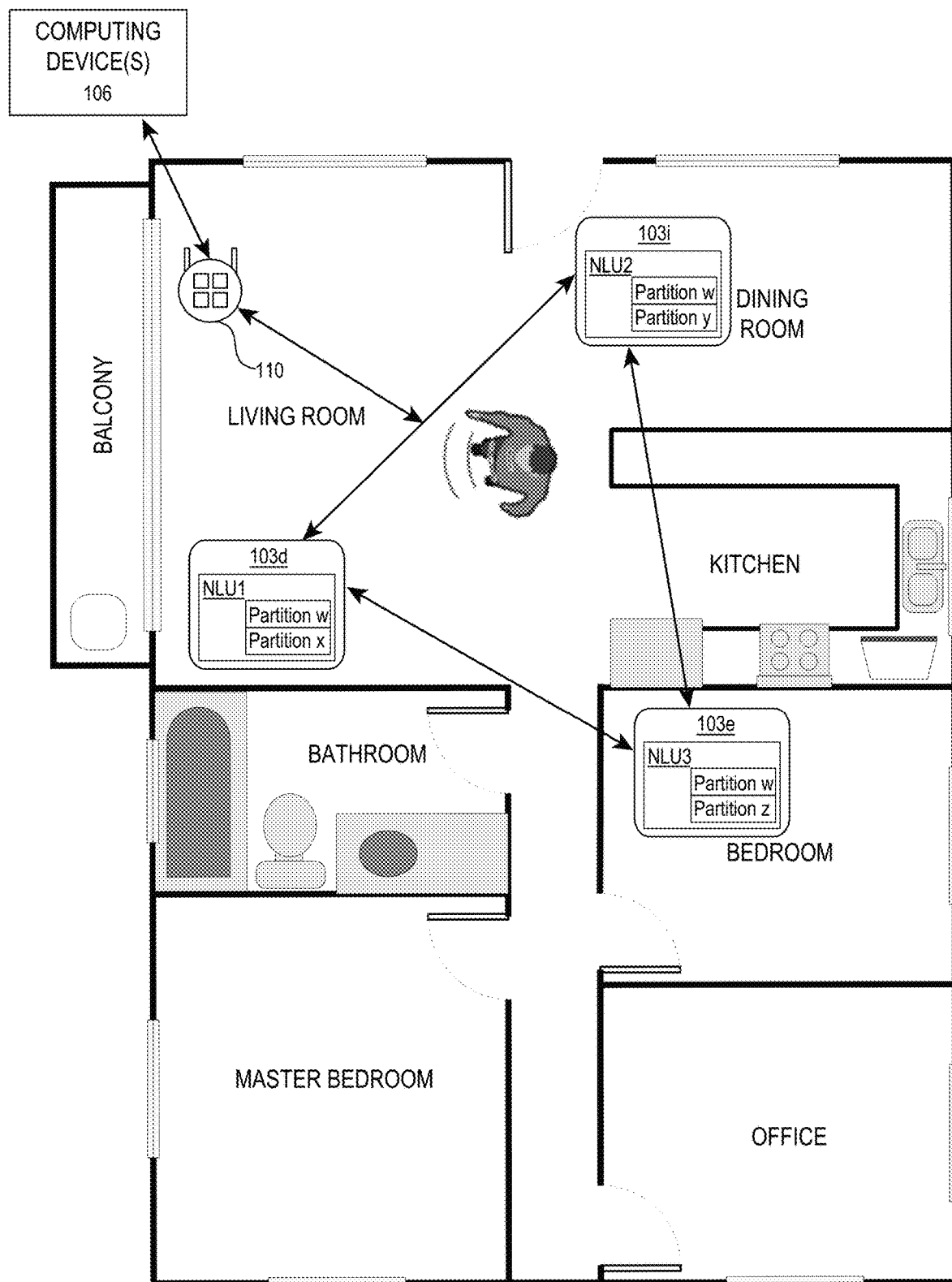
Figure 15:
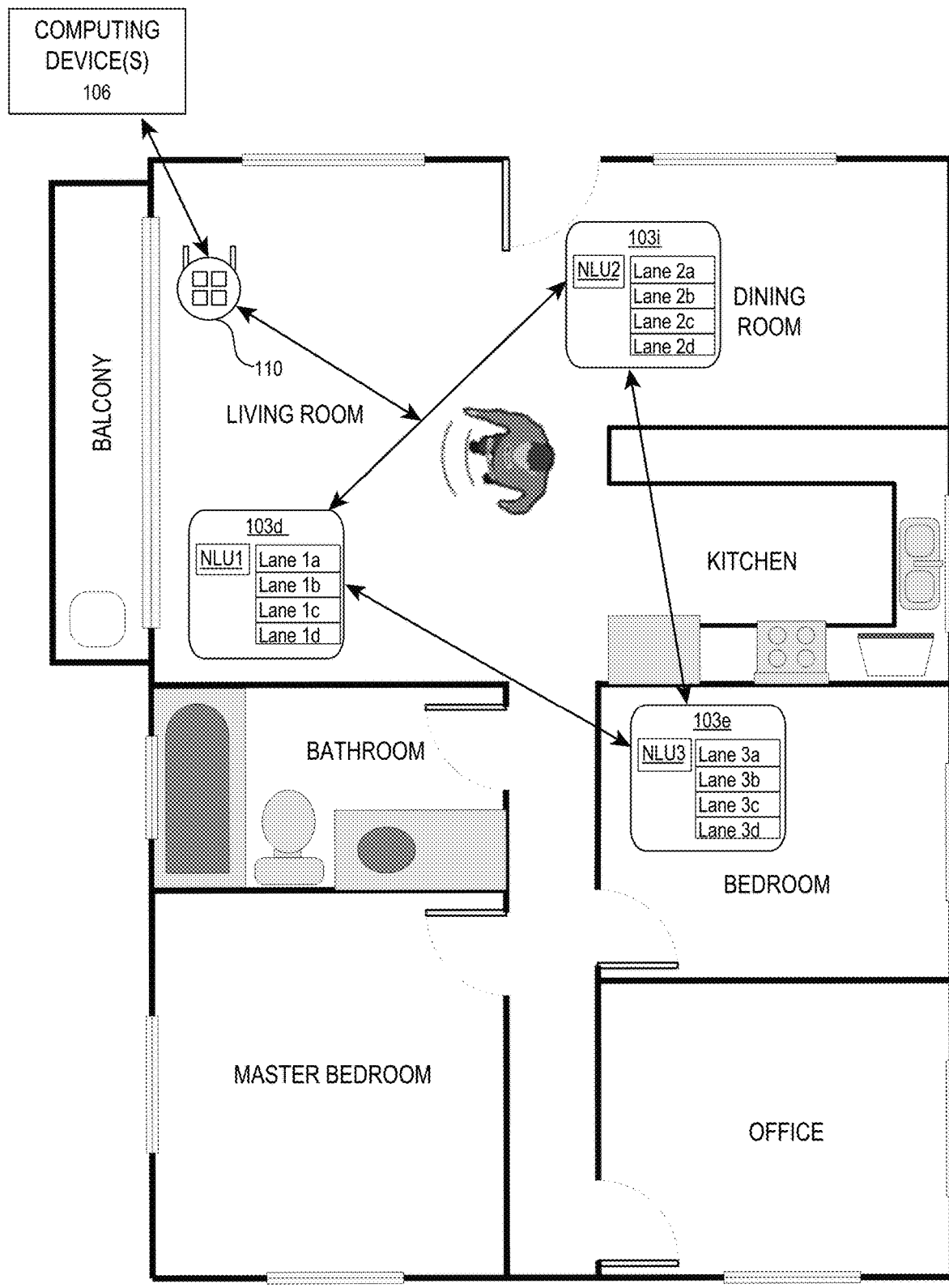

FIGS. 13-15 illustrate examples scenarios in which one or more NMDs having local NLUs communicate and perform actions in accordance with aspects of the disclosure. The environment includes a first NMD 103d having a first NLU ("NLU1"), a second NMD 103i having a second NLU ("NLU2"), and a third NMD 103e having a third NLU ("NLU3"). Each of the NMDs are in communication with one another over a local area network facilitated by the router 110. The NMDs may also be in communication with one or more remote computing devices 106 over a wide area network via the router 110. Each of the NMDs may include features of the NMD 703 (FIG. 7A). In some implementations, the NMDs may be implemented within a playback device, as illustrated by the playback device 102r (FIG. 1G). Although these examples are shown with three NMDs, these processes can be applied to fewer (e.g., two) or greater (e.g., three, four, or more) numbers of NMDs within the environment.

As described in more detail below, in various embodiments each of NLU1, NLU2, and NLU3 may store predetermined libraries of keywords that are substantially or completely identical, partially overlapping, or completely non-overlapping. In example implementations, the individual NMDs 103d, 103i, and 103e may synchronize or otherwise update the libraries of their respective local NLUs. For instance, the NMDs 103d, 103i, and 103e may share data representing the libraries of their respective local NLUs NLU1, NLU2, and NLU3, possibly using a network.

FIGS. 13 and 14 illustrate examples in which multiple NMDs are leveraged to provide an increased number of keywords supported by the combined NLUs within the environment. As noted previously, any one NLU may support a relatively limited number of keywords (e.g., having a library of approximately 10,000 predetermined keywords). Accordingly, it can be advantageous to store different keywords or combinations of keywords in the libraries of different NLUs associated with different NMDs within the environment.

With respect to FIG. 13, the NLU1 may store a first predetermined library of keywords, NLU2 stores a second predetermined library of keywords, and NLU3 stores a third predetermined library of keywords. In this example, each of the libraries of keywords can be substantially or completely non-overlapping. As a result, if each library supports approximately 10,000 keywords, then the combined libraries support approximately 30,000 keywords, thereby dramatically increasing the number of keywords available for local keyword detection.

As an example, the user speaks a command to the first NMD 103d to "Play Hey Jude by the Beatles". The first NMD 103d detects the user speech as voice input which is processed using a command-keyword engine as described previously herein. This processing includes searching a predetermined library of keywords stored by NLU1. In this example, NLU1 finds a match for the "play" command but does not find a match for "Hey Jude." In parallel with this processing via NLU1 (or subsequent to the determination of no match via NLU1), the first NMD 103d transmits a request to the second NMD 103i and third NMD 103e to perform keyword detection on the voice input via NLU2 and NLU3. Each of these NMDs may process the voice input from the first NMD 103d to detect a match with keywords stored in their respective libraries. If, for example, the second NMD 103i detects a match with "Hey Jude," the second NMD 103i can provide a response to the first NMD 103d that include instructions to stream the song "Hey Jude" from Apple Music or other cloud-based music service. Notably, this request for streaming content from a cloud-based provider can be performed without requiring the intervention of a VAS. If, in contrast, neither the second NMD 103i nor the third NMD 103e identifies a matching keyword, then the first NMD 103d may either (a) provide a response to the user that the command cannot be processed (e.g., a voice output stating "I'm sorry, I couldn't understand that request") and/or (b) transmits the voice input to a VAS (e.g., VAS 190 of FIG. 1B) for remote processing.

In this example, it can be seen that locally distributing keywords among different libraries stored by different NMDs can increase the total number of supported keywords for local processing without recourse to a remote VAS. Local processing may provide an improved user experience, as it eliminates the latency associated with transmission of requests to a remote VAS for processing.

FIG. 14 illustrates another example environment in which keywords are distributed among the three NMDs having respective NLUs. In this example, however, each NLU has two associated partitions. As illustrated, each of the NLUs includes a shared partition w, while NLU1 also includes a dedicated partition x, NLU2 includes a dedicated partition y, and NLU3 includes a dedicated partition z. Although this example illustrates each NLU having the same shared partition and one dedicated partition, in various embodiments any number of partitions may be shared only among some of the NLUs within the environment, and additionally any number of dedicated partitions may be stored by one or more of the NLUs. In some embodiments, the shared partition x can include keywords associated with the most frequently used commands, while the dedicated partition x, y, and z can each store keywords associated with less frequently commands. Such a configuration may reduce access time or latency by requiring searching across the network to other NLUs only when the local NLU of the NMD that receives the voice input is not found to contain the keyword. In the cases of most commonly used phrases (e.g., "pause" or other transport commands), each NLU is equipped with corresponding keywords and accordingly the NMD can respond to the user's voice input without requiring the cooperation of other NMDs on the network.

In some embodiments, the dedicated partitions associated with different NLUs can correspond to different intent categories. For example, partition x can store keywords associated with IOT commands, partition y can store keywords associated with media service provider commands, and partition z can store keywords associated with user alarms and timers. In some embodiments, voice input received at one NMD can be selectively routed to another NMD for processing via its NLU based on the associated dedicated partition of that NLU. For example, if the first NMD 103d identifies the keyword "doorbell" in a voice input, the first NMD may transmit the voice input to the third NMD 103e, whose dedicated partition z contains keyword associated with IOT commands.

FIGS. 13 and 15 illustrate examples in which multiple NMDs can be leveraged to cross-check or confirm keyword determinations made by individual NMDs. For example, two or more NMDs may detect at least one keyword in voice input. By comparing determinations among the NMDs, the associated confidence of keyword detection can be increased, and the error rate thereby reduced. In these examples, the NLUs of the individual NMDs may have at least partially overlapping libraries of keywords, or in some examples can have completely identical libraries of keywords.

With reference back to FIG. 13, a user's voice input can be separately processed by two or more NMDs for keyword detection and the results can be compared or otherwise combined to make a final determination. For example, the user may provide a voice input detected by both the first NMD 103d and the second NMD 103i. Each of these NMDs may process the voice input (e.g., using their respective NLUs NLU1 and NLU2) to identify one or more keywords in the voice input. If the results match (either exactly or generally), then one of the NMDs may proceed to process the command. If the results of the two determinations do not match, then the NMDs may disregard the command or perform some other intervention, such as prompting the user to restate her request. For example, if the first NMD 103d detects that the user spoke "play songs by train" and the second NMD 103i detects that the user spoke "play blame it on the rain," the system may disregard the command or perform some other intervention. As noted above, in some embodiments the respective NLUs can include only partially overlapping libraries (e.g., each having a shared partition w, while having other non-shared, dedicated partitions as in FIG. 14). In such embodiments, the system can be configured to perform such cross-checking only on keywords that are found in the overlapping or shared keywords of the libraries.

With reference to FIG. 15, in some instances cross-checking can be performed not only between individual NMDs, but between different subsets of the input sound data as detected by an individual NMD. As illustrated, the first NMD 103d includes a first NLU1 and four lanes Lane 1a-1d. Similarly, the second NMD 103i includes the second NLU2 and four lanes 2a-2d, and the third NMD 103e includes the second NLU3 and four lanes 3a-3d. As used herein, a "lane" can refer to input sound data generated from a single microphone or from any combination of microphones of the NMD. For example, one or more individual microphones of the first NMD 103d can be used to generate input sound data corresponding to a first lane 1a, while a different subset of microphones is used to generate input sound data corresponding to a second lane 1b, etc. Note that in some instances these subsets can at least partially overlap, such that sound data captured by a single microphone may be used to generate data for more than one lane. In operation, the input sound data can differ from one lane to the next, and accordingly the NLU1 may return different results (e.g., identify different keywords, or fail to identify any keyword at all) when analyzing the input sound data of the different lanes. These different instances of input sound data can allow a single NMD to cross-check any keyword determination by confirming that the NLU identifies the same keyword across some or all of the lanes.

In some embodiments, a single NMD may include multiple different NLUs, each of which is configured to analyze the output of some but not all of the lanes. For example, the first NMD 103d could have four NLUs, each of which is configured to analyze the input sound data of one of the lanes 1a-1d. These NLUs could have only partially overlapping libraries of keywords, such that together the total number of stored keywords is expanded, while still permitting cross-checking for determination of keywords that are shared across two or more NLUs. In some embodiments, such cross-checking can be performed across NMDs. For example, a detection of a keyword using any one lanes 1a-d of the first NMD 103d can be compared with detection of a keyword using any one of lanes 2a-2d of the second NMD 103i. The lanes and NMDs can be combined in any number of ways to detect keywords and to compare results to increase confidence in keyword detection.

Accordingly, there are numerous advantages to distributing keyword detection among multiple different devices over a local network. The various aspects of locally distributed keyword detection described in the different examples above can be combined, modified, re-ordered, or otherwise altered to achieve the desired implementation.

CONCLUSION

The description above discloses, among other things, various example systems, methods, apparatus, and articles of manufacture including, among other components, firmware and/or software executed on hardware. It is understood that such examples are merely illustrative and should not be considered as limiting. For example, it is contemplated that any or all of the firmware, hardware, and/or software aspects or components can be embodied exclusively in hardware, exclusively in software, exclusively in firmware, or in any combination of hardware, software, and/or firmware. Accordingly, the examples provided are not the only way(s) to implement such systems, methods, apparatus, and/or articles of manufacture.

The specification is presented largely in terms of illustrative environments, systems, procedures, steps, logic blocks, processing, and other symbolic representations that directly or indirectly resemble the operations of data processing devices coupled to networks. These process descriptions and representations are typically used by those skilled in the art to most effectively convey the substance of their work to others skilled in the art. Numerous specific details are set forth to provide a thorough understanding of the present disclosure. However, it is understood to those skilled in the art that certain embodiments of the present disclosure can be practiced without certain, specific details. In other instances, well known methods, procedures, components, and circuitry have not been described in detail to avoid unnecessarily obscuring aspects of the embodiments. Accordingly, the scope of the present disclosure is defined by the appended claims rather than the forgoing description of embodiments.

When any of the appended claims are read to cover a purely software and/or firmware implementation, at least one of the elements in at least one example is hereby expressly defined to include a tangible, non-transitory medium such as a memory, DVD, CD, Blu-ray, and so on, storing the software and/or firmware.

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples may be combined in any combination, and placed into a respective independent example. The other examples can be presented in a similar manner.

Example 1: A playback device of a media playback system, the playback device comprising: at least one speaker; one or more microphones configured to detect sound; a network interface; one or more processors; and data storage having instructions stored thereon that are executable by the one or more processors to cause the playback device to perform functions comprising: receiving input sound data representing the sound detected by the one or more microphones; detecting, via a command-keyword engine, a first command keyword in a first voice input represented in the input sound data, wherein the command-keyword engine is configured to (a) process input sound data representing the sound detected by the at least one microphone and (b) generate a command-keyword event when the command-keyword engine detects, in the input sound data, at least one of a plurality of keywords supported by the command-keyword engine; in response to detecting the first command keyword, making a first determination, via a first local natural language unit (NLU), whether the input sound data includes at least one keyword within a first a first predetermined library of keywords from which the first NLU is configured to determine an intent of a given voice input; receiving an indication of a second determination, made by a second NLU, whether the input sound data includes at least one keyword from a second predetermined library of keywords; comparing the results of the first determination with the second determination; and based on the comparison, foregoing further processing of the input sound data.

Example 2: The playback device of claim 1, wherein the functions further comprise: detecting, via the command-keyword engine, a second command keyword in a second voice input represented in second input sound data; in response to detecting the second command keyword, making a third determination, via the first local NLU, that the second input sound data includes one or more keywords from the first predetermined library of keywords; receiving an indication of a fourth determination made by the second NLU that the second input sound data includes one or more keywords from the second predetermined library of keywords; comparing the results of the third determination with the fourth determination; and based on the comparison, performing a command according to one or more parameters corresponding to the at least one keyword in the second input sound data.

Example 3: The playback device of Example 2, wherein comparing the results of the third determination with the fourth determination comprises confirming one or more keywords of the third determination are identical to the one or more keywords of the fourth determination.

Example 4: The playback device of any one of the preceding Examples, wherein receiving an indication of a second determination made by the second NLU comprises receiving, over a local area network via the network interface, the indication from a second playback device having the second NLU.

Example 5: The playback device of any one of the preceding Examples, wherein: the playback device comprises a plurality of microphones; the first NLU is configured to detect, in input sound data detected by a first subset of the microphones, keywords from the first predetermined library of keywords; and the second NLU is configured to detect, in input sound data detected by a second subset of the microphones, keywords from the second predetermined library of keywords.

Example 6: The playback device of any one of the preceding Examples, wherein the first predetermined library of keywords includes one or more keywords that are not included in the second predetermined library of keywords.

Example 7: The playback device of any one of the preceding Examples, further comprising a voice assistant service (VAS) wake-word engine configured to receive input sound data representing the sound detected by the at least one microphone and generate a VAS wake-word event when the VAS wake-word engine detects a VAS wake word in the input sound data, wherein the playback device streams sound data representing the sound detected by the at least one microphone to one or more servers of the VAS when the VAS wake-word event is generated.

Example 8: A method comprising: receiving input sound data representing the sound detected by one or more microphones of a playback device; detecting, via a command-keyword engine, a first command keyword in a first voice input represented in the input sound data, wherein the command-keyword engine is configured to (a) process input sound data representing the sound detected by the at least one microphone and (b) generate a command-keyword event when the command-keyword engine detects, in the input sound data, at least one of a plurality of keywords supported by the command-keyword engine; in response to detecting the first command keyword, making a first determination, via a first local natural language unit (NLU), whether the input sound data includes at least one keyword within a first a first predetermined library of keywords from which the first NLU is configured to determine an intent of a given voice input; receiving an indication of a second determination, made by a second NLU, whether the input sound data includes at least one keyword from a second predetermined library of keywords; comparing the results of the first determination with the second determination; and based on the comparison, foregoing further processing of the input sound data.

Example 9: The method of any one of the preceding Examples, further comprising: detecting, via the command-keyword engine, a second command keyword in a second voice input represented in second input sound data; in response to detecting the second command keyword, making a third determination, via the first local NLU, that the second input sound data includes one or more keywords from the first predetermined library of keywords; receiving an indication of a fourth determination made by the second NLU that the second input sound data includes one or more keywords from the second predetermined library of keywords; comparing the results of the third determination with the fourth determination; and based on the comparison, performing a command according to one or more parameters corresponding to the at least one keyword in the second input sound data.

Example 10: The method of any one of the preceding Examples, wherein comparing the results of the third determination with the fourth determination comprises confirming one or more keywords of the third determination are identical to the one or more keywords of the fourth determination.

Example 11: The method of any one of the preceding Examples, wherein receiving an indication of the second determination made by the second NLU comprises receiving, over a local area network via the network interface, the indication from a second playback device having the second NLU.

Example 12: The method of any one of the preceding Examples, wherein: the playback device comprises a plurality of microphones; the first NLU detects, in input sound data detected by a first subset of the microphones, keywords from the first predetermined library of keywords; and the second NLU detects, in input sound data detected by a second subset of the microphones, keywords from the second predetermined library of keywords.

Example 13: The method of any one of the preceding Examples, wherein the first predetermined library of keywords includes one or more keywords that are not included in the second predetermined library of keywords.

Example 14: The method of any one of the preceding Examples, wherein the playback device further comprises a voice assistant service (VAS) wake-word engine configured to receive input sound data representing the sound detected by the at least one microphone and generate a VAS wake-word event when the VAS wake-word engine detects a VAS wake word in the input sound data, wherein the functions further comprise streaming sound data representing the sound detected by the at least one microphone to one or more servers of the VAS when the VAS wake-word event is generated.

Example 15: A tangible, non-transitory computer-readable medium storing instructions that, when executed by one or more processors, cause the processors to perform functions comprising: the method of any one of the preceding Examples.

Example 16: A playback device of a media playback system, the playback device comprising: at least one speaker; one or more microphones configured to detect sound; a network interface; one or more processors; and data storage having instructions stored thereon that are executable by the one or more processors to cause the playback device to perform functions comprising: receiving input sound data representing the sound detected by the one or more microphones; detecting, via a command-keyword engine, a first command keyword in a first voice input represented in the input sound data, wherein the command-keyword engine is configured to (a) process input sound data representing the sound detected by the at least one microphone and (b) generate a command-keyword event when the command-keyword engine detects, in the input sound data, one of a plurality of keywords supported by the command-keyword engine; in response to detecting the first command keyword, determining, via a first local natural language unit (NLU), whether the input sound data includes at least one keyword within a first predetermined library of keywords from which the first NLU is configured to determine an intent of a given voice input; transmitting, via the network interface over a local area network, the input sound data to a second playback device of the media playback system, the second playback device employing a second local NLU with a second predetermined library of keywords from which the second NLU is configured to determine an intent of a given voice input; receiving, via the network interface, a response from the second playback device; and after receiving the response from the second playback device, performing an action based on an intent determined by at least one of the first NLU or the second NLU according to the one or more particular keywords in the voice input.

Example 17: The playback device of any one of the preceding Examples, wherein the first predetermined library of keywords includes keywords that are not included within the second predetermined library of keywords.

Example 18: The playback device of any one of the preceding Examples, wherein: the first predetermined library of keywords comprises a first partition having a first subset of keywords and a second partition having a second subset of keywords different from the first subset of keywords; the second predetermined library of keywords comprises a third partition having a third subset of keywords and a fourth partition having a fourth subset of keywords; wherein the first subset of keywords and the third subset of keywords include some or all of the same keywords; wherein the third subset of keywords differs from the first, second, and fourth subsets of keywords, and wherein the fourth subset of keywords differs from the first, second, and third subsets of keywords.

Example 19: The playback device of any one of the preceding Examples, wherein the first subset of keywords and the third subset of keywords are identical, and include a plurality of keywords associated with playback transport commands.

Example 20: The playback device of any one of the preceding Examples, wherein the transmitting the input sound data via the network interface to a second playback device of the media playback system comprises selecting the second playback device from among a plurality of additional playback devices of the media playback system, wherein each of the additional playback devices comprises a respective NLU configured to detect, in input sound data, keywords from a respective predetermined library of keywords different from the other respective predetermined libraries of keywords from which each respective NLU is configured to determine an intent of a given voice input, wherein the selection is based at least in part on the input sound data.

Example 21: The playback device of any one of the preceding Examples, wherein the keywords of the first predetermined library of keywords associated with the first NLU comprises keywords corresponding to a first intent category, and wherein the second predetermined library of keywords associated with the second NLU comprises keywords corresponding to a second intent category.

Example 22: The playback device of any one of the preceding Examples, further comprising a voice assistant service (VAS) wake-word engine configured to receive input sound data representing the sound detected by the at least one microphone and generate a VAS wake-word event when the first wake-word engine detects a VAS wake word in the input sound data, wherein the playback device streams sound data representing the sound detected by the at least one microphone to one or more servers of the voice assistant service when the VAS wake-word event is generated.

Example 23: A method comprising: receiving input sound data representing the sound detected by one or more microphones of a playback device; detecting, via a command-keyword engine, a first command keyword in a first voice input represented in the input sound data, wherein the command-keyword engine is configured to (a) process input sound data representing the sound detected by the at least one microphone and (b) generate a command-keyword event when the command-keyword engine detects, in the input sound data, one of a plurality of keywords supported by the command-keyword engine; in response to detecting the first command keyword, determining, via a first local natural language unit (NLU), whether the input sound data includes at least one keyword within a first predetermined library of keywords from which the first NLU is configured to determine an intent of a given voice input; transmitting, via the network interface over a local area network, the input sound data to a second playback device of the media playback system, the second playback device employing a second local NLU with a second predetermined library of keywords from which the second NLU is configured to determine an intent of a given voice input; receiving, via the network interface, a response from the second playback device; and after receiving the response from the second playback device, performing an action based on an intent determined by at least one of the first NLU or the second NLU according to the one or more particular keywords in the voice input.

Example 24: The method of any one of the preceding Examples, wherein the first predetermined library of keywords includes keywords that are not included within the second predetermined library of keywords.

Example 25: The method of any one of the preceding Examples, wherein: the first predetermined library of keywords comprises a first partition having a first subset of keywords and a second partition having a second subset of keywords different from the first subset of keywords; the second predetermined library of keywords comprises a third partition having a third subset of keywords and a fourth partition having a fourth subset of keywords; wherein the first subset of keywords and the third subset of keywords include some or all of the same keywords; wherein the third subset of keywords differs from the first, second, and fourth subsets of keywords, and wherein the fourth subset of keywords differs from the first, second, and third subsets of keywords.

Example 26: The method of any one of the preceding Examples, wherein the first subset of keywords and the third subset of keywords are identical, and include a plurality of keywords associated with playback transport commands.

Example 27: The method of any one of the preceding Examples, wherein the transmitting the input sound data via the network interface to a second playback device of the media playback system comprises selecting the second playback device from among a plurality of additional playback devices of the media playback system, wherein each of the additional playback devices comprises a respective NLU configured to detect, in input sound data, keywords from a respective predetermined library of keywords different from the other respective predetermined libraries of keywords from which each respective NLU is configured to determine an intent of a given voice input, wherein the selection is based at least in part on the input sound data.

Example 28: The method of any one of the preceding Examples, wherein the keywords of the first predetermined library of keywords associated with the first NLU comprises keywords corresponding to a first intent category, and wherein the second predetermined library of keywords associated with the second NLU comprises keywords corresponding to a second intent category.

Example 29: The method of any one of the preceding Examples, wherein the playback device further comprises a voice assistant service (VAS) wake-word engine configured to receive input sound data representing the sound detected by the at least one microphone and generate a VAS wake-word event when the first wake-word engine detects a VAS wake word in the input sound data, wherein the functions further comprise streaming sound data representing the sound detected by the at least one microphone to one or more servers of the voice assistant service when the VAS wake-word event is generated.

Example 30: A tangible, non-transitory computer-readable medium storing instructions that, when executed by one or more processors, cause the processors to perform functions comprising: the method of any one of the preceding Examples.

The invention claimed is:

1. A playback device of a media playback system, the playback device comprising:
   at least one speaker;
   one or more microphones configured to detect sound;
   a network interface;
   one or more processors; and
   data storage having instructions stored thereon that are executable by the one or more processors to cause the playback device to perform functions comprising:
      receiving input sound data representing the sound detected by the one or more microphones;
      detecting, via a command-keyword engine, a first command keyword in a first voice input represented in the input sound data, wherein the command-keyword engine is configured to (a) process input sound data representing the sound detected by at least one microphone and (b) generate a command-keyword event when the command-keyword engine detects, in the input sound data, one of a plurality of keywords supported by the command-keyword engine;
      in response to detecting the first command keyword, determining, via a first local natural language unit (NLU), whether the input sound data includes at least one keyword within a first predetermined library of keywords from which the first local NLU is configured to determine an intent of a given voice input, the first predetermined library of keywords comprising a first partition having a first subset of keywords and a second partition having a second subset of keywords;

transmitting, via the network interface over a local area network, the input sound data to a second playback device of the media playback system, the second playback device employing a second local NLU with a second predetermined library of keywords from which the second local NLU is configured to determine an intent of a given voice input, the second predetermined library comprising a third partition having a third subset of keywords and a fourth partition having a fourth subset of keywords;

receiving, via the network interface, a response from the second playback device; and after receiving the response from the second playback device, performing an action based on an intent determined by at least one of the first local NLU or the second local NLU according to the one or more particular keywords in the first voice input, wherein the first subset of keywords and the third subset of keywords include some or all of the same keywords, wherein the second subset of keywords differs from the first, third, and fourth subsets of keywords, and wherein the fourth subset of keywords differs from the first, second, and third subsets of keywords.

2. The playback device of claim 1, wherein the first predetermined library of keywords includes keywords that are not included within the second predetermined library of keywords.

3. The playback device of claim 1, wherein the first subset of keywords and the third subset of keywords are identical, and include a plurality of keywords associated with playback transport commands.

4. The playback device of claim 1, wherein the transmitting the input sound data via the network interface to a second playback device of the media playback system comprises selecting the second playback device from among a plurality of additional playback devices of the media playback system, wherein each of the plurality of additional playback devices comprises a respective NLU configured to detect, in input sound data, keywords from a respective predetermined library of keywords different from other respective predetermined libraries of keywords from which each respective NLU is configured to determine an intent of a given voice input, wherein the selection is based at least in part on the input sound data.

5. The playback device of claim 1, wherein the keywords of the first predetermined library of keywords associated with the first local NLU comprises keywords corresponding to a first intent category, and wherein the second predetermined library of keywords associated with the second local NLU comprises keywords corresponding to a second intent category.

6. The playback device of claim 1, further comprising a voice assistant service (VAS) wake-word engine configured to receive input sound data representing the sound detected by the at least one microphone and generate a VAS wake-word event when the first wake-word engine detects a VAS wake word in the input sound data, wherein the playback device streams sound data representing the sound detected by the at least one microphone to one or more servers of the voice assistant service when the VAS wake-word event is generated.

7. A method comprising:

receiving input sound data representing a sound detected by one or more microphones of a playback device;

detecting, via a command-keyword engine, a first command keyword in a first voice input represented in the input sound data, wherein the command-keyword engine is configured to (a) process input sound data representing the sound detected by at least one microphone and (b) generate a command-keyword event when the command-keyword engine detects, in the input sound data, one of a plurality of keywords supported by the command-keyword engine;

in response to detecting the first command keyword, determining, via a first local natural language unit (NLU), whether the input sound data includes at least one keyword within a first predetermined library of keywords from which the first local NLU is configured to determine an intent of a given voice input, the first predetermined library of keywords comprising a first partition having a first subset of keywords and a second partition having a second subset of keywords;

transmitting, via a network interface over a local area network, the input sound data to a second playback device of a media playback system, the second playback device employing a second local NLU with a second predetermined library of keywords from which the second local NLU is configured to determine an intent of a given voice input, the second predetermined library comprising a third partition having a third subset of keywords and a fourth partition having a fourth subset of keywords;

receiving, via the network interface, a response from the second playback device; and after receiving the response from the second playback device, performing an action based on an intent determined by at least one of the first local NLU or the second local NLU according to one or more particular keywords in the first voice input, wherein the first subset of keywords and the third subset of keywords include some or all of the same keywords, wherein the second subset of keywords differs from the first, third, and fourth subsets of keywords, and wherein the fourth subset of keywords differs from the first, second, and third subsets of keywords.

8. The method of claim 7, wherein the first predetermined library of keywords includes keywords that are not included within the second predetermined library of keywords.

9. The method of claim 7, wherein the first subset of keywords and the third subset of keywords are identical, and include a plurality of keywords associated with playback transport commands.

10. The method of claim 7, wherein the transmitting the input sound data via the network interface to a second playback device of the media playback system comprises selecting the second playback device from among a plurality of additional playback devices of the media playback system, wherein each of the plurality of additional playback devices comprises a respective NLU configured to detect, in input sound data, keywords from a respective predetermined library of keywords different from other respective predetermined libraries of keywords from which each respective NLU is configured to determine an intent of a given voice input, wherein the selection is based at least in part on the input sound data.

11. The method of claim 7, wherein the keywords of the first predetermined library of keywords associated with the first local NLU comprises keywords corresponding to a first intent category, and wherein the second predetermined library of keywords associated with the second local NLU comprises keywords corresponding to a second intent category.

12. The method of claim 7, wherein the playback device further comprises a voice assistant service (VAS) wake-word engine configured to receive input sound data representing the sound detected by the at least one microphone and generate a VAS wake-word event when the first wake-word engine detects a VAS wake word in the input sound data, wherein functions further comprise streaming sound data representing the sound detected by the at least one microphone to one or more servers of the voice assistant service when the VAS wake-word event is generated.

13. A tangible, non-transitory computer-readable medium storing instructions that, when executed by one or more processors, cause the one or more processors to perform functions comprising:
receiving input sound data representing sound detected by one or more microphones of a playback device;
detecting, via a command-keyword engine, a first command keyword in a first voice input represented in the input sound data, wherein the command-keyword engine is configured to (a) process input sound data representing the sound detected by the at least one microphone and (b) generate a command-keyword event when the command-keyword engine detects, in the input sound data, one of a plurality of keywords supported by the command-keyword engine;
in response to detecting the first command keyword, determining, via a first local natural language unit (NLU), whether the input sound data includes at least one keyword within a first predetermined library of keywords from which the first local NLU is configured to determine an intent of a given voice input, the first predetermined library of keywords comprising a first partition having a first subset of keywords and a second partition having a second subset of keywords;
transmitting, via a network interface over a local area network, the input sound data to a second playback device of a media playback system, the second playback device employing a second local NLU with a second predetermined library of keywords from which the second local NLU is configured to determine an intent of a given voice input, the second predetermined library comprising a third partition having a third subset of keywords and a fourth partition having a fourth subset of keywords;
receiving, via the network interface, a response from the second playback device; and
after receiving the response from the second playback device, performing an action based on an intent determined by at least one of the first local NLU or the second local NLU according to one or more particular keywords in the first voice input,
wherein the first subset of keywords and the third subset of keywords include some or all of the same keywords,
wherein the second subset of keywords differs from the first, third, and fourth subsets of keywords, and
wherein the fourth subset of keywords differs from the first, second, and third subsets of keywords.

14. The computer-readable medium of claim 13, wherein the first predetermined library of keywords includes keywords that are not included within the second predetermined library of keywords.

15. The computer-readable medium of claim 13, wherein the first subset of keywords and the third subset of keywords are identical, and include a plurality of keywords associated with playback transport commands.

16. The computer-readable medium of claim 13, wherein the transmitting the input sound data via the network interface to a second playback device of the media playback system comprises selecting the second playback device from among a plurality of additional playback devices of the media playback system, wherein each of the plurality of additional playback devices comprises a respective NLU configured to detect, in input sound data, keywords from a respective predetermined library of keywords different from other respective predetermined libraries of keywords from which each respective NLU is configured to determine an intent of a given voice input, wherein the selection is based at least in part on the input sound data.

17. The computer-readable medium of claim 13, wherein the keywords of the first predetermined library of keywords associated with the first local NLU comprises keywords corresponding to a first intent category, and wherein the second predetermined library of keywords associated with the second local NLU comprises keywords corresponding to a second intent category.

* * * * *